(12) United States Patent
Wei

(10) Patent No.: US 11,746,370 B2
(45) Date of Patent: Sep. 5, 2023

(54) METHODS AND COMPOSITIONS FOR ASSESSING AND TREATING INTRAOCULAR DISEASES AND DISORDERS

(71) Applicant: SMILEBIOTEK ZHUHAI LIMITED, Zhuhai (CN)

(72) Inventor: Lai Wei, Zhuhai (CN)

(73) Assignee: SMILEBIOTEK ZHUHAI LIMITED, Zhuhai (CN)

( * ) Notice: Subject to any disclaimer, the term of this patent is extended or adjusted under 35 U.S.C. 154(b) by 360 days.

(21) Appl. No.: 16/758,365

(22) PCT Filed: Oct. 26, 2018

(86) PCT No.: PCT/CN2018/112022
§ 371 (c)(1),
(2) Date: Apr. 22, 2020

(87) PCT Pub. No.: WO2019/080916
PCT Pub. Date: May 2, 2019

(65) Prior Publication Data
US 2020/0340030 A1   Oct. 29, 2020

(30) Foreign Application Priority Data
Oct. 26, 2017 (CN) .......................... 201711017087.3

(51) Int. Cl.
*C12Q 1/04* (2006.01)
*C12Q 1/6888* (2018.01)

(52) U.S. Cl.
CPC ............. *C12Q 1/04* (2013.01); *C12Q 1/6888* (2013.01); *G01N 2333/32* (2013.01); *G01N 2800/16* (2013.01)

(58) Field of Classification Search
CPC ........ C12Q 1/04; C12Q 1/6888; C12Q 1/689; G01N 2333/32; G01N 2800/16
See application file for complete search history.

(56) References Cited

U.S. PATENT DOCUMENTS

| 7,169,555 | B2 | 1/2007 | Stuber |
| 2010/0255474 | A1 | 10/2010 | Russwurm et al. |
| 2012/0282330 | A1 | 11/2012 | Wu |

FOREIGN PATENT DOCUMENTS

| CN | 1602207 | A | 3/2005 | |
| CN | 101041864 | A | 9/2007 | |
| CN | 103045761 | A | 4/2013 | |
| CN | 106834548 | A | 6/2017 | |
| WO | 00/40262 | A1 | 7/2000 | |
| WO | 02/085248 | A2 | 10/2002 | |
| WO | WO-02092853 | A1 * | 11/2002 | ............. C12Q 1/689 |
| WO | 2015023596 | A1 | 2/2015 | |
| WO | 2016196367 | A1 | 12/2016 | |

OTHER PUBLICATIONS

Yang et al. 2016 (Identification of pathogenic bacteria in aqueous and vitreous of endophthalmitis by 16S rDNA sequencing technique; Chin. J. Exp. Ophtalmol. 34(1): 885-886 (Year: 2016).*
Aarthi et al. 2011 (Identification of bacteria in culture negative and polymerase chain reaction (PCR) positive intraocular specimen from patients with infectious endophthalmitis; J of Microbiological Methods 85: 47-52). (Year: 2011).*
Carroll et al. 2000 (Detection of and Discrimination between Gram-Positive and Gram-Negative Bacteria in Intraocular Samples by Using Nested PCR; Journal of Clinical Microbiology 38(5):1753-1757) (Year: 2000).*
Bijsterveld et al. 1965 (Bacillus Infections of the Cornea; Arch Ophthal 74: 91-95) (Year: 1965).*
1st Office Action for Canadian patent application CA3 080 260, dated Apr. 26, 2021, 6 pages.
Response to 1st Office Action for Canadian patent application CA3 080 260, dated Aug. 26, 2021, 6 pages.
1st Office Action for Chinese patent application CN201711017087.3, dated Jun. 18, 2021, 10 pages.
Response to 1st Office Action for Chinese patent application CN201711017087.3, dated Jun. 18, 2021????, 4 pages.
European Search Report for European patent application EP18869530.8, dated Jun. 30, 2021, 23 pages.
Response to European Search Report for European patent application EP18869530.8, dated Jan. 18, 2022, 3 pages.
1st Office Action for Japanese patent application JP2020-543679, dated Jun. 1, 2021, 7 pages.
Response to 1st Office Action for Japanese patent application JP2020-543679, dated Jul. 21, 2021, 9 pages.
International Search Report for International patent application for PCT/CN2018/112022 (WO2019080916), dated May 2, 2019, 7 pages.
Written Opinion of the International Searching Authority for International patent application for PCT/CN2018/112022 (WO2019080916), dated May 2, 2019, 5 pages.
International Preliminary Report on Patentability for International patent application for PCT/CN2018/112022 (WO2019080916), dated Apr. 28, 2020, 6 pages.
Bui et al., "Single-Digit Pathogen and Attomolar Detection with the Naked Eye Using Liposome-Amplified Plasmonic Immunoassay," Nano Letters, vol. 15, No. 9, Aug. 26, 2015, p. 6239-6246 Doi:10.1021/acs.nanolett.5b02837.
Gilger et al., "Role of bacteria in the pathogenesis of recurrent uveitis in horses from the southeastern United States," Am J Vet Res, 2008, vol. 69, No. 10, p. 1329-1335.

(Continued)

*Primary Examiner* — Mary Maille Lyons
(74) *Attorney, Agent, or Firm* — Rimon, P.C.

(57) ABSTRACT

Provided are compositions, devices and systems, methods for assessing, treating and/or preventing an intraocular disease or disorder in a subject, wherein the etiology of the intraocular disease or disorder comprises infection of a microorganism in the intraocular space or cavity of the subject. Provided are compositions, devices and systems, and methods for assessing, treating and/or preventing age-related macular degeneration (AMD) in a subject, e.g., a human patient.

19 Claims, 28 Drawing Sheets

Specification includes a Sequence Listing.

(56) References Cited

OTHER PUBLICATIONS

Gündüz et al., "Conjunctival flora in Behçet patients," Canadian Journal of Ophthalmology, Aug. 1, 2008, vol. 43, No. 4, p. 476-479 Doi:10.3129/i08-089.
Han et al., "The study on rapid diagnosis of infective endophthalmitis with polymerase chain reaction combined with direct gene sequencing," Beijing Medical, vol. 30, No. 7, 2008, p. 418-420 DOI:10.15932/j.0253-9713.2008.07.027.
Knox et al., "Identification of Bacterial Pathogens in Patients With Endophthalmitis by 16S Ribosomal DNA Typing," American Journal of Ophthalmology, vol. 128, No. 4, Oct. 1999, p. 511-512.
Liu et al., "Chapter 16 Ocular trauma," Ophthalmology Foundation and Diagnosis and Treatment Practice, Jul. 31, 2015, p. 295-296.
Meri et al., "Microbes Bind Complement Inhibitor Factor H via a Common Site," PLOS Pathogens, vol. 9, No. 4,Apr. 2013, p. e1003308.
Milder et al., "Changes in Antibiotic Resistance Patterns of Conjunctival Flora Due to Repeated Use of Topical Antibiotics after Intravitreal Injection," Ophthalmology, vol. 119, No. 7, Jul. 1, 2012, p. 1420-1424 Doi:10.1016/j.ophtha.2012.01.016.
Okhravi et al., "PCR-Based Evidence of Bacterial Involvement in Eyes with Suspected Intraocular Infection," Investigative ophthalmology visual science, Oct. 2000, vol. 41, No. 11, p. 3474-3479.
Robman et al., "Exposure to Chlamydia pneumoniae infection and progression of age-related macular degeneration," American Journal of Epidemiology, vol. 161, No. 11, Jan. 1, 2005, p. 1013-1019 Doi:10.1093/aje/kwi130.
Thanathanee et al., "Conjunctivitis: Systematic Approach to Diagnosis and Therapy," Current Infectious Disease Reports (2011) 13:141-148 Doi:10.1007/s11908-011-0167-y.
Yang et al., "Identification of pathogenic bacteria in aqueous and vitreous of Endophthalmitis by 16S rDNA sequencing technique," Chin.J. Exp. Ophthalmol, vol. 34, No. 10, Oct. 2016, p. 883-887 Doi:10.3760/cma.j.issn.2095-0160.2016.10.004.
Yu et al., "PCR Assay for Detection of Bacillus Licheniformis," Guangdong Journal of Animal and Veterinary Science, 2015, vol. 40, No. 4, p. 35-37.
Zheng et al., "Microbiome Characterization in Retina and choroid of Patients with Age-related Macular Degeneration," Investigative Ophthalmology Visual Science, abstract, May 1, 2016, 2 pages.
Bacillus licheniformis strain HRBL-15TD17 chromosome, complete genome, Kim, H.-R., Genbank database, GenBank: CP014781.1, Mar. 22, 2016.
Schmieder R, Edwards R. Quality control and preprocessing of metagenomic datasets. Bioinformatics 2011;27:863-4. doi: 10.1093/bioinformatics/btr026. Epub Jan. 28, 2011.
Kim D, Langmead B, Salzberg SL. HISAT: a fast spliced aligner with low memory requirements. Nat Methods 2015;12:357-60. doi: 10.1038/nmeth.3317. Epub Mar. 9, 2015.
Schmieder R, Edwards R. Fast identification and removal of sequence contamination from genomic and metagenomic datasets. PLoS One 2011;6:e17288. doi: 10.1371/journal.pone.0017288.
Wood DE, Salzberg SL. Kraken: ultrafast metagenomic sequence classification using exact alignments. Genome Biol 2014;15:R46. doi: 10.1186/gb-2014-15-3-r46.
Abubucker S, Segata N. Goll J, et al. Metabolic reconstruction for metagenomic data and its application to the human microbiome. PLoS Comput Biol 2012;8:e1002358. doi: 10.1371/journal.pcbi.1002358. Epub Jun. 13, 2012.
Segata N, Izard J, Waldron L, et al. Metagenomic biomarker discovery and explanation. Genome Biol 2011;12:R60. doi: 10.1186/gb-2011-12-6-r60.
Peyman GA, Paque JT, Meisels HI, Bennett TO. Postoperative endophthalmitis: a comparison of methods for treatment and prophlaxis with gentamicin. Ophthalmic Surg 1975;6:45-55 (Abstract).
Crabb JW, Miyagi M, Gu X, et al. Drusen proteome analysis: an approach to the etiology of age-related macular degeneration. Proc Natl Acad Sci U S A 2002;99:14682-7. Epub Oct. 21, 2002.

Doyle SL, Campbell M. Ozaki E, et al. NLRP3 has a protective role in age-related macular degeneration through the induction of IL-18 by drusen components. Nat Med 2012;18:791-8. doi: 10.103S/nm.2717.
Wang Y, Hanus JW, Abu-Asab MS, et al. NLRP3 upregulation in retinal pigment epithelium in age-related macular degeneration. Int J Mol Sci 2016;17(1).E73. doi: 10.3390/ijms17010073.
Jager RD, Mieler WF, Miller JW. Age-related macular degeneration. N Engl J Med 2008;358:2606-17. doi: 10.1056/NEJMra0801537.
Sacconi R, Corbelli E, Querques L, Bandello F, Querques G. A review of current and future management of geographic atrophy. Ophthalmol Ther 2017;6:69-77. doi: 10.1007/S40123-017-0086-6. Epub Apr. 8, 2017.
Fritsche LG, Fariss RN, Stambolian D, Abecasis GR, Curcio CA, Swaroop A. Age-related macular degeneration: genetics and biology coming together. Annu Rev Genomics Hum Genet 2014;15:151-71.:10.1146/ annurev-genom-090413-25610. Epub Apr. 16, 2014.
Fritsche LG, Igl W, Bailey JN, et al. A large genome-wide association study of age-related macular degeneration highlights contributions of rare and common variants. Nat Genet 2016;48:134-43. doi: 10.1038/ng.3448. Epub Dec. 21, 2015.
Fritsche LG, Chen W, Schu M, et al. Seven new loci associated with age-related macular degeneration. Nat Genet 2013;Apr. 2013;45:433-9.
Forrester JV, Kiaska IP, Yu T, Kuffova L. Uveitis in mouse and man. Int Rev Immunol 2013;32:76-96. doi 10.3109/08830185.2012.747524.
Abubucker S, Segata N, Goll J, et al. Metabolic reconstruction for metagenomic data and its application to the human microbiome. PLoS Comput Biol 2012;8:e1002358. doi: 10.1371/journal.pcbl.. Epub Jun. 13, 2012.
Deramo VA, Ting TD. Treatment of Propionibacterium acnes endophthalmitis. Curr Opin Ophthalmol 2001;12:225-9.
Perry A, Lambert P. Propionibacterium acnes: infection beyond the skin. Expert Rev Anti Infect Ther 2011;9:1149-56. doi: 10.586/eri.11.137.
Franzosa EA, Hsu T, Sirota-Madi A, et al. Sequencing and beyond: integrating molecular 'omics' for microbial community profiling. Nat Rev Microbiol 2015;13:360-72. doi: 10.1038/nrmicro3451. Epub Apr. 27, 2015.
Kugadas A, Gadjeva M. Impact of microbiome on ocular health. Ocul Surf 2016;14:342-9. doi: 10.1016/j.jtos.2016.04.004. Epub May 14.
St Leger AJ, Desai JV, Drummond RA, et al. An ocular commensal protects against corneal infection by driving an interleukin-17 response from mucosal gammadelta T cells. Immunity 2017;47:148-58.e5. doi: 10.1016/j. immuni.2017.06.014. Epub Jul. 11.
Schumaker VN, Zavodszky P, Poon PH. Activation of the first component of complement. Annu Rev Immunol 1987;5:21-42.
Johnson LV, Leitner WP, Rivest AJ, Staples MK, Radeke MJ, Anderson DH. The Alzheimer's A beta-peptide is deposited at sites of complement activation in pathologic deposits associated with aging and age-related macular degeneration. Proc Natl Acad Sci U S A 2002;99:11830-5. Epub Aug. 20, 2002.
Kumar DK, Choi SH, Washicosky KJ, et al. Amyloid-beta peptide protects against microbial infection in mouse and worm models of Alzheimer's disease. Sci Transl Med 2016;8:340ra72. doi: 10.1126/scitransimed.aaf059.
Singh B, Su YC, Riesbeck K. Vitronectin in bacterial pathogenesis: a host protein used in complement escape and cellular invasion. Mol Microbiol 2010;78:545-60. doi: 10.1111/j.365-2958.010.07373.x. Epub Sep. 27, 2010.
Kattan OM, Kasravi FB, Elford EL, Schell MT, Harris HW. Apolipoprotein E-mediated immune regulation in sepsis. J Immunol 2008;181:1399-408.
Khan KN, Mahroo OA, Khan RS, et al. Differentiating drusen: Drusen and drusen-like appearances associated with ageing, age-related macular degeneration, inherited eye disease and other pathological processes. Prog Retin Eye Res 2016;53:70-106.:10.1016/j.preteyeres.2016.04.008. Epub May 10.
Mattapallil MJ, Caspi RR. Compliments of factor H: What's in it for AMD? Immunity 2017;46:167-9. doi: 10.1016/j.immuni.2017.02.008.

(56) References Cited

OTHER PUBLICATIONS

Friedrich U, Datta S, Schubert T, et al. Synonymous variants in HTRA1 implicated in AMD susceptibility impair its capacity to regulate TGF-beta signaling. Hum Mol Genet 2015;24:6361-73. doi: 10.1093/hmg/ddv346. Epub Aug. 26, 2015.

Morrison MA, Magalhaes TR, Ramke J, et al. Ancestry of the Timorese: age-related macular degeneration associated genotype and allele sharing among human populations from throughout the world. Front Genet 2015;6:238.:10.3389/fgene.2015.00238. eCollection 2015.

* cited by examiner

Figure 7
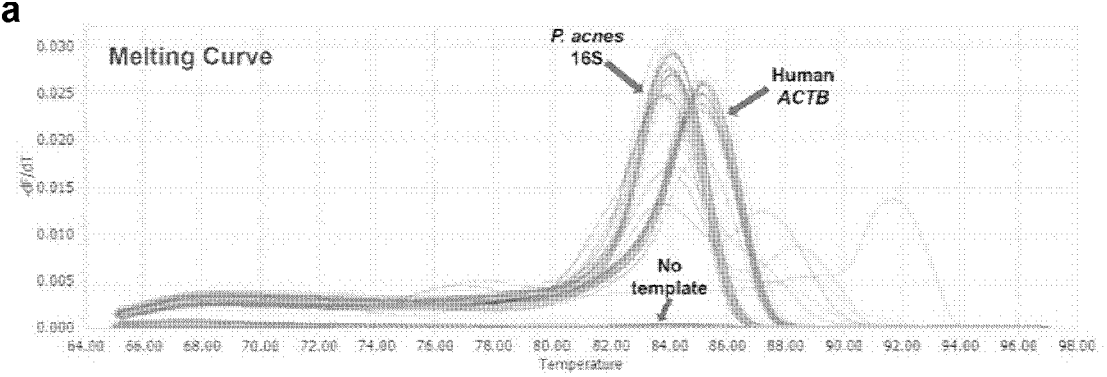
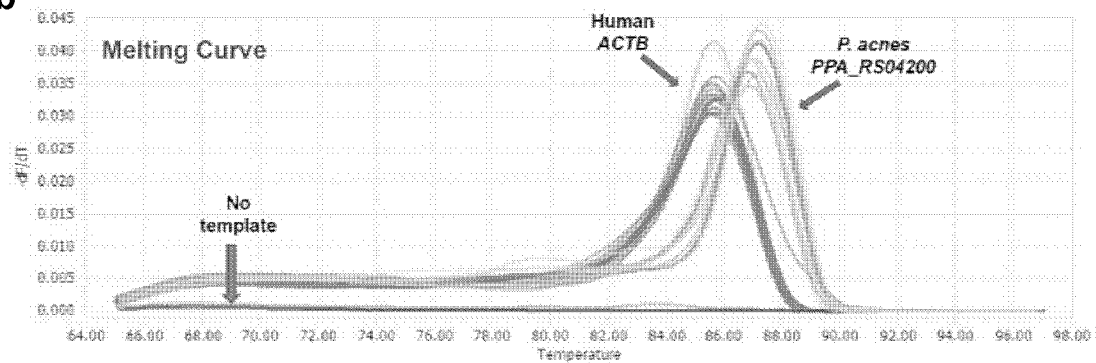

Figure 12
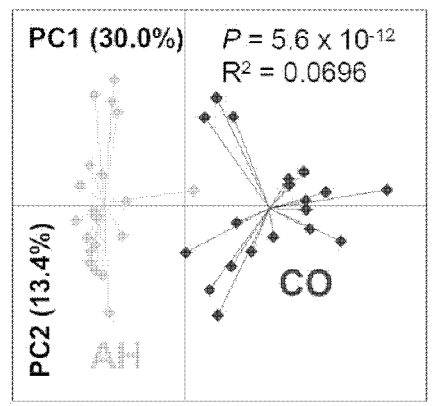
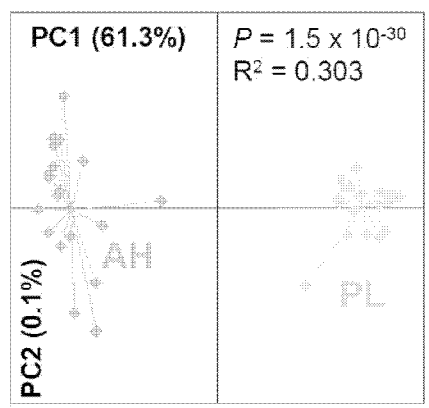
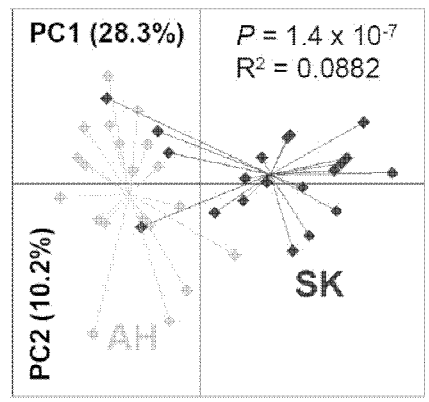

Figure 13
a
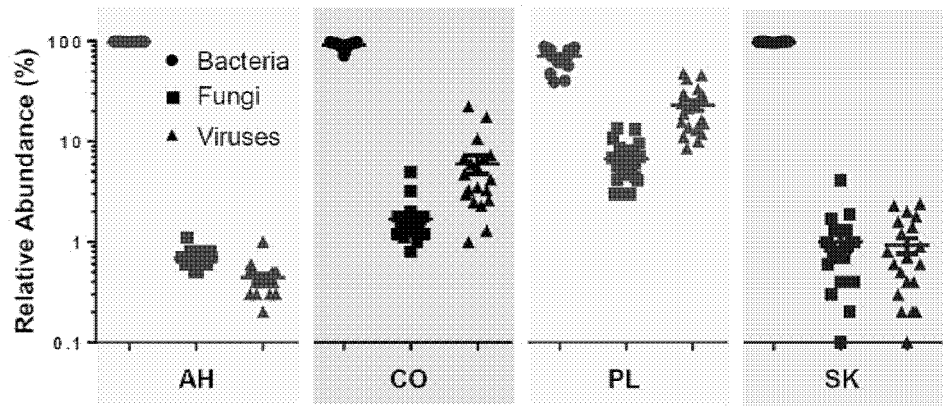
b
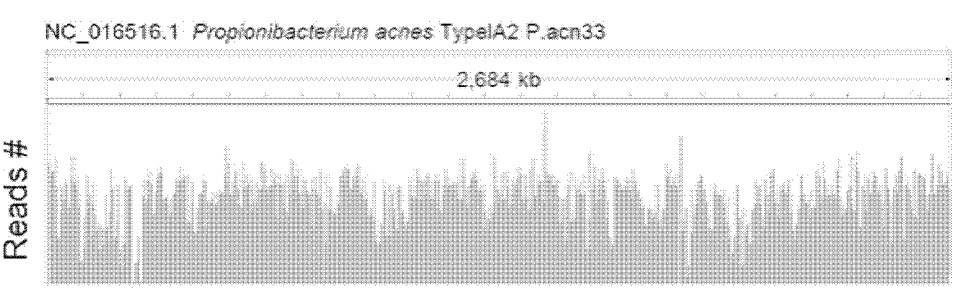

Figure 19
a
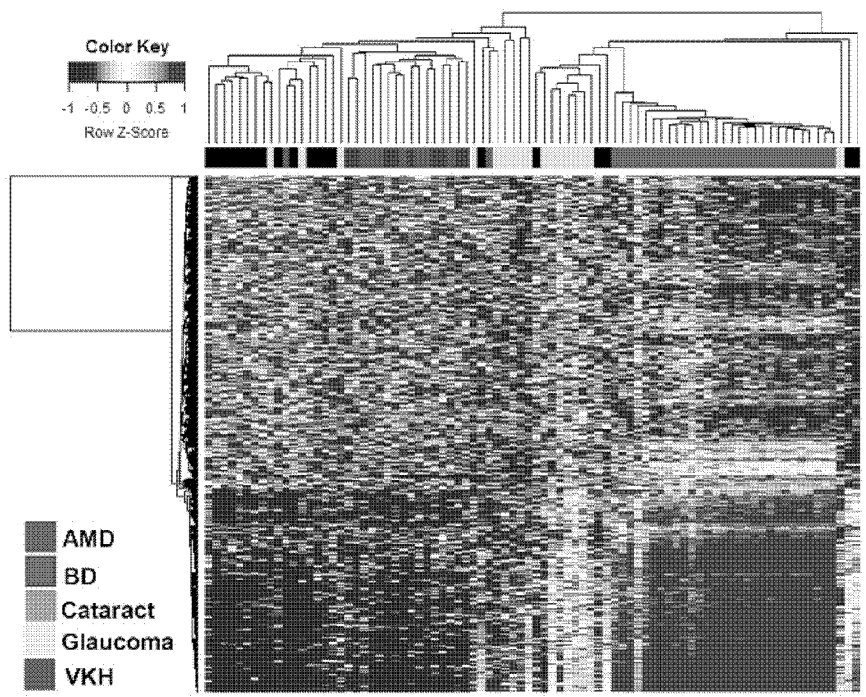
b
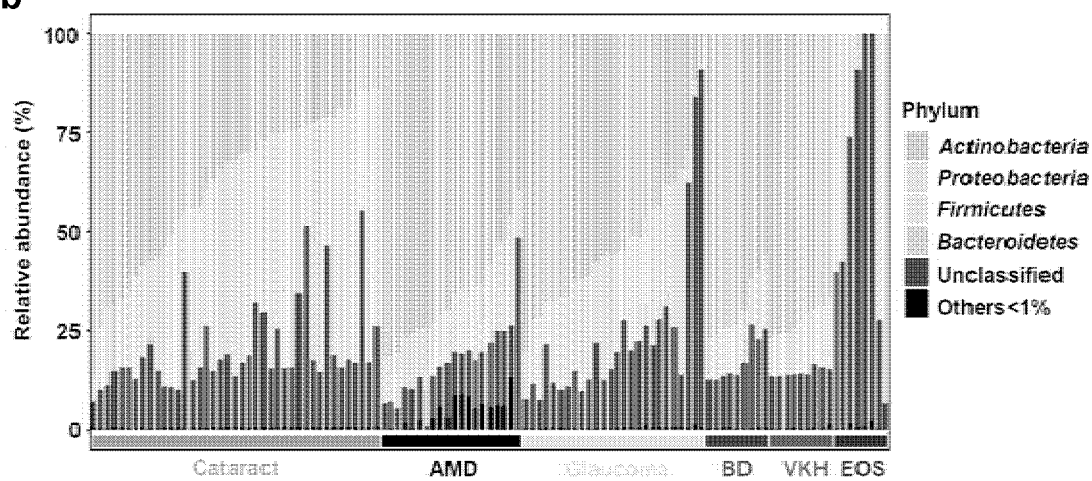

Figure 20

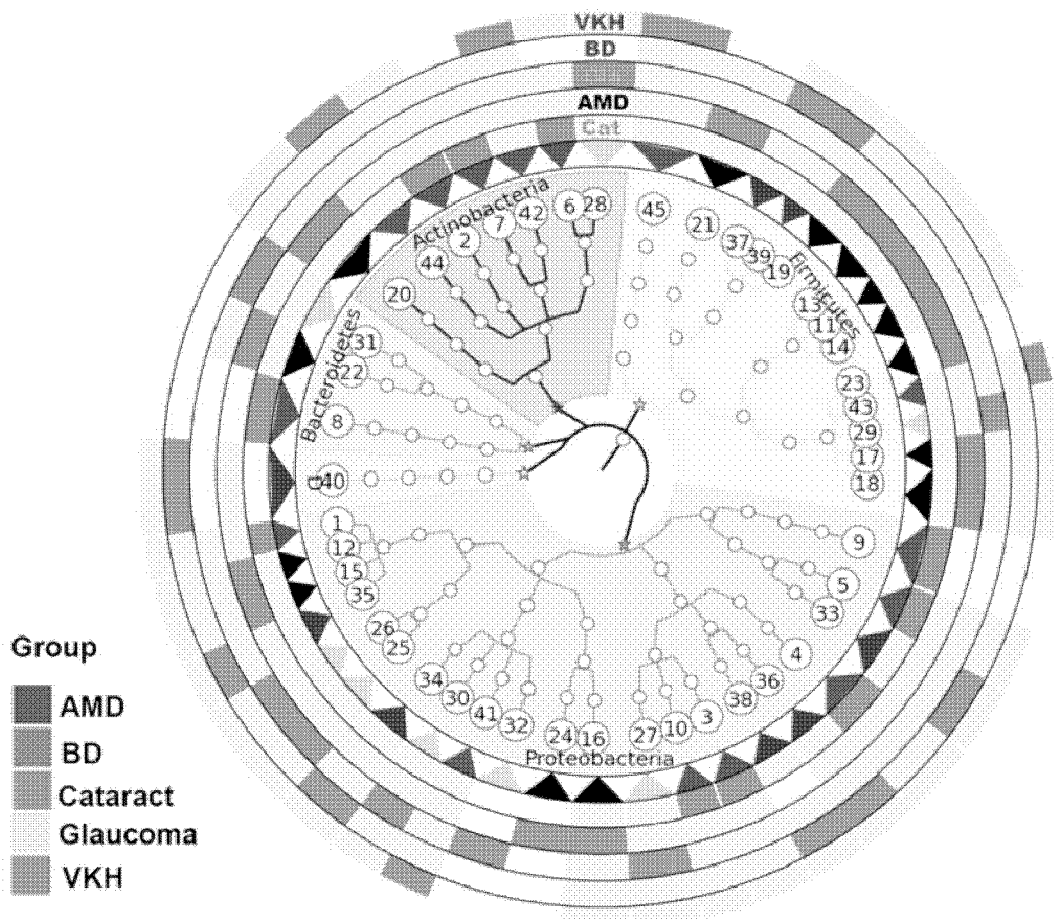

Group
- AMD
- BD
- Cataract
- Glaucoma
- VKH

| | | |
|---|---|---|
| 1 Pseudomonas mendocina | 16 Stenotrophomonas maltophilia | 31 Dyadobacter fermentans |
| 2 Kytococcus sedentarius | 17 Bacillus cereus | 32 Serratia marcescens |
| 3 Alicycliphilus denitrificans | 18 Bacillus megaterium | 33 Sphingomonas wittichii |
| 4 Achromobacter xylosoxidans | 19 Lactobacillus reuteri | 34 Klebsiella pneumoniae |
| 5 Sphingobium japonicum | 20 Gardnerella vaginalis | 35 Pseudomonas fluorescens |
| 6 Mycobacterium abscessus | 21 Enterococcus faecium | 36 Ralstonia pickettii |
| 7 Arthrobacter aurescens | 22 Cytophaga hutchinsonii | 37 Lactobacillus crispatus |
| 8 Prevotella dentalis | 23 Bacillus licheniformis | 38 Burkholderia multivorans |
| 9 Sinorhizobium meliloti | 24 Xanthomonas oryzae | 39 Lactobacillus delbrueckii |
| 10 Acidovorax ebreus | 25 Acinetobacter baumannii | 40 Meiothermus silvanus (D) |
| 11 Staphylococcus epidermidis | 26 Acinetobacter calcoaceticus | 41 Escherichia coli |
| 12 Pseudomonas aeruginosa | 27 Comamonas testosteroni | 42 Micrococcus luteus |
| 13 Staphylococcus aureus | 28 Mycobacterium kansasii | 43 Bacillus subtilis |
| 14 Staphylococcus haemolyticus | 29 Bacillus thuringiensis | 44 Corynebacterium aurimucosum |
| 15 Pseudomonas putida | 30 Citrobacter koseri | 45 Finegoldia magna |

Figure 22
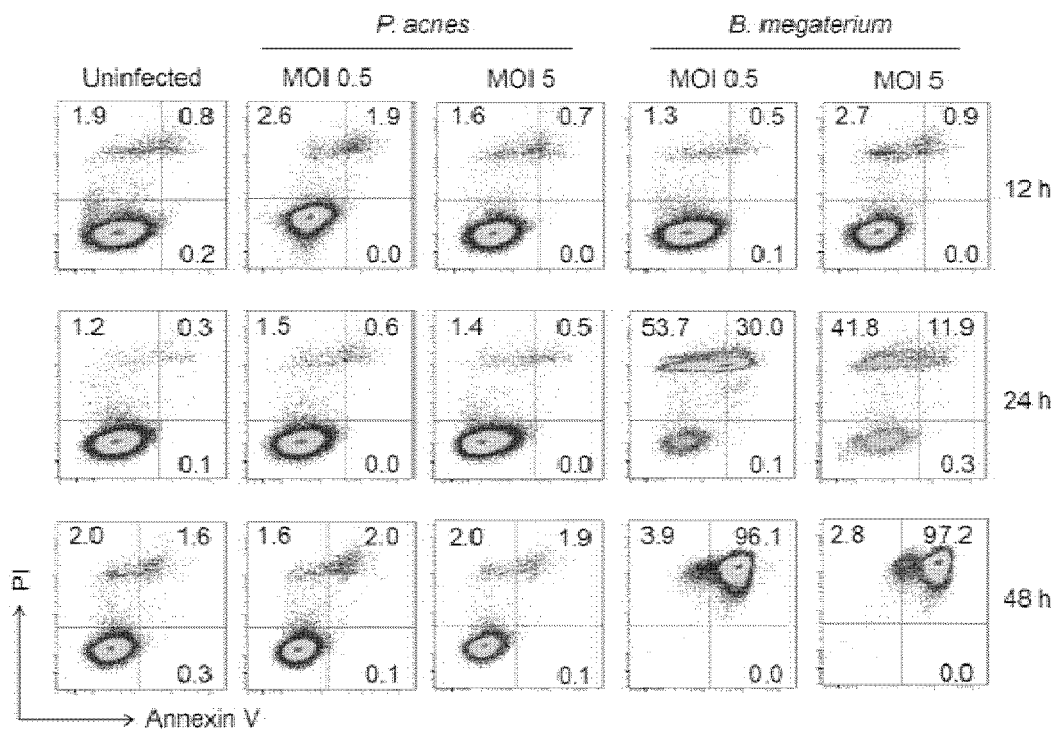
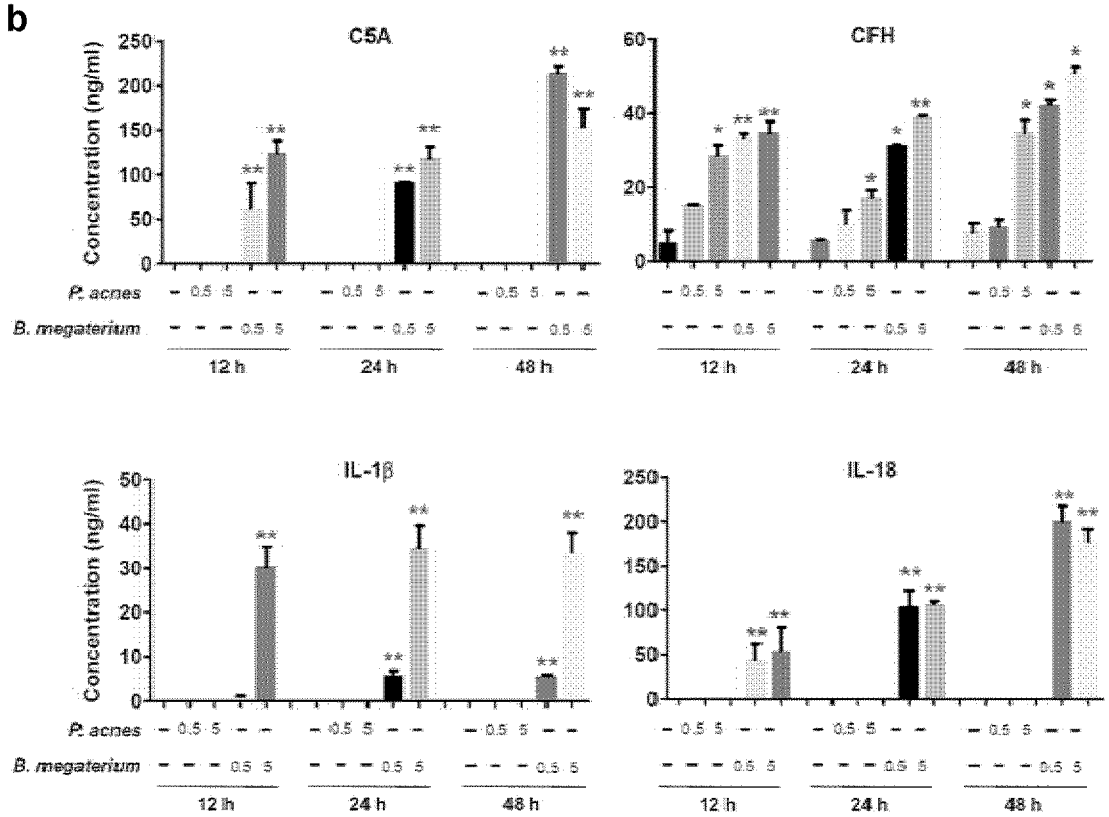

Figure 24
a
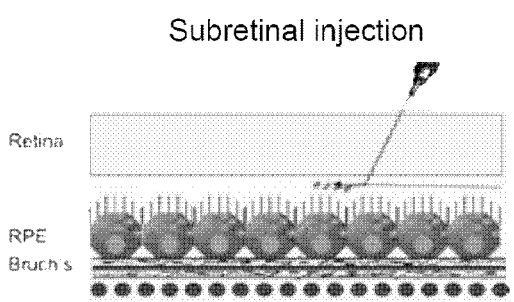
b
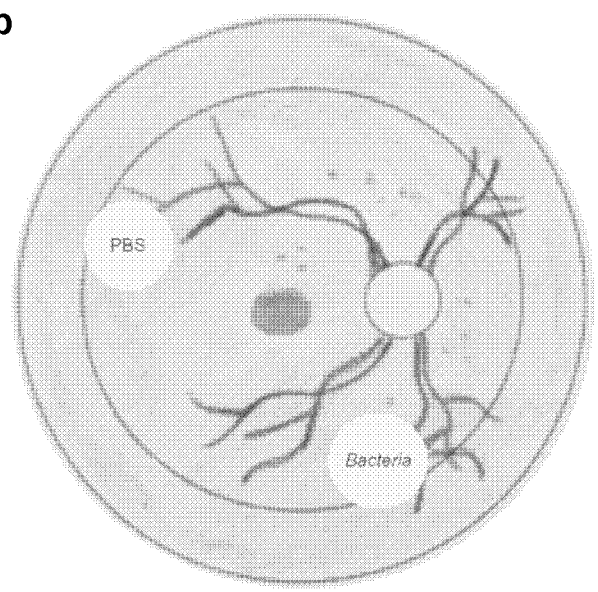

METHODS AND COMPOSITIONS FOR ASSESSING AND TREATING INTRAOCULAR DISEASES AND DISORDERS

The present application is a U.S. national phase filing of International Patent Application Serial No. PCT/CN2018/112022, filed on Oct. 26, 2018, entitled "METHODS AND COMPOSITIONS FOR ASSESSING AND TREATING INTRAOCULAR DISEASES AND DISORDERS," which claims priority to Chinese patent application No. 201711017087.3, filed on Oct. 26, 2017. The contents and disclosures of the above applications are incorporated herein by reference in their entireties for all purposes.

SEQUENCE LISTING ON ASCII TEXT

This patent or application file contains a Sequence Listing submitted in computer readable ASCII text format (file name: 4863-2000130_20200421_SeqList_ST25.txt, date recorded: Apr. 21, 2020, and size: 9,667 bytes). The content of the Sequence Listing file is incorporated herein by reference in its entirety.

TECHNICAL FIELD

In some aspect, the present disclosure relates to compositions, e.g., devices and systems, and methods for assessing, treating and/or preventing an intraocular disease or disorder in a subject, wherein the etiology of the intraocular disease or disorder comprises infection of a microorganism in the intraocular space of the subject. In some embodiments, the present disclosure relates to compositions, e.g., devices and systems, and methods for assessing, treating and/or preventing age-related macular degeneration (AMD) in a subject, e.g., a human patient.

BACKGROUND

In the elderly population, Age-related macular degeneration (AMD) is the leading cause of irreversible vision loss worldwide[1]. It is characterized by confluent soft drusen deposited between retinal pigment epithelium (RPE) and the Bruch's membrane and/or retinal pigmentary changes in the macula at the early stage (intermediate AMD). At later stages, advanced AMD is characterized by two major subtypes, geographic atrophy (dry AMD) or choroidal neovascularization (wet AMD) in the macula[1]. While anti-VEGF therapies have been used to control wet AMD, currently there is no approved therapy for dry AMD[1,2].

The pathogenesis of AMD involves both genetic and environmental factors. Numerous studies have identified variations at the loci of genes that are associated with AMD susceptibility, including complement factor H (CFH), age-related maculopathy susceptibility 2 (ARMS2), HtrA serine peptidase 1 (HTRA1), indicating that AMD is possible an inflammatory disease[3-5]. Currently, the environmental factors triggering the local inflammation and leading to the early soft drusen in AMD pathology are not clear.

There is a need for improved compositions and methods for assessing, treating or preventing intraocular diseases or disorders in a subject, e.g., a mammal or a human. The present disclosure addresses this and other related needs.

SUMMARY

In one aspect, disclosed herein is a method for assessing an intraocular disease or disorder in a subject, which method comprises assessing the presence, absence and/or quantity of a microorganism in an intraocular space or cavity of a subject, wherein the etiology of said intraocular disease or disorder comprises infection of said microorganism in said intraocular space or cavity of said subject.

In another aspect, disclosed herein is a kit or device for assessing an intraocular disease or disorder in a subject, which kit or device comprises reagents for assessing the presence, absence, quantity, the infectious status, and/or the microbiota of a microorganism in an intraocular space or cavity, or an intraocular sample of a subject, wherein the etiology of said intraocular disease or disorder comprises infection of said microorganism in said intraocular space or cavity of said subject.

In still another aspect, disclosed herein is a method for treating and/or preventing an intraocular disease or disorder in a subject, which method comprises administering, to a subject in need of such treatment and/or prevention, an effective amount of an agent that kills or inhibits a microorganism in an intraocular space or cavity of a subject, wherein the etiology of said intraocular disease or disorder comprises infection of said microorganism in said intraocular space or cavity of said subject.

In yet another aspect, disclosed herein is an use of an effective amount of an agent that kills or inhibits a microorganism in an intraocular space or cavity of a subject for the manufacture of a medicament for treating or preventing an intraocular disease or disorder in the subject, wherein the etiology of said intraocular disease or disorder comprises infection of said microorganism in said intraocular space or cavity of said subject.

In yet another aspect, disclosed herein is a combination, which combination comprises an effective amount of an agent that kills or inhibits a microorganism in an intraocular space or cavity of a subject and an effective amount of a second agent for treating and/or preventing an intraocular disease or disorder, wherein the etiology of said intraocular disease or disorder comprises infection of said microorganism in said intraocular space or cavity of said subject. Uses of the combination for treating and/or preventing an intraocular disease or disorder in a subject are also disclosed. Uses of the combination for the manufacture of a medicament for treating or preventing an intraocular disease or disorder in a subject further disclosed.

In yet another aspect, disclosed herein is a method for the detection of intraocular microbiota using metagenomic sequencing analysis and/or real-time PCR analysis, wherein the microbiota comprises or includes *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

In yet another aspect, disclosed herein is a method for the diagnosis of age-related macular degeneration, wherein the steps of the method comprise or include: (1) detecting the intraocular microbiota selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium* using metagenomic sequencing analysis, and/or (2) detecting the intraocular microbiota selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium* using real-time PCR analysis.

In yet another aspect, disclosed herein is one or more primer pairs for the production of age-related macular degeneration diagnostic kits, wherein the primer pairs are selected from one or more of the followings: (1) SEQ ID NO:1, SEQ ID NO:2, (2) SEQ ID NO:3, SEQ ID NO:4, (3) SEQ ID NO:5, SEQ ID NO:6, (4) SEQ ID NO:7, SEQ ID NO:8, (5) SEQ ID NO:9, SEQ ID NO:10, (6) SEQ ID NO:11, SEQ ID NO:12, (7) SEQ ID NO:13, SEQ ID NO:14, (8) SEQ ID NO:15, SEQ ID NO:16, (9) SEQ ID NO:17, SEQ ID NO:18, (10) SEQ ID NO:19, SEQ ID NO:20, (11) SEQ ID NO:21, SEQ ID NO:22, (12) SEQ ID NO:23, SEQ ID NO:24, (13) SEQ ID NO:25, SEQ ID NO:26, (14) SEQ ID NO:27, SEQ ID NO:28, (15) SEQ ID NO:29, SEQ ID NO:30. The uses of the primer pairs for the production of age-related macular degeneration diagnostic kits are also disclosed.

In yet another aspect, disclosed herein is a kit for the diagnosis of age-related macular degeneration, wherein the kit comprises: (1) SYBR Green I; (2) Taq enzyme; (3) primer pairs; (4) dNTP; (5) buffer; (6) sterilized water, and wherein the primer pairs are selected from one or more of the followings: (1) SEQ ID NO:1, SEQ ID NO:2, (2) SEQ ID NO:3, SEQ ID NO:4, (3) SEQ ID NO:5, SEQ ID NO:6, (4) SEQ ID NO:7, SEQ ID NO:8, (5) SEQ ID NO:9, SEQ ID NO:10, (6) SEQ ID NO:11, SEQ ID NO:12, (7) SEQ ID NO:13, SEQ ID NO:14, (8) SEQ ID NO:15, SEQ ID NO:16, (9) SEQ ID NO:17, SEQ ID NO:18, (10) SEQ ID NO:19, SEQ ID NO:20, (11) SEQ ID NO:21, SEQ ID NO:22, (12) SEQ ID NO:23, SEQ ID NO:24, (13) SEQ ID NO:25, SEQ ID NO:26, (14) SEQ ID NO:27, SEQ ID NO:28, (15) SEQ ID NO:29, SEQ ID NO:30. The uses of the kit for the diagnosis of age-related macular degeneration are also disclosed.

In yet another aspect, disclosed herein is a medicine for the treatment of age-related macular degeneration, wherein the medicine is for killing or inhibiting microbiota, and wherein the microbiota is selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*. The uses of the medicine for the treatment of age-related macular degeneration is also disclosed.

BRIEF DESCRIPTION OF THE DRAWINGS

FIG. 7 illustrates the melting curve of real-time PCR assays using primer pairs of P. spp 16S/Human ACTB (a), *P. acnes* PPA_RS045200/HumanACTB (b).

FIG. 12 illustrates similarity of the microbial community between (a) AH and Conjunctiva (CO), (b) AH and Plasma (PL), and (c) AH and Skin (SK) was analyzed by principle coordination analysis with Bray-Curtis distance. P value was calculated using PERMANOVA test.

FIG. 13(*a*) illustrates relative abundance of bacteria, fungi, and viruses among AH, CO, PL, and SK samples analyzed by metagenomic sequencing. FIG. 13(*b*) illustrates alignment of all reads mapped to *P. acnes* to the template genome of P. acn33.

FIG. 14(*b*) illustrates the average numbers of reads passing quality filters for Blank, Wash Solution, Anesthesia, Disinfectant, NaCl Solution, Mydriatic, and AH samples.

FIG. 19(*a*) illustrates hierarchical clustering analysis of the functional genes in the intraocular metagenomes in patients with cataract, AMD, glaucoma, BD, and VKH. FIG. 19(*b*) illustrates relative abundance of the four major phyla of bacteria in the intraocular metagenomes in patients with cataract, AMD, glaucoma, BD, VKH, or EOS.

FIG. 20 illustrates species highly enriched in intraocular metagenomes in patients with cataract, AMD, glaucoma, BD, VKH, identified using LefSe.

FIG. 22(*a*) illustrates ARPE19 cells were cocultured with live *P. acnes* and *B. megaterium* (at MOI of 0.5 and 5). The cell death was measured using staining of Propidium iodide (PI) and Annexin V, and detected by flow cytometry at 12 h, 24 h, and 48 h, respectively. FIG. 22(*b*) illustrates the concentration of active forms of CSA, CFH, IL-1, and IL-18 in the supernatants from ARPE19 cells cocultured with live *P. acnes* and *B. megaterium* was measured by ELISA. The statistical difference was measured against the uninfected condition. *P<0.05, Student's T test; **P<0.01, Student's T test.

FIG. 24 illustrates subretinal injection anatomical (a) and retinal (b) locations, as well as the melting curve of real-time PCR assays using primer pairs of *B. megaterium*/Human ACTB (c).

DETAILED DESCRIPTION

A. General Techniques

Figure 1:
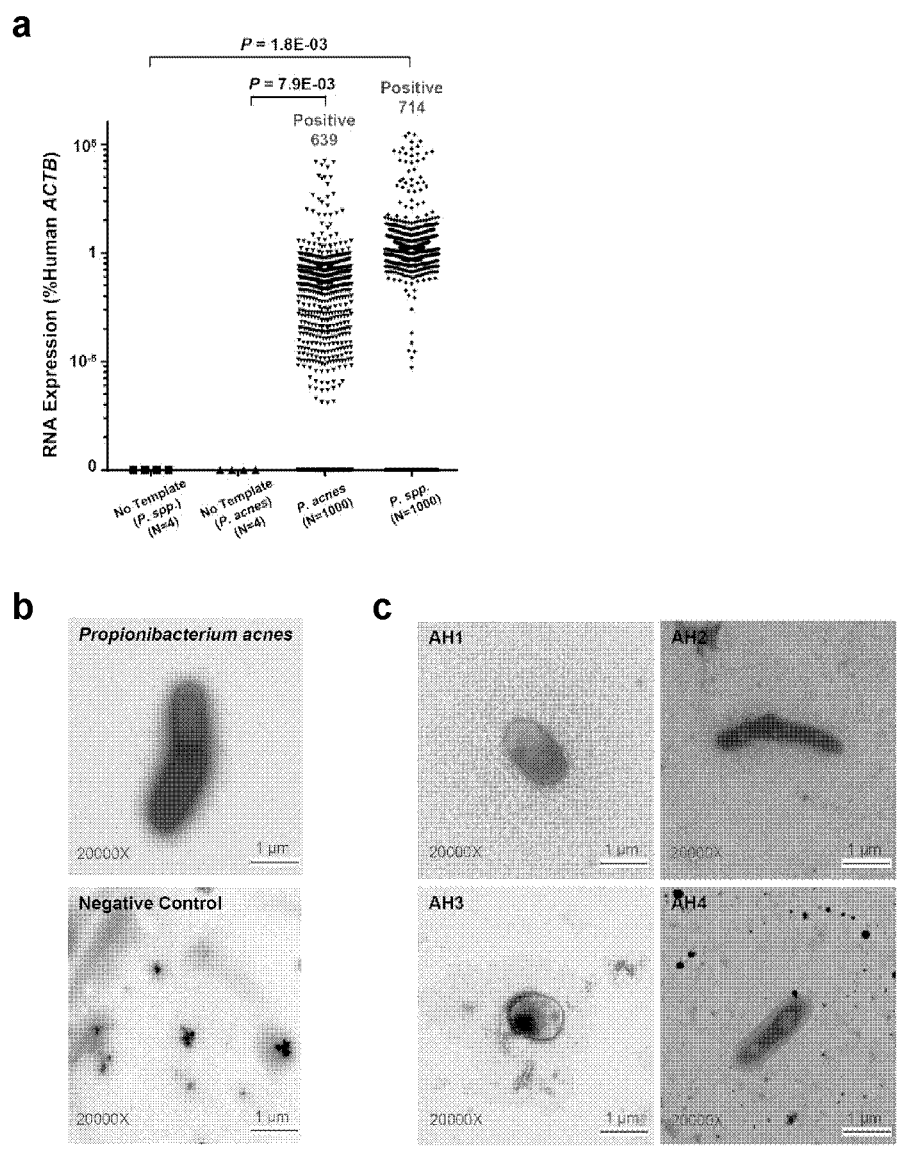
FIG. 1 illustrates detection of intraocular bacteria in AH specimens. (a) Relative expression of *Propionibacterium.* spp. 16S rRNA and a *P. acnes* specific gene—PPA_RS04200 (presented as the percentage of human ACTB expression) in the aqueous humors (AH) from 1000 human eyes undergoing cataract surgery was quantified using real-time PCR assays. The P value was calculated using parametric (Student's) T test. (b) Negative staining transmission electron microscopy was used to visualize cultured *P. acnes* at 20,000× magnification. The negative control shows the visualization of water without AH specimen. (c) Negative staining transmission electron microscopy shows bacteria in minimally manipulated fresh AH specimens at 20,000× magnification.

The practice of the present invention will employ, unless otherwise indicated, conventional techniques of molecular biology (including recombinant techniques), microbiology, cell biology, biochemistry, immunology, and pharmacology, which are within the skill of the art. Such techniques are explained fully in the literature, such as, *Molecular Cloning: A Laboratory Manual, 2nd ed.* (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy, 20th ed.*, (Lippincott, Williams & Wilkins 2003).

B. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

The terms "polypeptide," "oligopeptide," "peptide," and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the terms "variant" is used in reference to polypeptides that have some degree of amino acid sequence identity to a parent polypeptide sequence. A variant is similar to a parent sequence, but has at least one substitution, deletion or insertion in their amino acid sequence that makes them different in sequence from a parent polypeptide. Additionally, a variant may retain the functional characteristics of the parent polypeptide, e.g., maintaining a biological activity that is at least 50%, 60%, 70%, 80%, 90%, 95%, 98%, or 99% of that of the parent polypeptide.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included within the definition. As used herein, the term encompasses not only intact polyclonal or monoclonal antibodies, but also fragments thereof (such as Fab, Fab', F(ab')2, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "epitope" refers to a portion of an antigen, e.g., a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example an antibody raised against an immune complex of a second antibody and its corresponding antigen may be considered to be an SBP member for the immune complex.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O— allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, the term "homologue" is used to refer to a nucleic acid which differs from a naturally occurring nucleic acid (e.g., the "prototype" or "wild-type" nucleic acid) by minor modifications to the naturally occurring nucleic acid, but which maintains the basic nucleotide structure of the naturally occurring form. Such changes include, but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus sites can be inserted immediately 5' of the start codon and may enhance expression. See, e.g., Kozak (1991) *J. Biol. Chem.* 266:19867-19870. The desirability of (or need for) such modification may be empirically determined.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent or treatment, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art. In some embodiments, "treatment" means any manner in which the symptoms of a condition, disorder or disease are ameliorated or otherwise beneficially altered. Treatment also encompasses any pharmaceutical use of the compositions herein. In some embodiments, "amelioration" of the symptoms of a particular disorder by administration of a particular pharmaceutical composition refers to any lessening, whether permanent or temporary, lasting or transient that can be attributed to or associated with administration of the composition.

The term "prediction" or "prognosis" is often used herein to refer to the likelihood that a patient will respond either favorably or unfavorably to a drug or set of drugs, or the likely outcome of a disease. In one embodiment, the prediction relates to the extent of those responses or outcomes. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20$^{th}$ ed., (Lippincott, Williams & Wilkins 2003). Except insofar as any conventional media or agent is incompatible with the active compound, such use in the compositions is contemplated.

A "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.*, 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

As used herein, the term "therapeutically effective amount" or "effective amount" refers to an amount of a therapeutic agent that when administered alone or in combination with an additional therapeutic agent to a cell, tissue, or subject is effective to prevent or ameliorate an intraocular disease or disorder in a subject. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In some embodiment, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

The terms "level" or "levels" are used to refer to the presence and/or amount of a target, e.g., a microorganism that is part of the etiology of an intraocular disease or disorder, and can be determined qualitatively or quantitatively. A "qualitative" change in the target, microorganism level refers to the appearance or disappearance of a target, microorganism that is not detectable or is present in samples obtained from normal controls. A "quantitative" change in the levels of one or more targets, microorganisms refers to a measurable increase or decrease in the target, microorganism levels when compared to a healthy control.

A "healthy control" or "normal control" is a biological sample taken from an individual who does not suffer from an intraocular disease or disorder. A "negative control" is a sample that lacks any of the specific analyte the assay is designed to detect and thus provides a reference baseline for the assay.

As used herein, "mammal" refers to any of the mammalian class of species. Frequently, the term "mammal," as used herein, refers to humans, human subjects or human patients. "Mammal" also refers to any of the non-human mammalian class of species, e.g., experimental, companion or economic non-human mammals. Exemplary non-human mammals include mice, rats, rabbits, cats, dogs, pigs, cattle, sheep, goats, horses, monkeys, Gorillas and chimpanzees.

As used herein, "production by recombinant means" refers to production methods that use recombinant nucleic acid methods that rely on well-known methods of molecular biology for expressing proteins encoded by cloned nucleic acids.

As used herein, the term "subject" is not limited to a specific species or sample type. For example, the term "subject" may refer to a patient, and frequently a human patient. However, this term is not limited to humans and thus encompasses a variety of non-human animal or mammalian species.

As used herein, a "prodrug" is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

C. Methods for Assessing an Intraocular Disease or Disorder

In one aspect, disclosed herein is a method for assessing an intraocular disease or disorder in a subject, which method comprises assessing the presence, absence and/or quantity of a microorganism in an intraocular space or cavity of a subject, wherein the etiology of said intraocular disease or disorder comprises infection of said microorganism in said intraocular space or cavity of said subject.

In some embodiments, the present method comprises assessing the presence or absence of the microorganism in the intraocular space or cavity for assessing an intraocular disease or disorder in a subject. In other embodiments, the present method comprises assessing the quantity of the microorganism in the intraocular space or cavity for assessing an intraocular disease or disorder in a subject. The present method can assess additional relevant parameters of the microorganisms in the intraocular space or cavity. For example, the present method can further comprise assessing infectious status of the microorganism in the intraocular space or cavity for assessing an intraocular disease or disorder in a subject.

The present method can assess any suitable microorganism in the intraocular space or cavity to assess an intraocular disease or disorder in a subject. For example, the present method can assess a bacterium, a fungus, a virus, or a combination thereof, in the intraocular space or cavity to assess an intraocular disease or disorder in a subject.

The present method can assess any suitable number of microorganism(s) in the intraocular space or cavity to assess an intraocular disease or disorder in a subject. For example, the present method can comprise assessing the presence, absence, quantity, and/or the infectious status of a single microorganism in the intraocular space or cavity for assessing an intraocular disease or disorder in a subject. In another example, the present method can comprise assessing the presence, absence, quantity, and/or the infectious status of multiple microorganisms in the intraocular space or cavity for assessing an intraocular disease or disorder in a subject. In still another example, the present method can comprise assessing microbiota in the intraocular space or cavity for assessing an intraocular disease or disorder in a subject. In some embodiments, a microbiota often refers to an "ecological community of commensal, symbiotic and/or pathogenic microorganism(s) found in and on a multicellular organism, e.g., a mammal or a human. A microbiota includes bacteria, archaea, protists, fungi and viruses. Some microbiota have been found to be crucial for immunologic, hormonal and metabolic homeostasis of their host. The synonymous term microbiome often describes either the collective genome(s) of the microorganism(s) that reside in an environmental niche or the microorganisms themselves.

The presence, absence, quantity, and other related parameters, e.g., infectious status or the microbiota of microorganism(s) can be assessed using any suitable techniques or procedures. For example, the presence, absence, quantity, and/or the infectious status of a microorganism, or the microbiota in the intraocular space can be assessed using a binding assay, e.g., an immunoassay. Any suitable immunoassay can be used. Exemplary immunoassays include an enzyme-linked immunosorbent assay (ELISA), immunoblotting, immunoprecipitation, radioimmunoassay (RIA), immunostaining, latex agglutination, indirect hemagglutination assay (DIA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

In another example, the presence, absence, quantity, and/or the infectious status of a microorganism, or the microbiota in the intraocular space or cavity can be assessed using a molecular assay. Any suitable molecular assay can be used. In some embodiments, the molecular assay uses a procedure that comprises isolating, amplifying, ligating, hybridizing and/or sequencing a polynucleotide of the microorganism. The polynucleotide of the microorganism can be amplified using any suitable technique or procedure. In some embodiments, the polynucleotide of the microorganism can be amplified using polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self-sustained sequence replication (3SR), or loop-mediated isothermal amplification (LAMP). The polynucleotide of the microorganism can be sequenced using any suitable technique or procedure. In some embodiments, the sequencing can be conducted using Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, or in vitro virus high-throughput sequencing.

In some embodiments, the molecular assay comprises sequencing analysis and/or PCR analysis. For example, the sequencing analysis comprises metagenomic sequencing analysis, e.g., metagenomic sequencing analysis of the microbiota. In another example, the PCR analysis comprises real-time PCR analysis, e.g., real-time PCR analysis of the microbiota.

The present method can comprise assessing microorganism(s) in any suitable intraocular space or cavity of a subject. For example, the present method can comprise assessing microorganism(s) in aqueous humor in anterior chamber, a suspensory ligament, ciliary body, ciliary body and muscle, vitreous humor in posterior chamber, retina, choroid, optic nerve, lens, or iris.

The present method can comprise assessing microorganism(s) in any suitable intraocular space or cavity of a subject in situ. Alternatively, the present method can comprise assessing the presence, absence, quantity, and/or the infectious status of a microorganism, or the microbiota using a sample isolated from an intraocular space or cavity of a subject. A sample can be isolated from any suitable intraocular space or cavity of a subject. For example, a sample can be isolated from aqueous humor in anterior chamber, a suspensory ligament, ciliary body, ciliary body and muscle, vitreous humor in posterior chamber, retina, choroid, optic nerve, lens, or iris of the subject.

The present method can be used for assessing an intraocular disease or disorder in any suitable subject. The subject can be a mammal, e.g., human or a non-human mammal. Exemplary non-human mammals include a mouse, a rat, a rabbit, a cat, a dog, a pig, a cow, an ox, a sheep, a goat, a horse, a monkey, or a non-human primate.

The present method can be used for assessing any suitable intraocular disease or disorder in a subject. Exemplary intraocular diseases or disorders include cataract (Cat), age-related macular degeneration (AMD), glaucoma (GLA), Betch's disease (BD), Vogt-Koyanagi-Harada Syndrome (VKH), and endophthalmitis (EOS).

In some embodiments, the present method comprises assessing the presence, absence, quantity, the infectious status, and/or the microbiota of one or more of the following *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti,* or *Acidovorax ebreus* in the intraocular space, cavity or sample of a subject for assessing Cat in the subject.

In some embodiments, the present method comprises the presence, absence, quantity, the infectious status, and/or the microbiota of one or more of the following *Staphylococcus epidermidis, Pseudomonas aeruginosa, Staphylococcus aureus, Staphylococcus haemolyticus, Pseudomonas putida,*

*Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* or *Xanthomonas oryzae* in the intraocular space, cavity or sample of a subject for assessing AMD in the subject.

In a preferred embodiment, the present method comprises assessing the presence, absence, quantity, the infectious status, and/or the microbiota of *Bacillus megaterium* for assessing AMD in the subject. *Bacillus megaterium* can be assessed using any suitable technique or procedure. For example, the present method comprises assessing live *Bacillus megaterium* for assessing AMD in the subject. In another example, *Bacillus megaterium* can be assessed using any suitable immunoassay or molecular assay. In a preferred embodiment, *Bacillus megaterium* can be assessed using sequencing analysis, e.g., metagenomic sequencing analysis of the microbiota, and/or PCR analysis, e.g., real-time PCR analysis of the microbiota. In still another example, *Bacillus megaterium* can be assessed using technique or procedure in the following Section F. For example, *Bacillus megaterium* can be assessed using one or more of the following primer pair(s): 1) SEQ ID NO:1, SEQ ID NO:2, (2) SEQ ID NO:3, SEQ ID NO:4, (3) SEQ ID NO:5, SEQ ID NO:6, (4) SEQ ID NO:7, SEQ ID NO:8, (5) SEQ ID NO:9, SEQ ID NO:10, (6) SEQ ID NO:11, SEQ ID NO:12, (7) SEQ ID NO:13, SEQ NO:14, (8) SEQ ID NO:15, SEQ ID NO:16, (9) SEQ ID NO:17, SEQ ID NO:18, (10) SEQ ID NO:19, SEQ ID NO:20, (11) SEQ ID NO:21, SEQ ID NO:22, (12) SEQ ID NO:23, SEQ ID NO:24, (13) SEQ ID NO:25, SEQ ID NO:26, (14) SEQ ID NO:27, SEQ ID NO:28, (15) SEQ ID NO:29, SEQ ID NO:30.

In some embodiments, the present method comprises assessing additional relevant parameters for assessing AMD in the subject. For example, the present method can further comprise assessing activation of complement system and/or induction of inflammation in the intraocular space, cavity or sample of a subject for assessing AMD in the subject.

In some embodiments, the present method comprises assessing the presence, absence, quantity, the infectious status, and/or the microbiota of one or more of the following *Acinetobacter baumannii, Acinetobacter calcoaceticus, Comamonas testosteroni, Mycobacterium kansasii, Bacillus thuringiensis, Citrobacter koseri, Dyadobacter fermentants, Serratia marcescens* in the intraocular space, cavity or sample of a subject for assessing GLA in the subject.

In some embodiments, the present method comprises assessing the presence, absence, quantity, the infectious status, and/or the microbiota of one or more of the following *Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D) in the intraocular space, cavity or sample of a subject for assessing BD in the subject.

In some embodiments, the present method comprises assessing the presence, absence, quantity, the infectious status, and/or the microbiota of one or more of the following *Escherichia coli, Micrococcus luteus, Bacillus subtilis, Corynebacterium aurimucosum, Finegoldia magna* in the intraocular space, cavity or sample of a subject for assessing VKH in the subject.

In some embodiments, the present method further comprises assessing clinical symptoms of an intraocular disease or disorder in a subject.

The present methods can be used for any suitable purposes. For example, the present methods can be used for risk assessment, diagnosis, prognosis, stratification and/or treatment monitoring of an intraocular disease or disorder in a subject. For example, the present methods can be used for assessing AMD of any suitable type or at any suitable stage, e.g., early AMD, intermediate AMD, late AMD, dry AMD, geographic atrophy (also called atrophic AMD), or wet AMD.

In some embodiments, the present method can further comprise preventing or treating an intraocular disease or disorder in a subject. In some embodiments, the present method can further comprise adjusting the prevention or treatment of the intraocular disease or disorder in the subject based on the assessment of the presence, absence, quantity, the infectious status, and/or the microbiota of the microorganism in the intraocular space, cavity or sample of a subject. For example, the present method can further comprise preventing or treating early AMD, intermediate AMD, late AMD, dry AMD, geographic atrophy (also called atrophic AMD), or wet AMD in a subject. The present method can further comprise adjusting the prevention or treatment of treating early AMD, intermediate AMD, late AMD, dry AMD, geographic atrophy (also called atrophic AMD), or wet AMD in the subject based on the assessment of the presence, absence, quantity, the infectious status, and/or the microbiota of the microorganism, e.g., *Bacillus megaterium*, in the intraocular space or sample of a subject.

D. Kits and Devices for Assessing an Intraocular Disease or Disorder

In another aspect, disclosed herein is a kit or device for assessing an intraocular disease or disorder in a subject, which kit or device comprises reagents for assessing the presence, absence, quantity, the infectious status, and/or the microbiota of a microorganism in an intraocular space, cavity or sample of a subject, wherein the etiology of said intraocular disease or disorder comprises infection of said microorganism in said intraocular space or cavity of said subject.

The present kit or device can comprise any suitable reagents. In some embodiments, the microorganism is a bacterium, a fungus, a virus, or a combination thereof, and the reagents of the present kit or device are configured for assessing the presence, absence, quantity, the infectious status, and/or the microbiota of said microorganism.

The present kit or device can comprise reagents for assessing any suitable number of microorganism(s) in the intraocular space or sample to assess an intraocular disease or disorder in a subject. For example, the present kit or device can comprise reagents for assessing the presence, absence, quantity, and/or the infectious status of a single microorganism in the intraocular space, cavity or sample for assessing an intraocular disease or disorder in a subject. In another example, the present kit or device can comprise reagents for assessing the presence, absence, quantity, and/or the infectious status of multiple microorganisms in the intraocular space, cavity or sample for assessing an intraocular disease or disorder in a subject. In still another example, the present kit or device can comprise reagents for assessing microbiota in the intraocular space, cavity or sample for assessing an intraocular disease or disorder in a subject.

The present kit or device can comprise reagents for assessing microorganism(s) in the intraocular space, cavity or sample using any suitable technique or procedure. For example, the present kit or device can comprise reagents to be used in a binding assay, e.g., an immunoassay. Any suitable immunoassay can be used. Exemplary immunoassays include an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

In another example, the present kit or device can comprise reagents to be used in a molecular assay. Any suitable molecular assay can be used. In some embodiments, the present kit or device can comprise reagents for isolating, amplifying, ligating, hybridizing and/or sequencing a polynucleotide of the microorganism. The polynucleotide of the microorganism can be amplified using any suitable technique or procedure. In some embodiments, the present kit or device can comprise reagents for amplifying the polynucleotide using polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self-sustained sequence replication (3 SR), or loop-mediated isothermal amplification (LAMP). The polynucleotide of the microorganism can be sequenced using any suitable technique or procedure. In some embodiments, the present kit or device can comprise reagents for polynucleotide sequencing that is conducted with a format selected from the group consisting of Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, and in vitro virus high-throughput sequencing.

In some embodiments, the present kit or device comprises reagents for sequencing analysis and/or PCR analysis. For example, the present kit or device can comprise reagents for metagenomic sequencing analysis, e.g., metagenomic sequencing analysis of the microbiota. In another example, the present kit or device can comprise reagents for real-time PCR analysis, e.g., real-time PCR analysis of the microbiota.

The present kit or device can further comprise additional tools. For example, the present kit or device can further comprise a tool for obtaining a sample from an intraocular space or cavity of a subject. The tool can be configured for obtaining a sample from any suitable intraocular space or cavity of a subject. For example, the tool can be configured for obtaining a sample from aqueous humor in anterior chamber, a suspensory ligament, ciliary body, ciliary body and muscle, vitreous humor in posterior chamber, retina, choroid, optic nerve, lens, or iris of a subject.

The present kit or device can comprise reagents for assessing any suitable intraocular disease or disorder in a subject. For example, the present kit or device can comprise reagents for assessing cataract (Cat), age-related macular degeneration (AMD), glaucoma (GLA), Betch's disease (BD), Vogt-Koyanagi-Harada Syndrome (VKH), or endophthalmitis (EOS) in a subject.

In some embodiments, the present kit or device comprises reagents for assessing the presence, absence, quantity, the infectious status, and/or the microbiota of one or more of the following *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti,* or *Acidovorax ebreus* in the intraocular space, cavity or sample of a subject for assessing Cat in the subject.

In some embodiments, the present kit or device comprises reagents for assessing the presence, absence, quantity, the infectious status, and/or the microbiota of one or more of the following *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* or *Xanthomonas oryzae* in the intraocular space, cavity or sample of a subject for assessing AMD in the subject.

In a preferred embodiment, the present kit or device comprises reagents for assessing the presence, absence, quantity, the infectious status, and/or the microbiota of *Bacillus megaterium* for assessing AMD in the subject. *Bacillus megaterium* can be assessed using any suitable technique or procedure. For example, the present kit or device comprises reagents for assessing live *Bacillus megaterium* for assessing AMD in the subject. In another example, the present kit or device comprises reagents for assessing *Bacillus megaterium* using any suitable immunoassay or molecular assay. In a preferred embodiment, the present kit or device comprises reagents for assessing *Bacillus megaterium* using sequencing analysis, e.g., metagenomic sequencing analysis of the microbiota, and/or PCR analysis, e.g., real-time PCR analysis of the microbiota. In still another example, *Bacillus megaterium* can be assessed using technique, procedure or kit in the following Section F. For example, the present kit or device comprises one or more of the following primer pair(s):1) SEQ ID NO:1, SEQ ID NO:2, (2) SEQ ID NO:3, SEQ ID NO:4, (3) SEQ ID NO:5, SEQ ID NO:6, (4) SEQ ID NO:7, SEQ ID NO:8, (5) SEQ ID NO: 9, SEQ ID NO:10, (6) SEQ ID NO:11, SEQ ID NO:12, (7) SEQ ID NO:13, SEQ NO:14, (8) SEQ ID NO:15, SEQ ID NO:16, (9) SEQ ID NO:17, SEQ ID NO:18, (10) SEQ ID NO:19, SEQ ID NO:20, (11) SEQ ID NO:21, SEQ ID NO:22, (12) SEQ ID NO:23, SEQ ID NO:24, (13) SEQ ID NO:25, SEQ ID NO:26, (14) SEQ ID NO:27, SEQ ID NO:28, (15) SEQ ID NO:29, SEQ ID NO:30 for assessing *Bacillus megaterium*.

In some embodiments, the present kit or device comprises a reagent for assessing additional relevant parameters for assessing AMD in the subject. For example, the present kit or device can further comprise a reagent for assessing activation of complement system and/or induction of inflammation in the intraocular space or sample of a subject for assessing AMD in the subject.

In some embodiments, the present kit or device comprises reagents for assessing the presence, absence, quantity, the infectious status, and/or the microbiota of one or more of the following *Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens* in the intraocular space, cavity or sample of a subject for assessing GLA in the subject.

In some embodiments, the present kit or device comprises reagents for assessing the presence, absence, quantity, the infectious status, and/or the microbiota of one or more of the following *Sphingomonas wittichii, Klebsiella pneumoniae, Pseudomonas fluorescens, Ralstonia pickettii, Lactobacillus*

*crispatus, Burkholderia multivorans, Lactobacillus delbrueckii, Meiothermus silvanus*(D) in the intraocular space, cavity or sample of a subject for assessing BD in the subject.

In some embodiments, the present kit or device comprises reagents for assessing the presence, absence, quantity, the infectious status, and/or the microbiota of one or more of the following *Escherichia coli, Micrococcus luteus, Bacillus subtilis, Corynebacterium aurimucosum, Finegoldia magna* in the intraocular space, cavity or sample of a subject for assessing VKH in the subject.

The present kit or device can also comprise additional means for assessing an intraocular disease or disorder in a subject. For example, the present kit or device can further comprise means, e.g., a reagent or structure, for assessing clinical symptoms of an intraocular disease or disorder in a subject.

The present kits or devices can be used for any suitable purposes. For example, the present kits or devices can be used for risk assessment, diagnosis, prognosis, stratification and/or treatment monitoring of an intraocular disease or disorder in a subject. For example, the present kits or devices can be used for risk assessment, diagnosis, prognosis, stratification and/or treatment monitoring of AMD of any suitable type or at any suitable stage, e.g., early AMD, intermediate AMD, late AMD, dry AMD, geographic atrophy (also called atrophic AMD), or wet AMD.

The present kits or devices can further comprise any suitable reagent. For example, the present kits or devices can further comprise a control reagent or a calibrator.

The present kit or device can further comprise means for treating or preventing the intraocular disease or disorder in the subject. For example, the present kit or device can further comprise means, e.g., a drug, a surgery tool or an implantable device, for treating or preventing the intraocular disease or disorder in the subject.

E. Methods for Treating and/or Preventing Intraocular Diseases or Disorders

In still another aspect, disclosed herein is a method for treating and/or preventing an intraocular disease or disorder in a subject, which method comprises administering, to a subject in need of such treatment and/or prevention, an effective amount of an agent that kills or inhibits a microorganism in an intraocular space or cavity of a subject, wherein the etiology of said intraocular disease or disorder comprises infection of said microorganism in said intraocular space or cavity of said subject.

The present methods can be used for any suitable purposes. For example, the methods can be used to treat an intraocular disease or disorder in a subject. In another example, the methods can be used to prevent an intraocular disease or disorder in a subject.

The present methods can be used for treating and/or preventing any suitable intraocular disease or disorder in a subject, wherein the etiology of the intraocular disease or disorder comprises infection of a microorganism in the intraocular space or cavity of the subject. The microorganism can be a bacterium, a fungus, a virus, or a combination thereof.

The present methods can be used for treating and/or preventing an intraocular disease or disorder in a subject, wherein the etiology of the intraocular disease or disorder comprises infection of any suitable number of microorganism(s) in the intraocular space or cavity of the subject. For example, the present methods can be used for treating and/or preventing an intraocular disease or disorder in a subject, wherein the etiology of the intraocular disease or disorder comprises infection of a single microorganism in the intraocular space or cavity of the subject and the agent kills or inhibits the single microorganism in the intraocular space or cavity of the subject. In another example, the present methods can be used for treating and/or preventing an intraocular disease or disorder in a subject, wherein the etiology of the intraocular disease or disorder comprises infection of multiple microorganisms in the intraocular space or cavity of the subject and the agent kills or inhibits the multiple microorganisms in the intraocular space or cavity of the subject. In still another example, the present methods can be used for treating and/or preventing an intraocular disease or disorder in a subject, wherein the etiology of the intraocular disease or disorder comprises a microbiota in the intraocular space or cavity of the subject and the agent kills or inhibits the microbiota in the intraocular space or cavity of the subject.

The present methods can use an agent that kills or inhibits a microorganism in any suitable intraocular space or cavity of the subject. For example, the present methods can use an agent that kills or inhibits a microorganism in aqueous humor in anterior chamber, a suspensory ligament, ciliary body, ciliary body and muscle, vitreous humor in posterior chamber, retina, choroid, optic nerve, lens, or iris of the subject.

The present methods can be used for treating and/or preventing an intraocular disease or disorder in any suitable subject. For example, the present methods can be used for treating and/or preventing an intraocular disease or disorder in a mammal. In some embodiments, the mammal is a non-human mammal, e.g., a mouse, a rat, a rabbit, a cat, a dog, a pig, a cow, an ox, a sheep, a goat, a horse, a monkey, or a non-human primate. In some embodiments, the mammal is a human. The subject or human can be at any suitable age. For example, a human patient can be at an age of at least, 10, 20, 30, 40, 50, 60, 70 or 80 years old.

The present methods can be used for treating and/or preventing any suitable intraocular disease or disorder in a subject. For example, the present methods can be used for treating and/or preventing cataract (Cat), age-related macular degeneration (AMD), glaucoma (GLA), Betch's disease (BD), Vogt-Koyanagi-Harada Syndrome (VKH), or endophthalmitis (EOS) in a subject.

In some embodiments, the present methods comprise administering, to a subject in need of such treatment and/or prevention, an effective amount of an agent that kills or inhibits one or more of the following *Pseudomonas mendocina, Kytococcus sedentarius, Alicycliphilus denitrificans, Achromobacter xylosoxidans, Sphingobium japonicum, Mycobacterium abscessus, Arthrobacter aurescens, Prevotella dentalis, Sinorhizobium meliloti,* or *Acidovorax ebreus* in an intraocular space or cavity of the subject to treat and/or prevent Cat in the subject.

In some embodiments, the present methods comprise administering, to a subject in need of such treatment and/or prevention, an effective amount of an agent that kills or inhibits one or more of the following *Staphylococcus epidermidis, Pseudomonas aeruginosa, Staphylococcus aureus, Staphylococcus haemolyticus, Pseudomonas putida, Stenotrophomonas maltophilia, Bacillus cereus, Bacillus megaterium, Lactobacillus reuteri, Gardnerella vaginalis, Enterococcus faecium, Cytophaga hutchinsonii, Bacillus licheniformis,* or *Xanthomonas oryzae* in an intraocular space or cavity of the subject to treat and/or prevent AMD in the subject. In a preferred embodiment, the present methods comprise administering, to a subject in need of such treatment and/or prevention, an effective amount of an agent that kills or inhibits *Bacillus megaterium* in an intraocular space or cavity of the subject to treat and/or prevent AMD in the subject.

In some embodiments, the present methods comprise administering, to a subject in need of such treatment and/or prevention, an effective amount of an agent that kills or inhibits one or more of the following *Acinetobacter baumannii, Acinetobacter calcoaceticus, Comamonas testosteroni, Mycobacterium kansasii, Bacillus thuringiensis, Citrobacter koseri, Dyadobacter fermentans, Serratia marcescens* in an intraocular space or cavity of the subject to treat and/or prevent GLA in the subject.

In some embodiments, the present methods comprise administering, to a subject in need of such treatment and/or prevention, an effective amount of an agent that kills or inhibits one or more of the following *Sphingomonas wittichii, Klebsiella pneumoniae, Pseudomonas fluorescens, Ralstonia pickettii, Lactobacillus crispatus, Burkholderia multivorans, Lactobacillus delbrueckii, Meiothermus silvanus*(D) in an intraocular space or cavity of the subject to treat and/or prevent BD in the subject.

In some embodiments, the present methods comprise administering, to a subject in need of such treatment and/or prevention, an effective amount of an agent that kills or inhibits one or more of the following *Escherichia coli, Micrococcus luteus, Bacillus subtilis, Corynebacterium aurimucosum, Finegoldia magna* in an intraocular space or cavity of the subject to treat and/or prevent VKH in the subject.

Any suitable agent can be used in the present methods. For example, the present methods can use an agent that kills a microorganism in an intraocular space or cavity of a subject. In another example, the present methods can use an agent that inhibits a microorganism in an intraocular space or cavity of a subject. In still another example, the present methods can use an agent that kills or inhibits a bacterium, a fungus, a virus, or a combination thereof, in an intraocular space or cavity of a subject.

In some embodiments, the agent comprises a small molecule drug, a chemical drug, a macromolecule drug, a biologic drug or a natural drug. Any suitable type of macromolecule drug or biologic drug can be used. For example, the macromolecule drug or biologic drug can comprise a polypeptide or a polynucleotide. The polypeptide can comprise an antibody or an antibody-drug conjugate.

In some embodiments, the agent can comprise an antimicrobial peptide. Any suitable antimicrobial peptide can be used. For example, the antimicrobial peptide can be an insect antimicrobial peptide, a mammalian antimicrobial peptide, an amphibian antibacterial peptide, an antibacterial peptide derived from fish, mollusc, or crustacean, a plant antibacterial peptide, a bacterial antibacterial peptide, or a combination thereof.

In some embodiments, the agent can comprise Calcined ancient ink, *Salvia* Miltiorrhiza, Arnebiaeuchroma, Radix *Isatidis, Houttuynia*, Honeysuckle, Rhizoma Coptis, Scutellaria, Dandelion, Purslane, Hawthorn, *Isatidis* Folium, Fructus Forsythiae, Herba Artemisiae *Capillaris*, Andrographis *Paniculata* Nees, Radix Bupleuri, Rhubarb, *Euphorbia Humifusa*, Stemonae, Garlic, Cortex Phellodendri, Eucommia, Cortex Fraxini, Fructus Cnidii, Galla *Chinensis*, viola yedoensis makino, Fructus Mume, Radix Glycyrrhizae, Pericarpium Granati, *Schisandra chinensis*, Spina Gleditsiae, Terminalia Chebula, *Sophora flavescens*, Cortex Pseudolaricis, Epimedium, *Artemisia apiacea* Hance, an extract thereof, or a combination thereof.

In some embodiments, the agent can comprise an antibiotic. Any suitable antibiotic can be used. For example, the antibiotic can be a β-lactam antibiotic, an aminoglycoside antibiotic, a tetracycline antibiotic, a chloramphenicol antibiotic, a macrolide antibiotic, a glycopeptide antibiotic, a quinolone antibiotic, a nitroimidazole antibiotic, a rifamycin antibiotic, an echinocandins antibiotic, a polyene antibiotic, a pyrimidine antibiotic, an allylamines antibiotic, or an azoles antibiotic, or a combination thereof.

In a specific embodiment, the present methods comprise administering, to a subject in need of such treatment and/or prevention, an effective amount of an antibiotic that kills or inhibits *Bacillus megaterium* in an intraocular space or cavity of the subject to treat and/or prevent AMD in the subject. Any suitable antibiotic can be used. For example, the antibiotic can be ampicillin, vancomycin, neomycin, tetracycline, or a combination thereof.

In some embodiments, the present methods further comprise administering, to a subject in need of such treatment and/or prevention, an effective amount of a second agent for treating and/or preventing an intraocular disease or disorder in the subject. Any suitable second agent can be used. For example, a second agent that inhibits activation of complement system and/or induction of inflammation in the intraocular space or cavity can be used for treating and/or preventing AMD in the subject.

In some embodiments, the present methods further comprise administering a pharmaceutically acceptable carrier or excipient to the subject.

The agent and/or the pharmaceutically acceptable carrier or excipient can be administered to a subject using any suitable manner or route. For example, the agent and/or the pharmaceutically acceptable carrier or excipient can be administered to a subject orally, parenterally, by inhalation, topically, rectally, nasally, buccally, vaginally, via an implanted reservoir, or other drug administration methods. In another example, the agent and/or the pharmaceutically acceptable carrier or excipient can be administered to an intraocular space or cavity of a subject.

In some embodiments, the agent and/or the pharmaceutically acceptable carrier or excipient can be administered through topical, local ocular (e.g., subconjunctival, intravitreal, retrobulbar, intracameral), or systemic route. The method of administration often depends on the area of the eye to be medicated. For example, the conjunctiva, cornea, anterior chamber, and iris usually respond well to topical delivery. The posterior segment often requires systemic administration, or intravitreal, retrobulbar, or intracameral administration.

In yet another aspect, disclosed herein is an effective amount of an agent that kills or inhibits a microorganism in an intraocular space or cavity of a subject for the manufacture of a medicament for treating or preventing an intraocular disease or disorder in the subject, wherein the etiology of said intraocular disease or disorder comprises infection of said microorganism in said intraocular space or cavity of said subject.

In yet another aspect, disclosed herein is a combination, which combination comprises an effective amount of an agent that kills or inhibits a microorganism in an intraocular space or cavity of a subject and an effective amount of a second agent for treating and/or preventing an intraocular disease or disorder, wherein the etiology of said intraocular disease or disorder comprises infection of said microorganism in said intraocular space or cavity of said subject.

In yet another aspect, disclosed herein is a method for treating and/or preventing an intraocular disease or disorder in a subject, which method comprises administering, to a subject in need of such treatment and/or prevention, an effective amount of the above-described combination, wherein the etiology of said intraocular disease or disorder comprises infection of said microorganism in said intraocular space or cavity of said subject.

In yet another aspect, disclosed herein is use of the above-described combination for the manufacture of a medicament for treating or preventing an intraocular disease or disorder in a subject, wherein the etiology of said intraocular disease or disorder comprises infection of said microorganism in an intraocular space or cavity of said subject.

Formulations

Any suitable formulation of an agent that kills or inhibits a microorganism described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated agents are administered in a pharmacological composition, it is contemplated that the agents can be formulated in admixture with a pharmaceutically acceptable excipient and/or carrier. For example, contemplated agents can be administered orally as neutral agents or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated agents may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular agent in order to manage the pharmacokinetics of the present agent for maximum beneficial effect in a patient.

In some embodiments, agents as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. The pharmaceutical compositions thus obtained are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the agents may be modified to render them more soluble in water or another vehicle. It is also well within the ordinary skill of the art to modify the route of administration and dosage regimen of a particular agent in order to manage the pharmacokinetics of the agent for maximum beneficial effect in a patient.

Drug Combinations

The methods of the embodiments comprise administering an effective amount of at least one exemplary agent of the present disclosure; optionally the agent may be administered in combination with one or more additional therapeutic agents, particularly therapeutic agents known to be useful for treating and/or preventing an intraocular disease or disorder in a subject.

The additional active ingredients may be administered in a separate pharmaceutical composition from at least one exemplary agent of the present disclosure or may be included with at least one exemplary agent of the present disclosure in a single pharmaceutical composition. The additional active ingredients may be administered simultaneously with, prior to, or after administration of at least one exemplary agent of the present disclosure.

Methods of Using the Exemplary Agents and Pharmaceutical Compositions Thereof

To practice the method of the present disclosure, agents that kill or inhibit a microorganism and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

F. Exemplary Disclosure

In exemplary embodiments, the present disclosure belongs to the technical field of diagnosis and treatment of ophthalmic diseases, and particularly relates to a method for the detection of microbiota causing ophthalmic diseases and a medicine for the treatment of the diseases.

It has long been known that the intraocular cavity is absolutely sterile under healthy conditions, because tears and blinks can remove foreign bodies such as microbiota. However, recent studies have also found that even normal healthy eyes have microbiotas. Some of these microbiotas are symbiotic bacteria, while others are pathogenic bacteria.

Age-related macular degeneration (AMD), which can be divided into dry AMD and wet AMD, is an aging change of the macular structure and the leading cause of irreversible vision loss in the elderly.

Dry AMD is due to the long-term chronic progressive atrophy of the RPE-Bruch membrane-choroidal capillary complex. Dry AMD occurs mostly in the elderly over the age of 50. The visual acuity of the bilateral eyes declines symmetrically and extremely slow, and patients often have symptoms such as visual distortion. Fundus examination shows the pigmentation disorder of the macula in the eyes, the disappearance of the foveal light reflex, and sometimes the yellow-white drusen with different sizes and unclear borders in the posterior pole. In the late stage of the disease, due to the atrophy and pigmentation loss of RPE (retinal pigment epithelium (RPE), it can be seen that there is a geographic atrophy zone with relatively clear border in the posterior pole of the retina in some patients. If the choroidal capillaries also get shrink, some thick choroidal blood vessels can be seen in the atrophy zone.

Wet AMD is due to the formation of the choroidal neovascularization (CNV), which is induced by the damage of the Bruch membrane and the growth of choroidal capillaries to the retinal pigment epithelium and retinal nerve epithelium through the lesion of Bruch membrane. Once the CNV is formed, due to the imperfect structure of the new blood vessels, a series of pathological changes such as exudation, hemorrhage, mechanization and scarring appear, and the central vision will lose to be exhausted eventually.

With the increase of age, the phagocytic function of the retinal pigment epithelium declines, therefor, the photoreceptor extracellular disc cannot be completely digested. The residual metabolites continuously discharge from the RPE cells and deposit on the glass membrane to form a drusen.

The drusen is divided into four categories: hard, soft, mixed and degraded drusen. The drusen can be found in the elderly with normal vision. The increase in the number of drusen, the increase in pigment, and the increase in fusion are the characteristics that drusen has risk factors. The accumulation of drusen on the vitreous membrane has an impact on the retina's absorption of nutrients and oxygen through the choroidal vessels, and also destroys the integrity of Bruch's membrane. When the retina is hypoxic or ischemic, it will induce to the up-regulation of vascular endothelial growth factor (VEGF), integrin and protease. When VEGF signal is stronger than pigment epithelium derived factor (PEDF), it will enhance the angiogenesis and stimulate the growth of new blood vessels. Increased expression of VEGF and rupture of Bruch's membrane ultimately lead to the formation of CNV, which in turn causes exudation, hemorrhage and scar formation.

In the past 10 years, the diversity and function of microbiota associated with human health and diseases have been extensively studied through high-throughput sequencing technologies and macrobiotic/metagenomic analysis. The local microbiota of the eye under physiological and pathological conditions remains largely uncharacterized. The theory that the intraocular cavity is absolutely sterile under physiological conditions has led many researchers to reason that any types of foreign organisms are exogenous and pathogenic. However, the present disclosure indicates that even normal healthy eyes with no signs of ocular distress or infection have an individualized microbiota with compositional and functional diversity distinct from other body sites and tissues. Interestingly, the fact that *P. acnes* lives in the majority of human eyes and does not significantly induce intraocular inflammation raises a reasonable hypothesis that the normal intraocular microbiota plays a key role in maintaining the homeostasis of the local ocular environment. Similarly, the dysbiosis of the local microbial community can contribute to the etiology of many infectious, inflammatory, neoplastic, and degenerative ocular diseases. In addition, the idea that culture-positive microbiota such as *P.*

*acnes* were the major causes of intraocular inflammation warrants reexamination since these microbiota may be part of the intraocular commensal flora while the real pathogens were unexpected and missed. Many ocular procedures such as surgeries and intravitreal injection of anti-VEGF agents may also trigger the exposure of pathogenic intraocular microbiota to host immune system. Therefore, future studies are needed to clearly define the association of intraocular microbiota with integrity of ocular health.

Genetic studies have successfully identified various factors involved in the pathogenesis of AMD. These factors all suggest that the activation of complement cascade and controlling of immune responses are the keys for AMD onset and progress. However, the initiator of AMD pathology (especially how drusen is formed) and the critical link between complement and AMD pathology have been unclear.

The existing technology doesn't clearly clarify the cause of age-related macular degeneration. The diagnosis can only be based on the patient's symptoms. No definitive basis can help the doctor make an accurate judgment, which may lead to misdiagnosis or delay the best time for treatment. In the existing technology, vitrectomy is commonly used to treat age-related macular degeneration, however the improvement of visual acuity after surgery is very limited. Sometimes multiple operations are required to maintain the patient's weak vision and eyeballs. Some patients still have no treatment effect even after multiple operations.

To overcome the deficiencies of the existing technology, the present disclosure provides a method for the detection of age-related macular degeneration and a medicine for the treatment of age-related macular degeneration.

The first aspect of the present disclosure provides a method for the detection of intraocular microbiota, and the microbiota is selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*. The method is to detect the microbiota using metagenomic sequencing analysis, and/or real-time PCR analysis.

Preferably, the steps of the detecting method are as follows:

(1) Taking retinal tissue and extracting DNA from retinal tissue;

(2) Detecting DNA in the retinal tissue using metagenomic sequencing analysis and/or real-time PCR analysis so as to detect one or more microbiota in the retina, and the microbiota is selected from one or more of the following microbiota: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

Further, the step (1) of the method for the detection of intraocular microbes includes the following steps:

1) Irrigation of the patient's conjunctival sac;
2) Mydriasis of the patient's eyes;
3) Disinfection of the patient's eyes;
4) Sterilizing the patient's conjunctival sac;
5) Taking retinal tissue and extracting DNA from retinal tissue.

Much further, the step (1) of the method for the detection of intraocular microbes includes the following steps:

1) Irrigating patients' conjunctival sac using 0.9% sodium chloride solution for 2 to 5 times;

2) Mydriasis of the patient's eyes with the medicine selected from one or two of the followings: a compound tropicamide solution, an atropine eye ointment, an atropine solution, a homatropine solution, a homatropine eye ointment, a tropicamide solution, a catopine solution, a phenylephrine solution and a scopolamine solution;

3) Disinfecting the patient's eyes with the medicine selected from one or two of the followings: povidone iodine solution, levofloxacin hydrochloride ophthalmic gel, ofloxacin solution, levofloxacin hydrochloride solution, tobramycin dexamethasone eye ointment, tobramycin dexamethasone solution and compound sulfate neomycin solution for 15 to 45 seconds;

4) Sterilizing the patient's conjunctival sac with the medicine selected from one or two of the followings: tobramycin solution, lomefloxacin hydrochloride solution and ofloxacin solution, and infuse 2 to 5 times;

5) Taking retinal tissue and extracting DNA from retinal tissue.

Preferably, the method for the detection of intraocular microbiota in the present disclosure may be for diagnostic or non-diagnostic purposes.

The second aspect of the present disclosure provides a method for the diagnosis of age-related macular degeneration using metagenomic sequencing analysis and/or real-time PCR analysis, so as to detect intraocular microbiota selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

Preferably, the method for the diagnosis of age-related macular degeneration in the present disclosure is as follows:

(1) Taking retinal tissue and extracting DNA from retinal tissue;

(2) Detecting DNA in the retinal tissue using metagenomic sequencing analysis and/or real-time PCR analysis, so as to detect one or more of the following microbiota in the retinal tissue: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

Further, the step (1) of the method for the diagnosis of age-related macular degeneration includes the following steps:

1) Irrigation of the patient's conjunctival sac;
2) Mydriasis of the patient's eyes;
3) Disinfecting the patient's eyes;
4) Sterilizing the patient's conjunctival sac;
5) Taking retinal tissue and extracting DNA from retinal tissue.

Much further, the step (1) of the method for the diagnosis of age-related macular degeneration includes the following steps:

1) Irrigating patients' conjunctival sac using 0.9% sodium chloride solution for 2 to 5 times;

2) Mydriasis of the patient's eyes with the medicine selected from one or two of the followings: a compound tropicamide solution, an atropine eye ointment, an atropine solution, a homatropine solution, a homatropine eye ointment, a tropicamide solution, a catopine solution, a phenylephrine solution and a scopolamine solution;

3) Disinfecting the patient's eyes with the medicine selected from one or two of the followings: povidone iodine solution, levofloxacin hydrochloride ophthalmic gel, ofloxacin solution, levofloxacin hydrochloride solution, tobramycin dexamethasone eye ointment, tobramycin dexamethasone solution and compound sulfate neomycin solution for 15 to 45 seconds;

4) Sterilizing the patient's conjunctival sac with the medicine selected from one or two of the followings: tobramycin solution, lomefloxacin hydrochloride solution and ofloxacin solution, and infuse 2 to 5 times;

5) Taking retinal tissue and extracting DNA from retinal tissue.

Preferably, the method for the diagnosis of age-related macular degeneration in the present disclosure is used to diagnose dry or wet age-related macular degeneration, and more preferably, the method for the diagnosis of age-related macular degeneration is to diagnose dry or wet age-related macular degeneration with drusen symptoms, including a hard drusen, a soft drusen, a mixed drusen and a degraded drusen, and particularly preferably, the method for the diagnosis of age-related macular degeneration is to diagnose dry or wet age-related macular degeneration with soft drusen symptoms.

The present disclosure also provides the following primer pairs for preparing a age-related macular degeneration diagnostic kit: (1) SEQ ID NO:1, SEQ ID NO:2, and/or, (2) SEQ ID NO:3, SEQ ID NO:4, and/or, (3) SEQ ID NO: 5, SEQ ID NO:6, and/or, (4) SEQ ID NO:7, SEQ ID NO:8, and/or, (5) SEQ ID NO:9, SEQ ID NO:10, and/or, (6) SEQ ID NO:11, SEQ ID NO:12, and/or, (7) SEQ ID NO:13, SEQ ID NO:14, and/or, (8) SEQ ID NO:15, SEQ ID NO:16, and/or, (9) SEQ ID NO:17, SEQ ID NO:18, and/or, (10) SEQ ID NO:19, SEQ ID NO:20, and/or, (11) SEQ ID NO:21, SEQ ID NO:22, and/or, (12) SEQ ID NO: 23, SEQ ID NO: 24, and/or, (13) SEQ ID NO:25, SEQ ID NO: 26, and/or, (14) SEQ ID NO: 27, SEQ ID NO: 28, and/or, (15) SEQ ID NO:29, SEQ ID NO:30.

The present disclosure also provides a kit for diagnosing age-related macular degeneration, which is capable of detecting the abundance of microbiota by real-time PCR analysis, so as to diagnose age-related macular degeneration.

In the specific implement way of the present disclosure, a kit for the diagnosis of age-related macular degeneration includes: (1) SYBR Green I; (2) Taq enzyme; (3) primer pairs1): SEQ ID NO:1, SEQ ID NO:2, and/or primer pairs2): SEQ ID NO:3, SEQ ID NO:4, and/or primer pairs3) SEQ ID NO:5, SEQ ID NO:6, and/or primer pairs4) SEQ ID NO:7, SEQ ID NO:8, and/or, primer pairs5) SEQ ID NO:9, SEQ ID NO:10, and/or, primer pairs6) SEQ ID NO:11, SEQ ID NO:12, and/or, primer pairs7) SEQ ID NO:13, SEQ ID NO:14, and/or, primer pairs8) SEQ ID NO:15, SEQ ID NO:16, and/or, primer pairs9) SEQ ID NO:17, SEQ ID NO:18, and/or, primer pairs10) SEQ ID NO:19, SEQ ID NO:20, and/or, primer pairs11) SEQ ID NO:21, SEQ ID NO:22, and/or, primer pairs12) SEQ ID NO:23, SEQ ID NO:24, and/or, primer pairs13) SEQ ID NO:25, SEQ ID NO:26, and/or, primer pairs14) SEQ ID NO:27, SEQ ID NO:28, and/or, primer pairs15) SEQ ID NO:29, SEQ ID NO:30; (4) dNTP; (5) buffer; (6) sterilized water.

The kit of the present disclosure comprises: (1) mix; (2) primer pairs1): SEQ ID NO:1, SEQ ID NO:2, and/or, primer pairs2): SEQ ID NO:3, SEQ ID NO:4, and/or, primer pairs3) SEQ ID NO:5, SEQ ID NO:6, and/or, primer pairs4) SEQ ID NO:7, SEQ ID NO:8, and/or, primer pairs5) SEQ ID NO:9, SEQ ID NO:10, and/or, primer pairs6) SEQ ID NO:11, SEQ ID NO:12, and/or, primer pairs7) SEQ ID NO:13, SEQ ID NO:14, and/or, primer pairs8) SEQ ID NO:15, SEQ ID NO:16, and/or, primer pairs9) SEQ ID NO:17, SEQ ID NO:18, and/or, primer pairs10) SEQ ID NO:19, SEQ ID NO:20, and/or, primer pairs11) SEQ ID NO:21, SEQ ID NO:22, and/or, primer pairs12) SEQ ID NO:23, SEQ ID NO:24, and/or, primer pairs13) SEQ ID NO:25, SEQ ID NO:26, and/or, primer pairs14) SEQ ID NO:27, SEQ ID NO:28, and/or, primer pairs15) SEQ ID NO:29, SEQ ID NO:30; (3) sterilized water, the mix in the kit contains SYBR GreenI, Taq enzyme, dNTP, buffer.

Preferably, the method for the diagnosis of age-related macular degeneration in the present disclosure is used to diagnose dry or wet age-related macular degeneration, and more preferably, the method for the diagnosis of age-related macular degeneration is to diagnose dry or wet age-related macular degeneration with drusen symptoms, including a hard drusen, a soft drusen, a mixed drusen and a degraded drusen, and particularly preferably, the method for the diagnosis of age-related macular degeneration is to diagnose dry or wet age-related macular degeneration with soft drusen symptoms.

The present disclosure provides a medicine, which is used to kill or inhibit microbiota, and the microbiota is selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

Killing in the present disclosure means killing pathogenic microbiota.

Inhibition in the present disclosure means inhibiting the growth and reproduction of microbiota.

The preferred medicine in the present disclosure is the medicine used to kill or inhibit microbiota, and the microbiota is selected from one or more of the followings: *Propionibacterium acnes, Bacillus megaterium, Bacillus licheniformis, Pseudomonas putida, Xanthomonas oryzae, Stenotrophomonas maltophilia, Lactobacillus reuteri, Staphylococcus haemolyticus, Cytophaga hutchinsonii, Gardnerella vaginalis, Staphylococcus aureus, Pseudomonas aeruginosa, Bacillus cereus, Staphylococcus epidermidis* and *Enterococcus faecium*.

The medicine in the present disclosure is selected from one of the following drugs: chemical drugs, biologic drugs or natural drugs.

The medicine in the present disclosure is a single component or a composition.

The chemical drug in the present disclosure is selected from one or more of the followings: β-lactam antibiotics, including penicillins, cephalosporins, thienamycins, monobactams, β-lactamase inhibitors, methoxypenicillins, etc.; Aminoglycoside antibiotics: including streptomycin, gentamicin, kanamycin, tobramycin, amikacin, neomycin, ribomycin, micronomicin, azithromycin, etc.; Tetracycline antibiotics: including tetracycline, oxytetracycline, chlortetracycline and doxycycline; chloramphenicol antibiotics: including chloramphenicol, thiamphenicol, etc.; macrolide antibiotics: including erythromycin, leucomycin, odorless erythromycin, acetylspiramycin, medimycin, josamycin, azithromycin, etc.; glycopeptide antibiotics: including vancomycin, norvancomycin, teicoplanin, etc.; quinolone antibiotics: including norfloxacin, ofloxacin, ciprofloxacin, pefloxacin, gatifloxacin; nitroimidazole antibiotics: including metronidazole, tinidazole, ornidazole, etc.; rifamycinoid antibiotics: including rifampicin; echinocandin antibiotics; polyene antibiotics; pyrimidines antibiotics; allylamine antibiotics; azole antibiotics; other antibiotics: fosfomycin, capreomycin, cycloserine, lincomycin, clindamycin, mitomycin, actinomycin D, bleomycin, doxorubicin, isoniazid, pyrazinamide, cyclosporine, etc.

The biological drug in the present disclosure is an antibacterial peptide selected from one or more of the followings: insect antibacterial peptides, for example, lepidopteran antibacterial peptide, diptera antibacterial peptide, coleoptera antibacterial peptide, odonata antibacterial peptide, hymenoptera antibacterial Peptide, silkworm antibacterial peptide, etc.; mammalian antibacterial peptides, for example, porcine antibacterial peptide, sheep antibacterial peptide, bovine antibacterial peptide, human antibacterial peptide, etc.; amphibian antibacterial peptides: *xenopus*, etc.; antibacterial peptides from fish, mollusks, crustaceans: *Pardachirus pavoninus* antibacterial peptide, *Parasilurus asotus* antibacterial peptide, mussel antibacterial peptide, shrimp antibacterial peptide, etc.; plant antibacterial peptide: Thi-onins, etc., bacterial antibacterial peptide: bacitracin, gramicidin, polymyxin and nisin.

The natural drug in the present disclosure is selected from one or more of the followings: Calcined ancient ink, *Salvia miltiorrhiza*, Arnebiaeuchroma, Radix *Isatidis, Houttuynia*, Honeysuckle, Rhizoma Coptis, Scutellaria, Dandelion, Purslane, Hawthorn, *Isatidis* Folium, Fructus Forsythiae, Herba Artemisiae *Capillaris*, Andrographis *Paniculata* Nees, *Radix Bupleuri*, Rhubarb, *Euphorbia Humifusa*, Stemonae, Garlic, Cortex Phellodendri, Eucommia, Cortex Fraxini, Fructus Cnidii, Galla *Chinensis*, viola yedoensis makino, Fructus Mume, Radix Glycyrrhizae, Pericarpium Granati, *Schisandra chinensis, Spina Gleditsiae, Terminalia Chebula, Sophora flavescens*, Cortex Pseudolaricis, Epimedium, *Artemisia apiacea* Hance or extracts thereof.

The medicine in the present disclosure is oral, injectable or topical medicine which includes mucosal drug, preferably ocular drug.

The medicine in the present disclosure is in the form of a solution, a tablet, a pill, a capsule, an injection, a powder, a powder for injection, a patch, a coating agent or a mucosal administration preparation preferably for eye drops, eye ointments or eye spray preparations, etc.

The present disclosure also provides the application of medicines killing or inhibiting microbiota on preparing the medicines for the treatment of age-related macular degeneration, preferably, the method for the diagnosis of age-related macular degeneration in the present invention is used to diagnose dry or wet age-related macular degeneration, and more preferably, the method for the diagnosis of age-related macular degeneration is to diagnose dry or wet age-related macular degeneration with drusen symptoms, including a hard drusen, a soft drusen, a mixed drusen and a degraded drusen, and particularly preferably, the method for the diagnosis of age-related macular degeneration is to diagnose dry or wet age-related macular degeneration with soft drusen symptoms.

The present disclosure finds that all human eyes we tested have intraocular microbiota, we next investigated whether a disease-specific intraocular microbiota could characterize ocular manifestations. We carried out metagenomic sequencing analysis on aqueous humor specimens from 41 cataract (Cat), 20 AMD, 18 glaucoma (GLA), 9 Betch's disease (BD), 9 Vogt-Koyanagi-Harada Syndrome (VKH), and 8 endophthalmitis (EOS) patients. Interestingly, the alpha diversity and evenness of the intraocular microbial communities were significantly different among these 6 types of patients, despite all patients having bacteria as the major component of their intraocular microbiome. The principal component analysis (PCA) on the composition of the intraocular microbiota (using all microbial species) showed clear differences among cataract, EOS, and some glaucoma patients. However, AMD, VKH, BD, and some glaucoma patients shared indistinguishable features in their intraocular microbiome. Similarly, hierarchical clustering analysis of the abundance of functional microbial genes from all metagenomes indicated that each ocular manifestation had a general signature of microbial function, while there were outliers in every disease group that could be classified to other disease clusters. In spite of the significant individuality presented by the intraocular microbiome, we were able to identify the signature bacterial species for each ocular disease group we tested. Taken together, our results suggest that the composition and function of intraocular microbiota can differentiate ocular diseases such as AMD, cataract, glaucoma, BD, VKH, and EOS.

The present disclosure identified 14 bacterial species that were highly enriched in the AH of AMD patients using metagenomic analysis. While *P. acnes* was the most abundant microorganism in the AH of AMD patients, *Bacillus licheniformis* (*B. licheniformis*) and *Bacillus megaterium* (*B. megaterium*) were the most enriched species, among the 14 AMD-specific ones, in AMD AH specimens. The present disclosure then carried out PCR analysis to investigate whether the 14 AMD-specific bacteria could be detected in the hard or soft drusen tissues, as compared to the non-drusen retinal tissues from 6 archived ocular slides of AMD patients. Our results showed only 8 bacteria could be detected, among which *P. acnes* was the most abundant species and *B. megaterium* was the only species enriched in soft drusen. The relative abundance of *P. acnes* was comparable in hard drusen, soft drusen, and dry AMD lesion tissues as compared to the non-drusen non-lesion retinal tissues. The relative abundance of *B. megaterium* was elevated by ~18 fold in soft drusen but not the AMD lesions when compared to the non-drusen/non-lesion tissues. These data suggest a possible role of *B. megaterium* in drusen formation and AMD pathogenesis.

Previous studies demonstrate that drusen contains a variety of complement components and polysaccharides in addition to many other proteins. In addition, the drusen components activate inflammasomes and promote expression of IL-1 and IL-18. The present disclosure therefore first examined whether *B. megaterium*, as a component of drusen, was able to induce the activation of complement system and promote the secretion of IL-1 and IL-18, by acute retinal pigment epitheliitis-19(ARPE19) cells in vitro. We found *B. megaterium* but not *P. acnes* significantly increased the pyroptosis of RPE cells in a time dependent manner. The activation of complement system was confirmed by the production of active form of C5A protein. Both bacteria induced secretion of CFH proteins secreted by ARPE19 cell, while the induction of CFH was more profound by *B. megaterium* than by *P. acnes*. As the result of pyroptosis, in vitro infection of *B. megaterium*, but not *P. acnes*, led to secretion of active IL-1 and IL-18 by RPE cells.

These results indicate that infection of *B. megaterium* can lead to inflammation similarly found in soft drusen.

The present disclosure next tested whether *B. megaterium* was able to induce inflammation in vivo. We chose the non-human primate macaque (*Macaca fascicularis*) as our model system considering the ocular anatomy and intraocular environment shared by human and macaque. Infection of live *P. acnes* bacterium or inoculation of its sonication-inactivated proteins into the eye, as well as live *B. licheniformis* bacterium or inoculation of its sonication-inactivated proteins into the eye did not induce significant intraocular inflammation. However, infection of live *B. megaterium* but not its proteins into the eye led to a profound intraocular inflammation. The intraocular inflammation induced by live *B. megaterium* was characterized by the elevation of TNFA and IL6 but not IFNG and IL17A expression. Importantly, only live *B. megaterium* was able to activate complement system including C5A and CFH and induce pyroptotic cytokines IL-1 and IL-18 in vivo. The bacteria remained alive in the eyes after inflammation was initiated, suggesting the intraocular inflammation may be long lasting in nature. Taken together, our data demonstrate that infection of *B. megaterium* can activate complement system and induce pyroptosis of ocular cells in vitro and in vivo.

The present disclosure indicates that bacteria such as *B. megaterium* located in drusen and activated local complement-mediated immune response can explain the formation of diversified drusen between RPE and Bruch's membrane. The major proteins found in drusen including complement components such as CIO and immunoglobulin are all first line of anti-infectious agents. Other drusen proteins such as vitronectin and Apolipoprotein E are all recently proved as anti-infectious agents. Therefore, the formation of drusen is very possible the key response of the aging retina in controlling infiltrated bacterial pathogens. Due to the diversity of bacteria, the shape and size of drusen could vary. In the case of hard drusen, where the infection may be cleared, drusen will disappear. However, certain pathogens such as *B. megaterium* will induce long term activation of immune responses in soft drusen and result in the damage of RPE cells and photoreceptors. Activation of the inflammation of macrophage and pyroptosis of RPE cells are protective responses against local infection, which is consistent with the previous finding that NLRP3 mediated inflammasome activation and IL-18 production protect the retina from neovascularization.

The infectious etiology of AMD is also consistent with the conclusions reached by all genetic studies. For example, a defective CFH, the negative regulator of complement activation induced by *B. megaterium* infection, will result in uncontrolled complement activation. A defective HTRA1, the protease producing the active form of immunosuppressive cytokine TGF-, will result in decrease of local TGF-family proteins. Both of these genetic variations can lead to dysregulation of local anti-infectious responses that damages RPE cells and photoreceptors.

In addition, the potential difference in pathogenic microbiota found in drusen may explain the association of varied genetic risk factors with different ethnic groups (i.e. Caucasian vs Asian). Therefore, based on our data, the infectious etiology of AMD is a plausible mechanism by which early AMD pathology is initiated in the elderly. In summary, the present disclosure provides a novel target for the diagnosis, treatment, and prevention of AMD.

The present disclosure designs and synthesizes universal primers for pathogenic microbiota DNA according to the conserved genomic DNA sequence of common pathogenic microbiota of age-related macular degeneration, and detects pathogenic microbiota by real-time PCR, so as to realize the efficient and accurate detection of pathogenic microbiota of age-related macular degeneration, which help doctors make quick and accurate judgments during the disease diagnosis. And the medicine provided by the present disclosure is prepared based on the cause of age-related macular degeneration and can effectively treat age-related macular degeneration.

EXAMPLES

Example 1

A kit for the detection of *Propionibacterium acnes* contains (1) SYBR GreenI; (2) Taq enzyme; (3) primer pairs SEQ ID NO:1 GATTGGTTTACTACCCGTGAGCG, SEQ ID NO:2 ATAGCAGGGATTCCAGCGACA; (4) dNTP; (5) buffer; (6) sterilized water. The kit is applied on the detection of *Propionibacterium acnes* in the eyes using real-time PCR method.

Example 2

A kit for the detection of *Bacillus megaterium* contains (1) SYBR Green I; (2) Taq enzyme; (3) primer pairs SEQ ID NO:3 GGTTCAATGAGCCTACT, SEQ ID NO:4 GCCAGCGTCTTTCC; (4) dNTP; (5) buffer; (6) sterilized water. The kit is applied on the detection of *Bacillus megaterium* in the eyes using real-time PCR method.

Example 3

A kit for the detection of *Bacillus licheniformis* contains (1) SYBR Green I; (2) Taq enzyme; (3) primer pairs SEQ ID NO:5 TCCCGTCTTCATCTACTGC, SEQ ID NO:6 GGACGCCTACTGGACAA; (4) dNTP; (5) buffer; (6) sterilized water. The kit is applied on the detection of *Bacillus licheniformis* in the eyes using real-time PCR method.

Example 4

A kit for the detection of *Pseudomonas putida* contains (1) SYBR Green I; (2) Taq enzyme; (3) primer pairs SEQ ID NO:7 CCGCACAGGTTGTCCCA, SEQ ID NO:8 CTGCTGCGTTGTCGTTCC; (4) dNTP; (5) buffer; (6) sterilized water. The kit is applied on the detection of *Pseudomonas putida* in the eyes using real-time PCR method.

Example 5

A kit for the detection of *Xanthomonas oryzae* contains (1) SYBR Green I; (2) Taq enzyme; (3) primer pairs SEQ ID NO:9 TGGTGCGATGGCGATGTT, SEQ ID NO:10 GGTTGCGGCATGTGCTTT; (4) dNTP; (5) buffer; (6) sterilized water. The kit is applied on the detection of *Xanthomonas oryzae* in the eyes using real-time PCR method.

Example 6

A kit for the detection of *Stenotrophomonas maltophilia* contains (1) SYBR Green I; (2) Taq enzyme; (3) primer pairs SEQ ID NO:11 GCGTTCGTCCGCTGTCA, SEQ ID NO:12 GGCAACCCGCTAGAATCCC; (4) dNTP; (5) buffer; (6) sterilized water. The kit is applied on the detection of *Stenotrophomonas maltophilia* in the eyes using real-time PCR method.

Example 7

A kit for the detection of *Lactobacillus reuteri* contains (1) SYBR Green I; (2) Taq enzyme; (3) primer pairs SEQ ID NO:13 TAGTGGATAATGCCGTTGA, SEQ ID NO:14 CGGTTTGCCAGAAGC; (4) dNTP; (5) buffer; (6) sterilized water. The kit is applied on the detection of *Lactobacillus reuteri* in the eyes using real-time PCR method.

Example 8

A kit for the detection of *Staphylococcus haemolyticus* contains (1) SYBR Green I; (2) Taq enzyme; (3) primer pairs SEQ ID NO:15 GTTACACTGCTCCGACAA, SEQ ID NO:16 TTCGCATCAGCAATAA; (4) dNTP; (5) buffer; (6) sterilized water. The kit is applied on the detection of *Staphylococcus haemolyticus* in the eyes using real-time PCR method.

Example 9

A kit for the detection of *Cytophaga hutchinsonii* contains (1) SYBR Green I; (2) Taq enzyme; (3) primer pairs SEQ ID NO:17 GCTGGCTCCTTTGG, SEQ ID NO:18 GCATTACTGCCTGGTG; (4) dNTP; (5) buffer; (6) sterilized water. The kit is applied on the detection of *Cytophaga hutchinsonii* in the eyes using real-time PCR method.

Example 10

A kit for the detection of *Gardnerella vaginalis* contains (1) SYBR Green I; (2) Taq enzyme; (3) primer pairs SEQ ID NO:19 GACTCCGACTTGTTT, SEQ ID NO:20 CATTATCTGGCGTTTTAGC (4) dNTP; (5) buffer; (6) sterilized water. The kit is applied on the detection of *Gardnerella vaginalis* in the eyes using real-time PCR method.

Example 11

A kit for the detection of *Staphylococcus aureus* contains (1) SYBR Green I; (2) Taq enzyme; (3) primer pairs SEQ ID NO:21 GAAGCGGAGTTCAAAGG, SEQ ID NO:22 ATGGCAAATCACCAATCA (4) dNTP; (5) buffer; (6) sterilized water. The kit is applied on the detection of *Staphylococcus aureus* in the eyes using real-time PCR method.

Example 12

A kit for the detection of *Pseudomonas aeruginosa* contains (1) SYBR Green I; (2) Taq enzyme; (3) primer pairs SEQ ID NO:23 GACCAGGTAGCCGTCGTTCTC, SEQ ID NO:24 TGCTGACCCTGACCGACATTC; (4) dNTP; (5) buffer; (6) sterilized water. The kit is applied on the detection of *Pseudomonas aeruginosa* in the eyes using real-time PCR method.

Example 13

A kit for the detection of *Bacillus cereus* contains (1) SYBR Green I; (2) Taq enzyme; (3) primer pairs SEQ ID NO:25 GAAGTGCGTGCGTATAGTGT, SEQ ID NO:26 AAAGAACGACCAAGTGCTG (4) dNTP; (5) buffer; (6) sterilized water. The kit is applied on the detection of *Bacillus cereus* in the eyes using real-time PCR method.

Example 14

A kit for the detection of *Staphylococcus epidermidis* contains (1) SYBR Green I; (2) Taq enzyme; (3) primer pairs SEQ ID NO:27 TTGAAGTGAAACGTCCTC, SEQ ID NO:28 TGTCTCATCTAACCACC (4) dNTP; (5) buffer; (6) sterilized water. The kit is applied on the detection of *Staphylococcus epidermidis* in the eyes using real-time PCR method.

Example 15

A kit for the detection of *Enterococcus faecium* contains (1) SYBR Green I; (2) Taq enzyme; (3) primer pairs SEQ ID NO:29 TGGAGCGATTATACCG, SEQ ID NO:30 GTACCCGCTTGATTGA; (4) dNTP; (5) buffer; (6) sterilized water. The kit is applied on the detection of *Enterococcus faecium* in the eyes using real-time PCR method.

Example 16

A kit for the diagnosis of age-related macular degeneration contains (1) SYBR Green I; (2) Taq enzyme; (3) primer pairs SEQ ID NO:3 GGTTCAATGAGCCTACT, SEQ ID NO:4 GCCAGCGTCTTTCC, (4) dNTP; (5) buffer; (6) sterilized water. The kit is applied on the detection of *Bacillus megaterium* in the eyes using real-time PCR method.

Example 17

Figure 4:
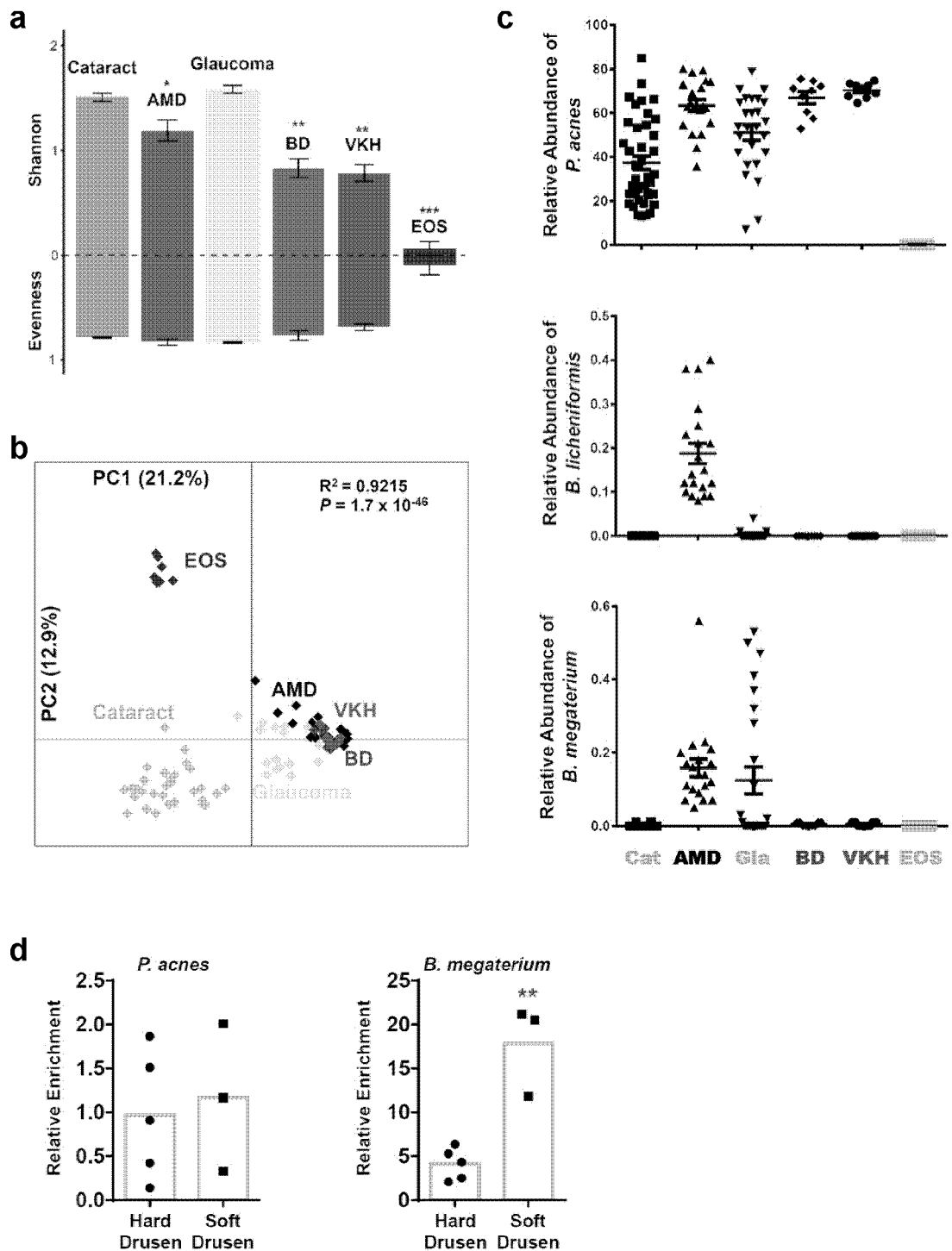
FIG. 4 illustrates intraocular microbiota differentiates ocular diseases. (a) The alpha diversity (measured by Shannon index and Evenness) of the intraocular metagenomes in patients with cataract, AMD, glaucoma, Behcet's disease (BD), Vogt-Koyanagi-Harada Syndrome (VKH), or endophthalmitis (EOS). The error bar represents the mean of all Shannon index or Evenness within the disease group±SEM. The statistical difference was measured between patients with cataract and each of other disease groups, respectively. Mann-Whitney U test significance levels are denoted by asterisks ($*P<0.05$, $P<0.01$, $*P<0.001$). (b) Principle coordination analysis of the similarity of the intraocular metagenomes in patients with cataract, AMD, glaucoma, BD, VKH, or EOS. P value was calculated using PERMANOVA test. (c) The relative abundance of *P. acnes, B. licheniformis*, and *B. megaterium* in the intraocular metagenomes in patients with cataract (Cat), AMD, glaucoma (Gla), BD, VKH, or EOS. (d) The relative fold enrichment of *P. acnes* and *B. megaterium* in the hard drusen and soft drusen tissues as compared to the non-drusen retinal tissues in the same eyes. Mann-Whitney U test significance levels are denoted by asterisks ($**P<0.01$).
Figure 16:
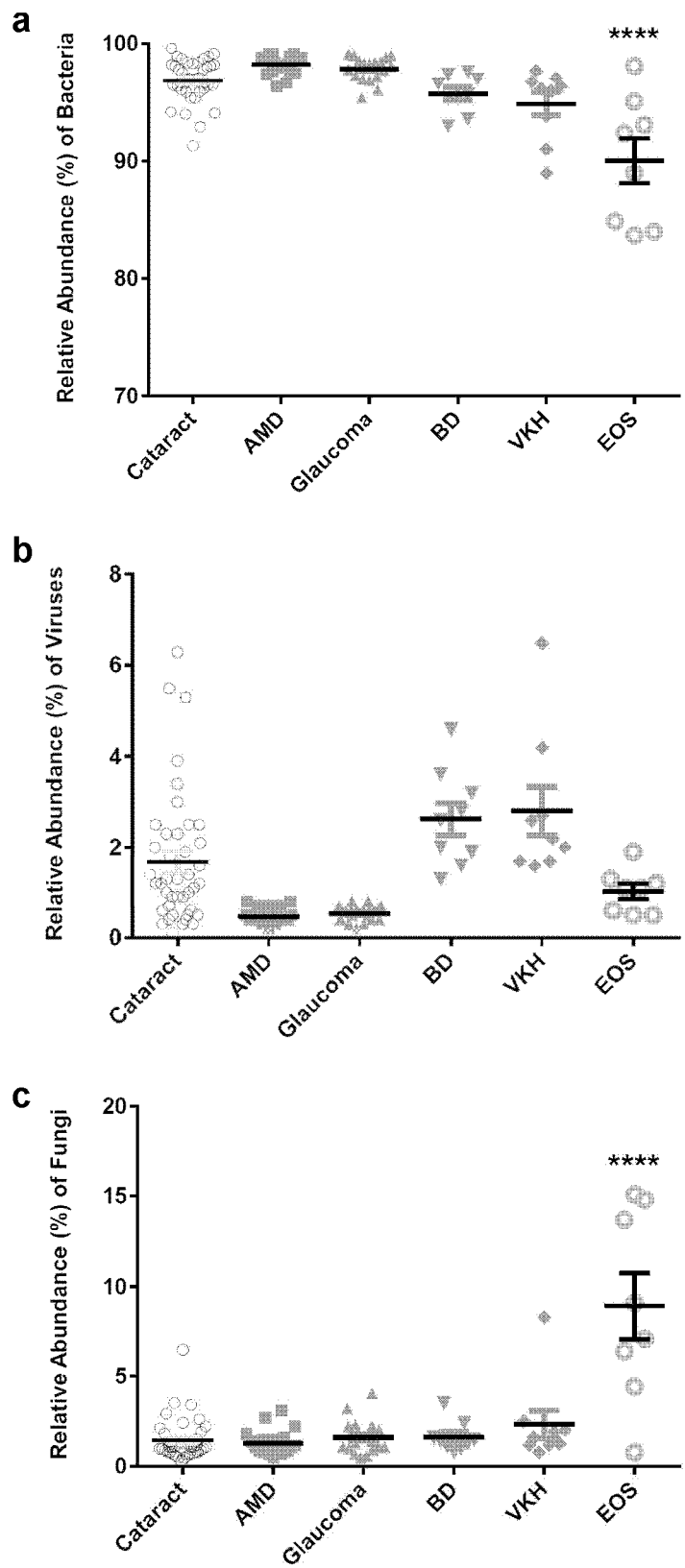
FIG. 16 illustrates the relative abundance of bacterial (a), viral (b), and fungal (c) species of the intraocular metagenomes in patients with cataract, AMD, glaucoma, BD, VKH, or EOS.
Figure 17:
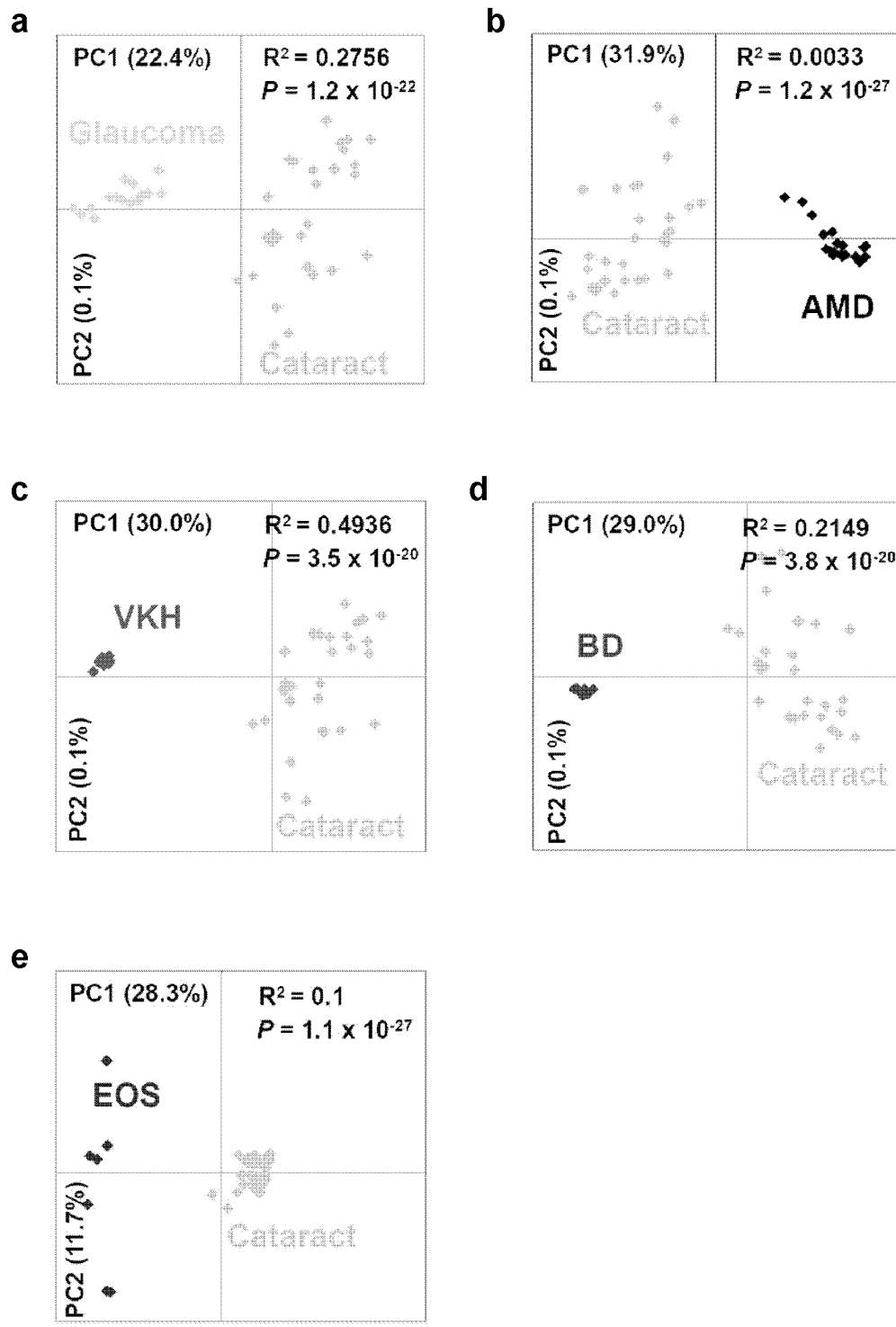
FIG. 17 illustrates similarity of the microbial community between cataract and glaucoma (a), cataract and AMD (b), cataract and VKH (c), cataract and BD (d), and cataract and EOS (e) was analyzed by principle coordination analysis. P value was calculated using PERMANOVA test.

Test Patients:
41 cataract, 20 AMD, 18 glaucoma, 9 BD, 9 VKH, and 8 EOS patients.
Test Methods:
(1) Taking a sample of aqueous humor and extracting DNA from the aqueous sample:
1) Irrigating patients' conjunctival sac using 0.9% sodium chloride solution for three times;
2) Mydriasis using atropine;
3) Applying the ofloxacin solution on patients' eyes for 30 seconds for disinfection;
4) Irrigating patients' conjunctival sac with tobramycin solution for three times for sterilization;
5) Taking a sample of aqueous humor and extracting DNA from the aqueous sample.
(2) Detection of DNA extracted from aqueous humor samples using metagenomic sequencing analysis.
Results:
All human eyes we tested have intraocular microbiota, FIG. 16 is a graph showing the proportion of bacteria, viruses and fungi in the total microbiota in the eyes of patients with different diseases, as shown in FIG. 16, all these 6 types of patients have bacteria as the major component of their intraocular microbiota. FIG. 20 is a LefSe analysis graph of bacterial species that were highly enriched in the eyes of patients with different diseases, as shown in FIG. 20, patients with different diseases have different kinds of bacteria. FIG. 4c is a graph showing the relative abundance of *P. acnes, Bacillus licheniformis* and *Bacillus megaterium* in the eyes of patients with 6 types of diseases. As shown in FIG. 4c, the eyes of AMD patients contain *P. acnes, Bacillus licheniformis* and *Bacillus megaterium* simultaneously, among which the amount of *P. acnes* is the highest, and the amount of *Bacillus licheniformis* and *Bacillus megaterium* is less than that of *P. acnes*, however it is higher than the amount of *Bacillus licheniformis* and *Bacillus megaterium* in the eyes of patients with other 5 diseases.

Example 18

Figure 21:
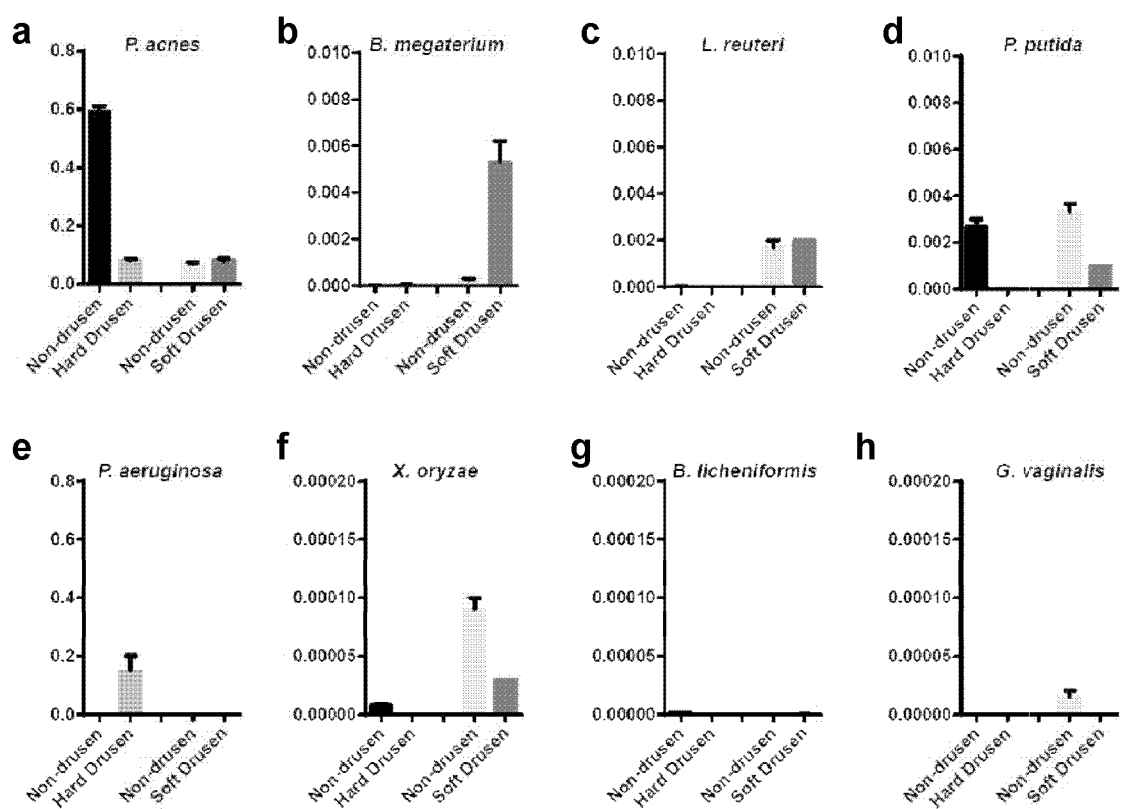
FIG. 21 illustrates relative DNA levels (relative to Human ACTB) of bacteria *P. acnes* (a), *B. megaterium* (b), *L. reuteri* (c), *P. putida* (d), *P. aeruginosa* (e), *X. oryzae* (f), *B. licheniformis* (g), and *G. vaginalis* (h) in non-drusen, hard drusen, and soft drusen tissues.
Figure 23:
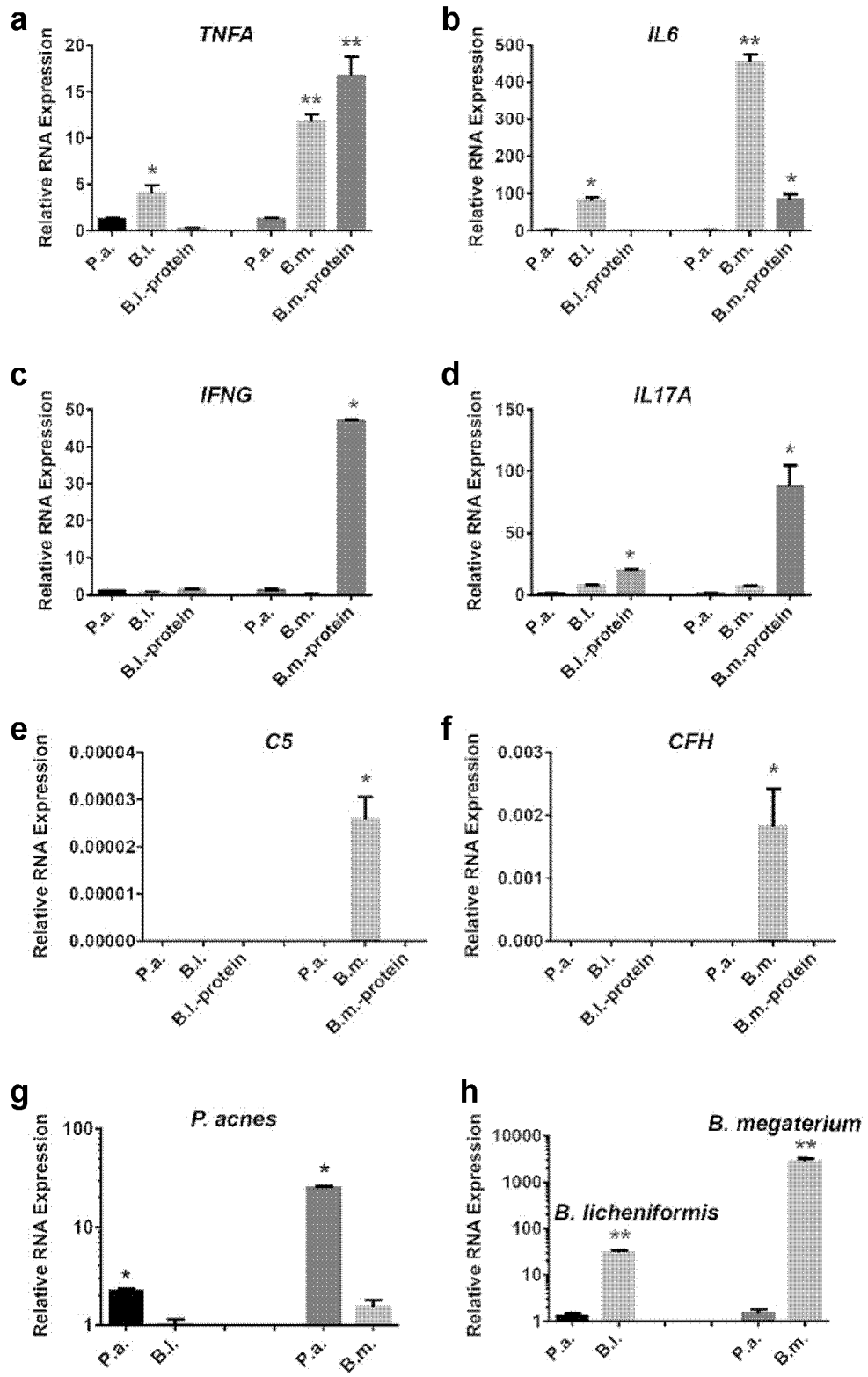
FIG. 23 illustrates (a) Relative RNA expression of TNFA, (b) IL6, (c) IFNG, (d) IL17A, (e) C5, and (f) CFH in the eyes with inoculation of live *P. acnes* (P.a.), live *B. licheniformis* (B.l.), *B. licheniformis* proteins (B.l. protein), live *B. megaterium* (B.m.) and *B. megaterium* proteins (B.m. protein). (g) Relative RNA expression of *P. acnes* in eyes inoculated with *P. acnes* (P.a.), *B. licheniformis* (B.l.), and *B. megaterium* (B.m.). (h, left) Relative RNA expression of *B. licheniformis* in the eyes inoculated with *P. acnes* (P.a.) and *B. licheniformis* (B.l.). (h, right) Relative RNA expression of *B. megaterium* in the eyes inoculated with *P. acnes* (P.a.) and *B. megaterium* (B.m.). The statistical difference was measured against the P.a. inoculations. *P<0.05, Student's T test; **P<0.01, Student's T test.

Experiment Reagents:
Real-time PCR kit prepared in Examples 1-15.
Test Organization:
Non-drusen, hard drusen, and soft drusen tissues of AMD patients
Test Methods:
(1) Taking patient's non-drusen, hard drusen, and soft drusen tissues and extract DNA from each tissue:
1) Irrigating patients' conjunctival sac using 0.9% sodium chloride solution for three times;
2) Mydriasis using compound tropicamide solution;
3) Applying the levofloxacin hydrochloride solution on patients' eyes for 30 seconds for disinfection;
4) Irrigating patients' conjunctival sac with tobramycin solution for three times for sterilization;
5) Taking patient's non-drusen, hard drusen, and soft drusen tissues and extracting DNA from each tissue using the MasterPure Complete DNA and RNA Purification Kit (Epicentre, UK) kit.
(2) Detection of DNA extracted from non-drusen, hard drusen, and soft drusen tissues of AMD patients using real-time PCR method.
Results:
As shown in FIG. 21, our results showed only 8 bacteria could be detected in non-drusen, hard drusen, and soft drusen tissues of AMD using real-time PCR method, *P. acnes* (a), *B. megaterium* (b), *L. reuteri* (c), *P. putida* (d), *P. aeruginosa* (e), *X. oryzae* (f), *B. licheniformis* (g), and *G. vaginalis* (h) respectively, among which *P. acnes* was the most abundant species (FIG. 21a) and *B. megaterium* was the only species enriched in soft drusen (FIG. 21b).

Figure 5:
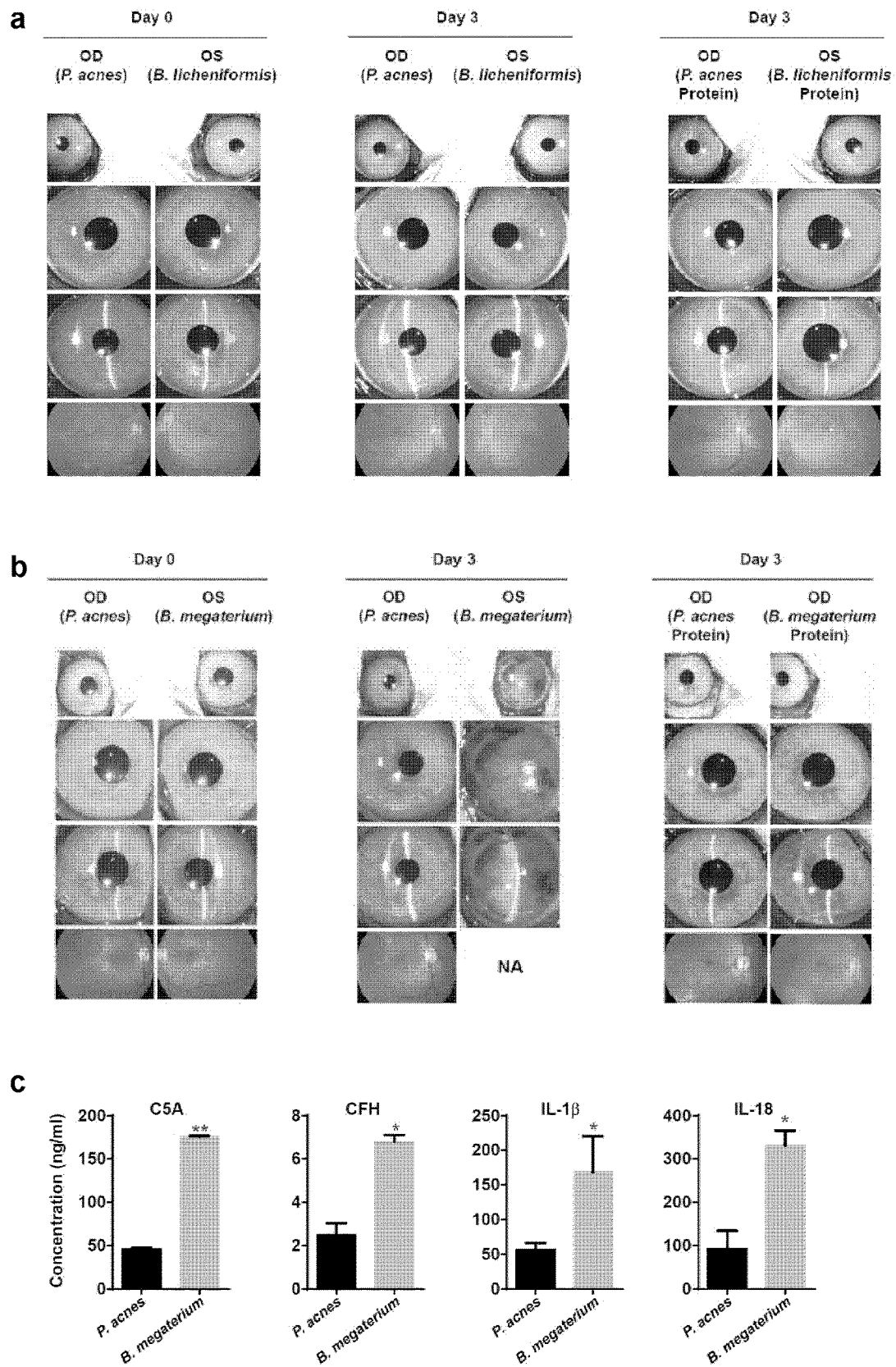
FIG. 5 illustrates that *B. megaterium* induces intraocular inflammation in vivo. (a) The right (OD) and left (OS) eyes of macaques were inoculated with *P. acnes* and *B. licheniformis*, respectively. The ocular surface and fundus view before bacterial inoculation and 3 days post inoculation are shown. (b) The right (OD) and left (OS) eyes of macaques were inoculated with *P. acnes* and *B. megaterium*, respectively. The ocular surface and fundus view before bacterial inoculation and 3 days post inoculation are shown. (c) The concentration of active forms of CSA, CFH, IL-1, and IL-18 in the aqueous humors from macaques inoculated by live *P. acnes* and *B. megaterium* was measured by ELISA. The error bar represents the mean of two independent experiments±SEM with Mann-Whitney U test significance values demarked with asterisk (*P<0.05, **P<0.01).

Example 19. *Bacillus megaterium* Induces Activation of Complement by ARPE19 Cells In Vitro Experimental Material:
Human ARPE19 cells (American type culture collection, USA)
Experimental Strains:
*Bacillus megaterium, Propionibacterium acnes*
Experimental Methods:
Human ARPE19 cells (ATCC, USA) were divided into two groups and cultured in DMEM supplied with 2.5 mM L-glutamine and 10% FBS. Then, *Bacillus megaterium* was added to the first group, and *P. acnes* was added to the second group. After 12, 24, and 48 hours of culture in each group, ARPE19 cells were incubated with PI and AnnexcinV-APC (Cat #88-8007-72, eBioscience, USA) for 30 min. The cell death was measured with MACS Quant Analyzer 10 flow cytometer (MiltenyiBiotec, Germany).
Results:
As shown in FIG. 22a, we found *B. megaterium* but not *P. acnes* significantly increased the pyroptosis of RPE cells in a time dependent manner. As shown in FIG. 22b, we found the activation of complement system was confirmed by the production of active form of C5A protein. Interestingly, both bacteria induced secretion of CFH proteins by ARPE19 cells, while the induction of CFH was more profound by *B. megaterium* than by *P. acnes*. As the result of pyroptosis, FIG. 5c shows that in vitro infection of *B. megaterium* led to secretion of active IL-1 and IL-18 by RPE cells.
Conclusion:
These results indicate that infection of *B. megaterium* can lead to inflammation similarly found in soft drusen.

Example 20

Experimental Animals:
Macaques.
Experimental Strains:
*Bacillus megaterium* BNCC190686, *Bacillus licheniformis* BNCC186069, and *Propionibacterium acnes* BNCC336649 purchased from BeNa Culture Collection (Beijing, China).
Experimental Methods:
*Bacillus megaterium* BNCC190686, *Bacillus licheniformis* BNCC186069, and *Propionibacterium acnes* BNCC336649 were first cultured overnight at 37° C. on agar plates following the standard protocols provided by the manufacturer. The bacterial cultures were then washed in PBS and resuspended as 1×106CFU/1 solutions and further diluted in PBS as injection solutions.
The macaques were sedated by intramuscular injection of a mixture of Tiletamine Hydrochloride (2.5 mg/kg) and Zolazepam Hydrochloride (2.5 mg/kg). After topical anesthesia (0.5% Proparacaine Hydrochloride), the eyes were immediately visualized in vivo using a light microscope. The pupils were then dilated with 0.5% tropicamide and 0.5% phenylephrine to obtain the fundus photographs. Intravitreal injection of bacterial solutions (1000 CFU in a volume of 500) or sonication-inactivated bacterial proteins (from 1000 CFU bacteria) was performed with a 1 ml syringe and 30-gauge needle after ocular surface disinfection with 5% PVI solution. In the first group, the left eye of macaques was inoculated with live *Propionibacterium acnes* bacteria injection, the right eye of macaques was inoculated with live *Bacillus licheniformis* bacteria injection. In the second group, the left eye of macaques was inoculated with *Propionibacterium acnes*' sonication-inactivated proteins injection, the right eye of macaques was inoculated with *Bacillus licheniformis*' sonication-inactivated proteins injection. In the third group, the left eye of macaques was inoculated with live *Propionibacterium acnes* bacteria injection, the right eye of macaques was inoculated with live *Bacillus megaterium* bacteria injection. In the fourth group, the left eye of macaques was inoculated with *Propionibacterium acnes*' sonication-inactivated proteins injection, the right eye of macaques was inoculated with *Bacillus megaterium*' sonication-inactivated proteins injection.

Slit lamp and fundus examinations were conducted for all macaques within 3 days after the injection. The severity of the endophthalmitis was graded according to a previously described standard. The macaques were euthanized 3 days post inoculation and both eyeballs were enucleated for histopathological and intraocular cytokine/bacteria analyses. The eyeballs were fixed in 4% paraformaldehyde for 48 h and then embedded in paraffin. Sections were cut on a microtome at 5 mm and stained with hematoxylin and eosin (H&E).

Figure 3:
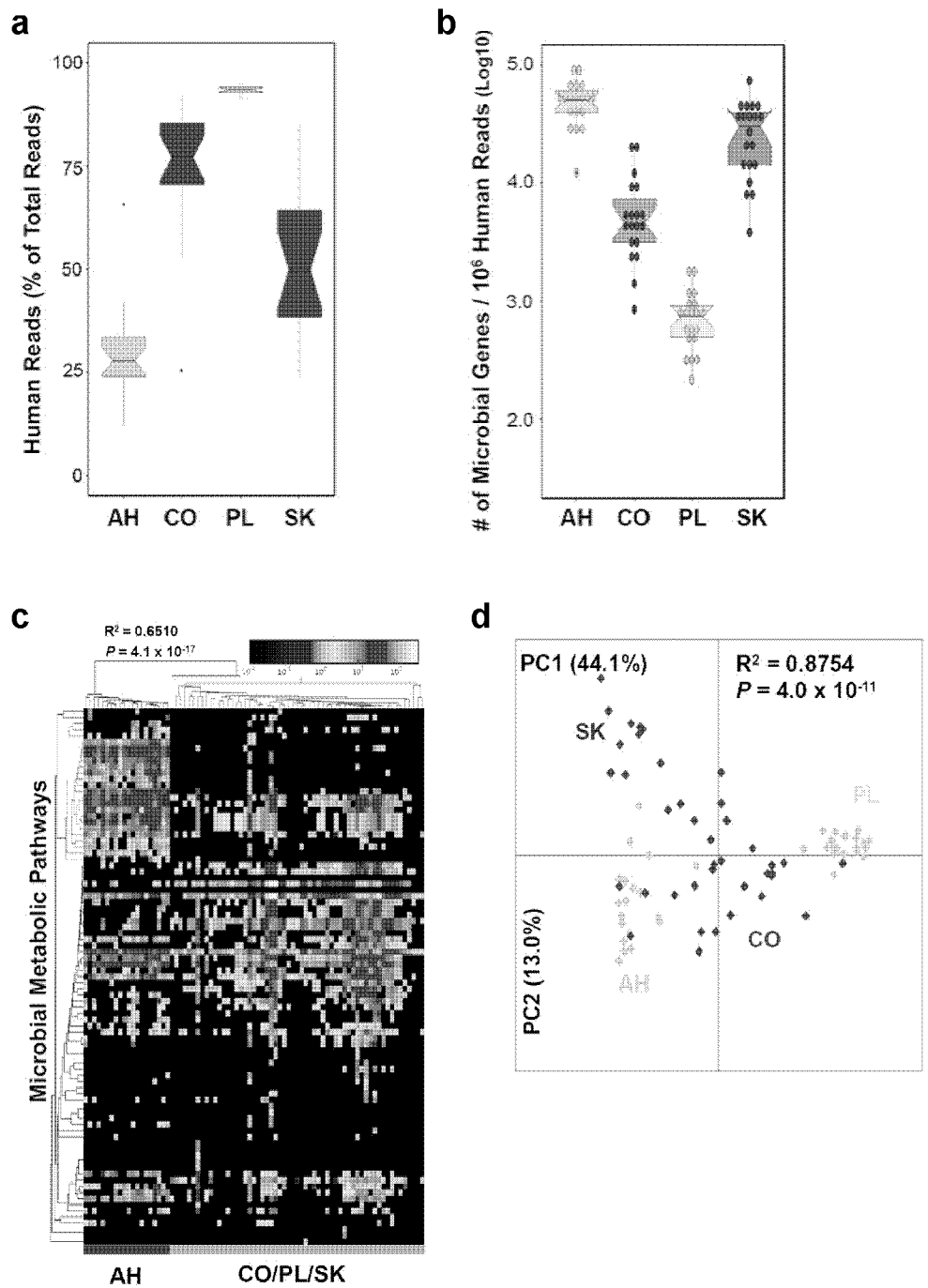
FIG. 3 illustrates a unique live intraocular microbiota. Comparative metagenomic analysis was performed for aqueous humor (AH), conjunctiva (CO), plasma (PL), and skin (SK) specimens from 20 patients undergoing cataract surgery. (a) The average percentage of human reads among total sequenced reads from AH, CO, PL, and SK samples. (b) The average numbers of microbial genes identified in AH, CO, PL, and SK samples. (c) Hierarchical clustering analysis of relative abundance of microbial metabolic pathways identified in AH, CO, PL, and SK samples. P value was calculated using AMOVA test. (d) Diversity of the microbial community analyzed by principle coordination analysis. P value was calculated using PERMANOVA test.

Results: FIG. 5A is a fundus photograph of the first and the second group of macaques, and FIG. 5B is a fundus photograph of the third and the fourth group of macaques, as shown in FIGS. 5A and 5B, 3 days after the injection of live bacterium or inactivated protein, there was no inflammation in the eyes of the macaques in the first group, the second group, and the fourth group, however, severe inflammation was shown in the right eye of the third group of macaques. Therefore, infection of live *P. acnes* bacterium or inoculation of its sonication-inactivated proteins into the eye, as well as live *B. licheniformis* bacterium or inoculation of its sonication-inactivated proteins into the eye did not induce significant intraocular inflammation. However, infection of live *B. megaterium* but not its proteins into the eye led to a profound intraocular inflammation.

G. Examples

Identification of *Bacillus megaterium* as the Major Etiology of Early Age-Related Macular Degeneration Abstract Age-related macular degeneration (AMID) is the leading cause of irreversible vision loss in the elderly worldwide. Despite identification of multiple genetic factors associated with AMD, the environmental factors triggering the damaging local inflammation in AMD remain unclear. Here, using quantitative PCR, negative staining transmission electron microscopy, and high-throughput sequencing technologies, we find that resident microbiota inhabits the intraocular cavities in all eyes. A disease-specific signature of the microbial community differentiates several intraocular diseases including AMD. Importantly, we find that an AMD specific bacterium *Bacillus megaterium* induces activation of complement and retinal cell death in vitro and in vivo. Our study identifies bacterial infection as the major etiology of early AMD, and provides a novel direction for the diagnosis, treatment, and prevention of the leading blinding disease in late life.

Introduction

In the elderly population, Age-related macular degeneration (AMD) is the leading cause of irreversible vision loss worldwide[1]. It is characterized by confluent soft drusen deposited between retinal pigment epithelium (RPE) and the Bruch's membrane and/or retinal pigmentary changes in the macula at the early stage (intermediate AMD). At later stages, advanced AMD is characterized by two major subtypes, geographic atrophy (dry AMD) or choroidal neovascularization (wet AMD) in the macula[1]. While anti-VEGF therapies have been used to control wet AMD, currently there is no approved therapy for dry AMD[1,2].

The pathogenesis of AMD involves both genetic and environmental factors. Numerous studies have identified variations at the loci of genes that are associated with AMD susceptibility, including complement factor H (CFH), age-related maculopathy susceptibility 2 (ARMS2), HtrA serine peptidase 1 (HTRAI), indicating that AMD is possible an inflammatory disease[3-5]. Currently, the environmental factors triggering the local inflammation and leading to the early soft drusen in AMD pathology are not clear.

The intraocular environment has long been considered sterile unless invaded by microorganisms due to trauma, surgical procedures, or hematogenous or neurological spread[6]. Here, we report that the composition of intraocular microbiota can differentiate ocular diseases. Importantly, we identified an AMD specific bacterium *Bacillus megaterium* that could promote the development of AMD pathology.

Methods

Subject Recruitment

Patients with AMD, cataract (Cat), glaucoma (Gla), Behcet's disease (BD), Vogt-Koyanagi-Harada Syndrome (VKH), and endophthalmitis (EOS) were recruited at Zhongshan Ophthalmic Center (Guangzhou, China) and Tianjin Medical University Eye Hospital (Tianjin, China) between September 2014 and August 2018. The basic demographic information for these 13 cohorts (1162 patients) was listed in Table 1. The post mortem eyes were obtained from Guangdong Eye Bank, Guangzhou, China (cohort #3) (Table 1). This study adhered to the tenets of the Declaration of Helsinki and was approved by the Institutional Review Boards of Zhongshan Ophthalmic Center, Sun Yat-sen University (protocol #2014MEKY024, #2014MEKY032, and #2016KYPJ031), Tianjin Medical University Eye Hospital (protocol #2016KY-14), and National Eye Institute, National Institutes of Health (protocol #92-EI-0113). All subjects provided written informed consent before participation.

TABLE 1

|  | Cohort 1 Cataract Aqueous Humor | Aqueous Humor | Cohort 2 Cataract Conjunctiva | Plasma | Skin | Cohort 3 Healthy* Aqueous Humor | Cohort 4 Cataract Aqueous Humor | Cohort 5 AMD Aqueous Humor |
|---|---|---|---|---|---|---|---|---|
| # of Subject | 1000 | 20 | 19 | 20 | 20 | 4 | 41 | 20 |
| Ave Age | 69.9 | 75.0 | 75.0 | 75.0 | 75.0 | 26.8 | 68.4 | 66.3 |
| Male/Female | 431/669 | 10/10 | 10/9 | 10/10 | 10/10 | 2/2 | 10/22 | 12/8 |
| # of Sample | 1000 | 20 | 19 | 20 | 20 | 4 | 41 | 20 |
| Ave # of Total Reads | — | 31,396,400 | 22,240,005 | 43,853,209 | 28,034,294 | 92,052,386 | 41,806,363 | 38,133,965 |
| Ave # of nonHuman Reads passed filter | — | 1,681,502 | 1,961,170 | 1,579,702 | 2,374,707 | 4,632,314 | 15,903,458 | 13,074,569 |

|  | Cohort 6 Glaucoma Aqueous Humor | Cohort 7 BD Aqueous Humor | Cohort 8 VKH Aqueous Humor | Cohort 9 EOS Aqueous Humor | Cohort 10 RD** Vitreous Humor | Cohort 11 AMD Vitreous Humor | Cohort 12 AMD Vitreous Humor | Cohort 13 AMD Vitreous Humor |
|---|---|---|---|---|---|---|---|---|
| # of Subject | 18 | 9 | 9 | 8 | 7 | 5 | 15 | 6 |
| Ave Age | 61.8 | 30.7 | 49.1 | 34.6 | 60 | 64.2 | 70.1 | 80.7 |
| Male/Female | 6/12 | 6/3 | 4/5 | 4/4 | 4/3 | 1/4 | 9/6 | 2/4 |
| # of Sample | 18 | 9 | 9 | 8 | 7 | 5 | 15 | 6 |
| Ave # of Total Reads | 40,585,158 | 13,073,710 | 16,504,519 | 74,901,194 | — | — | — | — |
| Ave # of nonHuman Reads passed filter | 13,699,598 | 1,285,029 | 1,432,016 | 5,391,645 | — | — | — | — |

*The Cohort 3 was from post mortem donors who died of accident and were free of ocular diseases.
**RD: Retinal Detachment Negative Staining Transmission Electron Microscopy Fifty µl of fresh aqueous humor (AH) specimens or cultured AH samples were centrifuged at 14000 rpm for 20 min. Supernatant was removed saving 5 µl of fluid, which was then loaded onto a copper grid with carbon film. The grid with sample was then stained with 2 µl phosphotungstic acid (3%) for 1 min. The grid was immediately examined using a JEM2010 electron microscope (JEOL Ltd., Japan). The images were acquired on a 2k×2k 895 CCD camera (Gatan, Calif. USA). All reagents and grids were sterilized. Water without any AH samples was used as negative controls and no bacteria were found after extensive search in negative controls.

Metagenomic Sequencing and Data Analysis

A total of 100 ng of DNA from each sample was sonicated into fragments of 300-400 bp using Bioruptor (Diagenode, Belgium) and subjected to sequencing library preparation following the standard protocol provided by the manufacturer using VAHTS Nano DNA Library Prep Kit for Illumina (Vazyme, China). DNA libraries were sequenced to a depth of 10~50 million reads per sample using HiSeq PE Cluster Kit v4 and HiSeq SBS V4 250 cycle kit (Illumina, USA) on the Illumina HiSeq2500 sequencer and subjected to initial processing using CASAVA (v1.8.2) (Illumina). All reads were quality controlled and non-human sequences were subjected to analysis of community composition using Kraken[7] (with pre-built 4 GB database as the reference including complete bacterial, archaeal, and viral genomes in RefSeq as of Dec. 8, 2014), as well as functional analysis using HUMAnN2[8]. (See also paragraphs[00287]-[00307].)

Analysis of Subretinal Bacterial Infection in Macaque

The macaques were sedated by intramuscular injection of a mixture of tiletamine hydrochloride (2.5 mg/kg) and xolazepam hydrochloride (2.5 mg/kg). After instilling topical anesthesia (0.5% proparacaine hydrochloride), the eyes were immediately visualized in vivo using a light microscope. The pupils were then dilated with 0.5% tropicamide and 0.5% phenylephrine to obtain the fundus photographs. Then a 35 gauge anterior chamber cannula was inserted through a sclerotomy and advanced through the vitreous. Under microscopic monitoring, 20 1 of PBS (with or without bacteria) was injected into the subretinal space between photo receptors and RPE, using a NanoFil Syringe Nanofil-100 for Microinjection (World Precision Instruments, USA). All procedures were done using sterile instruments. The macaque was euthanized 47 days post inoculation and the eyeball was enucleated for histological analyses. The eyeballs were fixed in 4% paraformaldehyde for 48 h and then embedded in paraffin. Sections were cut on a microtome at 6 µm and stained with H&E.

Results

The Intraocular Environment is not Sterile

Figure 8:
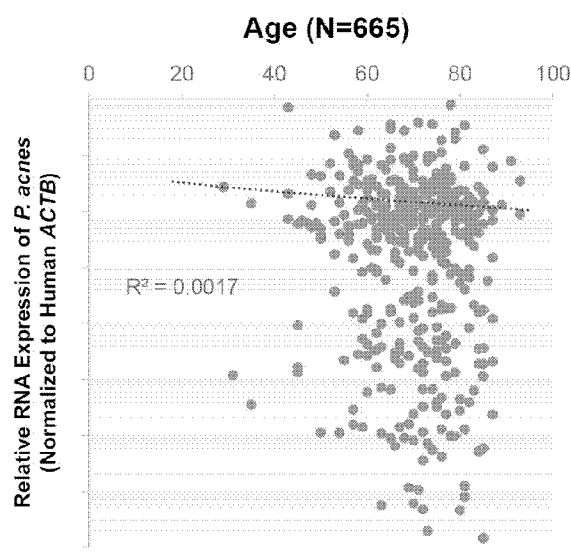
FIG. 8 illustrates the correlation ($R^2$) between intraocular *P. acnes* load (represented by RNA expression of PPA_RS045200) and patient age.

Our preliminary study found *Propionibacterium acnes* (*P. acnes*) (both DNA and RNA), a key pathogen inducing endophthalmitis[9], in uninflamed human eyes. This argued against the traditional idea that intraocular environment should be sterile in normal eyes. We therefore collected 1000 AH specimens from eyes undergoing cataract surgeries that were free of active or history of intraocular inflammation and infection (The summary demographic characteristics of all patients were listed in cohort 1 Table 1). Surprisingly, we were able to detect the 16S rRNA expression of *Propionibacterium* spp. in 71.4% of eyes and RNA expression of a *P. acnes* specific gene—PPA_RS04200 in 63.9% of eyes, based on the real-time PCR assays (FIG. 1a, 7a, 7b). However, the intraocular load of *P. acnes* was not age-related (FIG. 8). It was unexpected that a commensal bacterium of human skin and opportunistic pathogen associated with post-cataract-surgery endophthalmitis' could be detected in a majority of eyes from patients experiencing no ocular inflammation before or after the cataract surgery.

Figure 9:
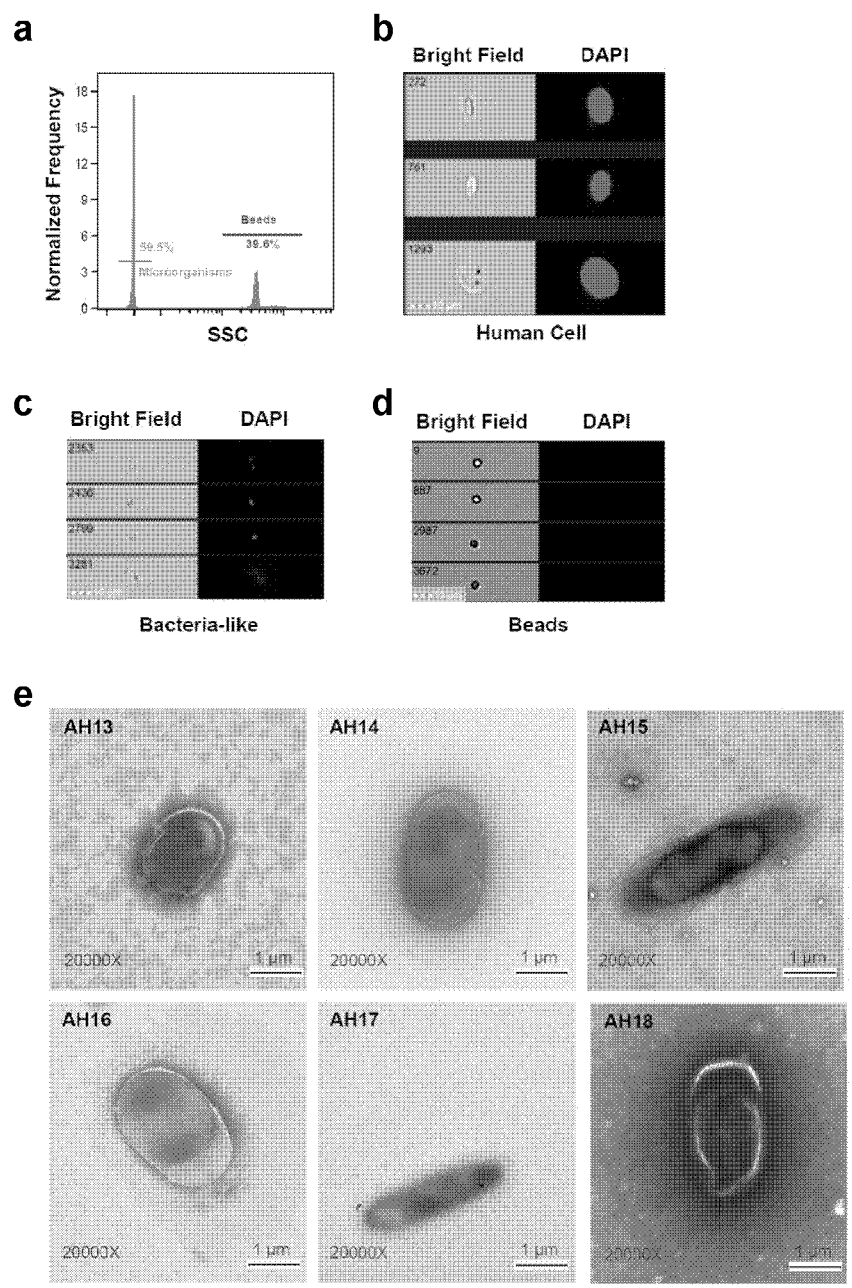
FIG. 9 illustrates detection of intraocular bacteria in AH specimens. Imaging flow cytometry analysis of AH for intraocular microorganisms was performed. (a) The size of intraocular microorganisms (green) was smaller than the size of spiked-in beads (red, 2 mm in diameter). (b) The bright field view and nucleus staining by DAPI of human cells in AH. (c) The bright field view and nucleus staining by DAPI of bacteria-like cells in AH. (d) The bright field view and nucleus staining by DAPI of spiked-in beads in AH. The a-d were representative staining of 43 AH from cataract patients and post mortem eyes. (e) Negative staining transmission electron microscopy was used to visualize bacteria in minimally manipulated fresh AH specimens at 20,000× magnification.

Identification of intraocular *P. acnes* led us to ask the question whether it is possible that other microorganisms also live inside of the normal eyes. Therefore, we carried out single cell analysis of aqueous humors from cataract patients, using Imaging Flow Cytometry technology. By spiking in round beads, we found many microorganisms with a diameter less than 2 µm (the size of beads) in AH (FIG. 9a). Interestingly, live human cells (DAPI positive) (FIG. 9b), spherical/rod microorganisms (DAPI positive) (FIG. 9c), and beads (FIG. 9d) were all visible on the images of particles. We found similar staining of microbial cells in all 43 AHs from 39 cataract patients and 4 post mortem eyes we tested.

To directly visualize bacteria in intraocular fluid, AH specimens were examined using negative staining transmission electron microscopy. As a positive control, the rod-shaped cultured *P. acnes* were successfully visualized. In negative controls containing no AH specimens no bacterium could be found using the identical negative staining protocol (FIG. 1b). Intriguingly, multiple round- and rod-shaped bacteria were found in AH samples (FIGS. 1c and 9e). Within some bacteria, endospores were evident. These data demonstrated the existence of multiple types of intraocular bacteria in cataract patients.

Figure 2:
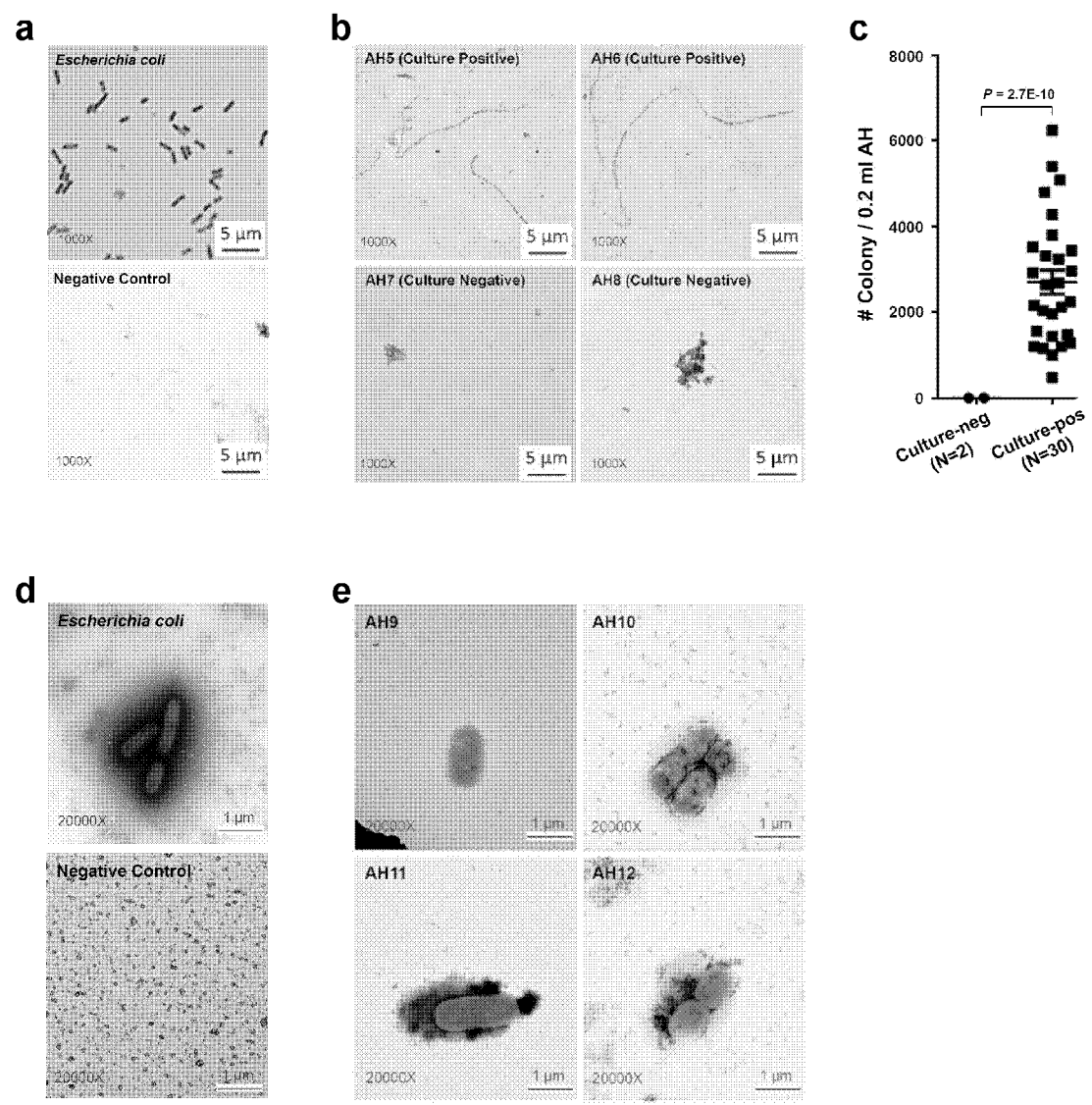
FIG. 2 illustrates detection of bacteria in AH cultures. (a) Cultured *E. coli* was visualized by light microscopy. The negative control consists of sample preparation buffer without any AH inoculation. (b) Bacteria in cultured AH samples (examples of culture positive and negative samples) were visualized by light microscopy. (c) Total colonies per AH culture (starting with 50 μl AH in 6 ml cooked meat medium) were counted and normalized to estimate the number of colonies per 0.2 ml AH. (d) Negative staining transmission electron microscopy visualized cultured *E. coli* and negative control (water without AH cultures) at 20,000× magnification. (e) Selected representative cultured AH samples at 20,000× magnification visualized by negative staining transmission electron microscopy.
Figure 10:
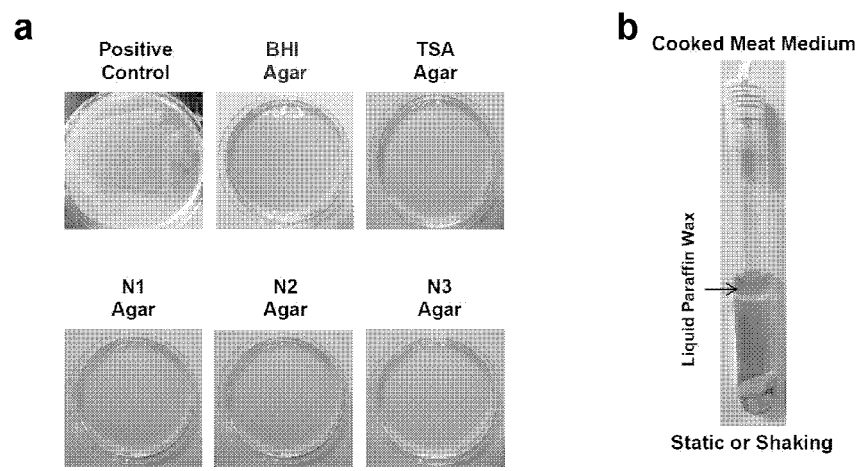
FIG. 10 illustrates culture of AH in agar-based or liquid medium. (a) Cultures (negative) of AH in BHI, TSA, N1, N2, and N3 agar mediums. (b) Cultures in cooked meat medium covered by liquid paraffin wax.

It is expected that intraocular bacteria can be cultured if they can be found using a microscope. We therefore made multiple attempts to culture out the bacteria from AH samples. Using 5 Agar-based culture mediums with various nutrients we found no positive cultures of AH samples from cataract patients (FIG. 10a), however cultures using liquid cooked meat medium (FIG. 10b) were found positive for bacteria and could be visualized using standard light microscopes (FIGS. 2a and 2b). On average, we found 2700 CFU (colony forming units) bacteria per 0.2 ml AH from each eye and 30 out of 32 (93%) eyes were found bacteria positive (FIG. 2c). Cultured bacteria from these AH samples were also examined using negative staining transmission electron microscopy. Both round- and rod-shaped bacteria were found (FIGS. 2d and 2e). These data confirmed the existence of multiple types of intraocular bacteria.

A Unique Live Microbiota Habitats Intraocular Cavities in Human and Animals

Figure 11:
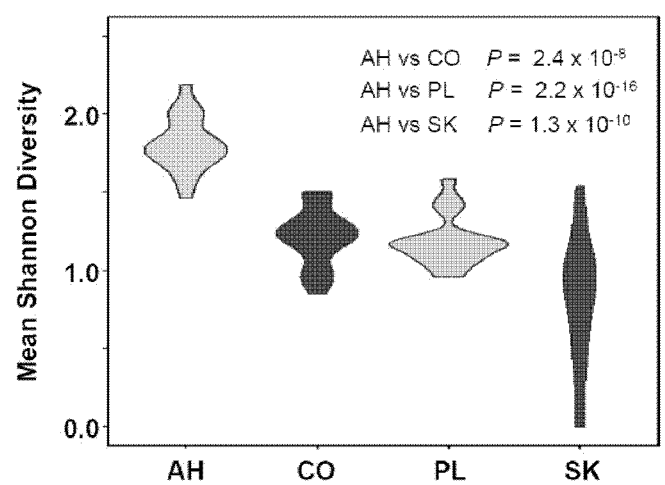
FIG. 11 illustrates the alpha diversity (measured by Shannon index) of the bacterial composition in the AH, CO, PL, and SK samples. P value was calculated using Mann-Whitney U test.

Identification and visualization of intraocular bacteria led us to ask the question whether a microbiota lives inside of normal eyes. To identify the composition and function of intraocular microbial communities in AH, we collected specimens of AH, conjunctiva, plasma, and eyelid skin from 20 patients undergoing cataract surgery (Table 1 presents the demographic characteristics of all patients that are listed in cohort 2). High-throughput sequencing technology was used to profile the metagenomes of these specimens. A large number of human reads were detected among samples from all tissues (FIG. 3a); however, the relative amount of human reads within the AH samples (~28%) was significantly lower than the other three tissues (FIG. 3a). The average numbers of microbial genes detected in AH samples (FIG. 3b) as well as the alpha diversity (detected by Shannon Index) of the microbial community in AH (FIG. 11) were significantly higher than in the other three tissues. Unsupervised hierarchical clustering of metabolic pathways in microbiota from the four tissues found a unique metabolic pattern enriched in AH samples (Table 2) that was distinct from the other three tissues, which were indistinguishable (FIG. 3c). A principle coordinate analysis (PCoA) of community similarity (including bacteria, fungi, and viruses) indicated that the microbiome of AH was different from the other three tissues (FIGS. 3d and 12a-c). The major kingdom of microorganisms was bacteria in all tissues, but the relative abundance of fungal and viral species differed among four tissues (FIG. 13a). In addition to the detection of

TABLE 2

| KEGG Pathway | AH (Ave) | CO (Ave) | SK (Ave) | PL (Ave) | P Value | $R^2$ |
|---|---|---|---|---|---|---|
| hexitol degradation | 24.3 | 0.6 | 7.3 | 0.0 | 1.55E−21 | 0.459 |
| menaquinol-8 biosynthesis 1 | 31.0 | 0.3 | 0.5 | 0.0 | 1.57E−19 | 0.680 |
| pyridoxal 5-phosphate biosynthesis and salvage | 38.1 | 2.5 | 16.7 | 1.4 | 1.19E−16 | 0.570 |
| polyamine biosynthesis 11 | 27.6 | 0.0 | 1.3 | 0.1 | 8.06E−16 | 0.782 |
| starch degradation V | 9.8 | 1.0 | 4.5 | 0.6 | 1.20E−14 | 0.493 |
| lysine, threonine and methionine biosynthesis 1 | 19.1 | 2.3 | 19.0 | 0.6 | 2.18E−14 | 0.356 |
| phenylalanine biosynthesis | 33.1 | 3.8 | 19.9 | 1.1 | 1.24E−12 | 0.582 |
| menaquinol-12 biosynthesis | 16.3 | 0.4 | 0.6 | 0.0 | 3.79E−12 | 0.774 |
| (KDO)2-lipid A biosynthesis | 13.8 | 0.4 | 0.0 | 0.0 | 7.42E−12 | 0.593 |
| menaquinol-9 biosynthesis | 6.6 | 0.3 | 0.5 | 0.0 | 1.83E−11 | 0.427 |
| adenosine nucleotides de novo biosynthesis 11 | 23.1 | 3.1 | 7.2 | 1.1 | 5.11E−09 | 0.517 |
| beta; -D-glucuronide and D-glucuronate degradation | 11.7 | 0.0 | 0.2 | 0.0 | 7.88E−09 | 0.743 |
| tetrahydrofolate biosynthesis and salvage | 11.9 | 0.4 | 0.0 | 0.0 | 1.52E−08 | 0.678 |
| heme biosynthesis from uroporphyrinogen-111 | 4.8 | 0.3 | 1.6 | 0.0 | 2.77E−08 | 0.329 |
| glyoxylate cycle and fatty acid degradation | 6.5 | 0.2 | 0.3 | 0.0 | 3.21E−08 | 0.394 |
| menaquinol-11 biosynthesis | 4.7 | 0.4 | 0.6 | 0.0 | 1.09E−07 | 0.429 |
| adenosine nucleotides de novo biosynthesis 1 | 12.9 | 3.1 | 7.2 | 1.1 | 2.42E−07 | 0.415 |
| D-glucarate and D-galactarate degradation | 2.5 | 0.0 | 0.5 | 0.0 | 2.69E−07 | 0.458 |
| guanosine nucleotides de novo biosynthesis 11 | 18.3 | 3.2 | 7.3 | 1.1 | 5.72E−07 | 0.381 |

*Propionibacterium* spp. transcribed RNA in the eyes of most cataract patients (FIG. 1a), the metagenomic data also demonstrated that sequencing reads of *P. acnes* from individual AH sample were able to cover the full length genome of the organism (FIG. 13b).

Figure 14:
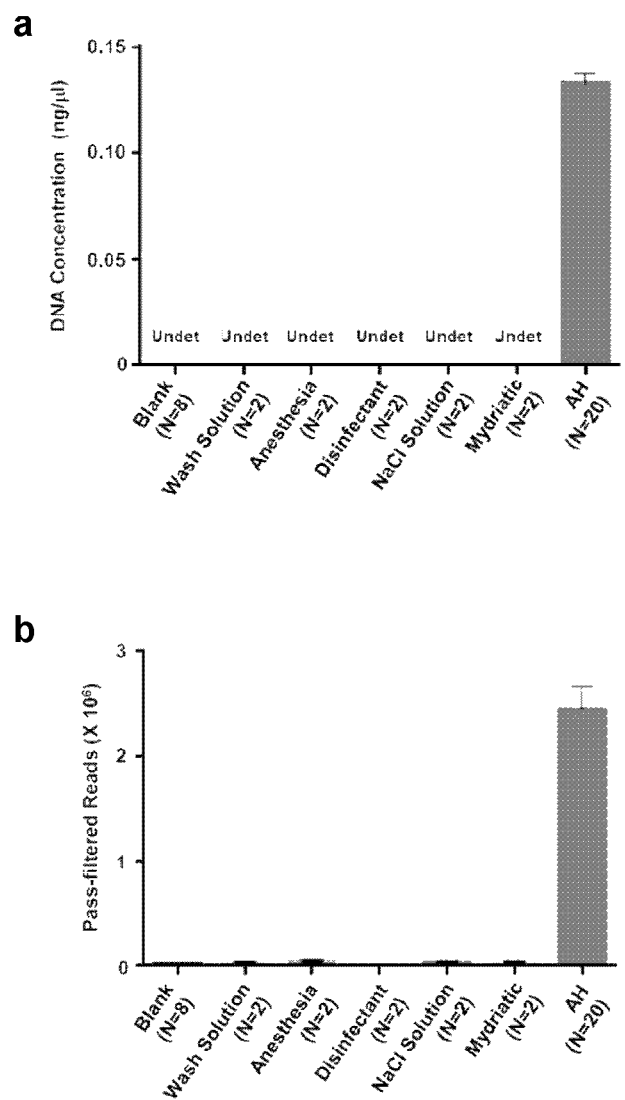
FIG. 14(*a*) illustrates the average DNA concentration of Blank, Wash Solution, Anesthesia, Disinfectant, NaCl Solution, Mydriatic, and AH samples.

Importantly, no DNA was detected in multiple negative controls including Blank (no AH), Wash Solution, Anesthesia, Disinfectant, NaCl Solution, and Mydriatic samples and metagenomic sequencing of these negative controls resulted in few quality reads (see supplementary RESULTS and FIG. 14a-b). These data suggest that the microbiome detected in the AH specimens is not a contamination from conjunctiva, blood, or skin during sampling process. Instead, it represents a unique live community. Importantly, the intraocular microbiome, profiled by metagenomic sequencing analysis, resides in all animals we tested including rat, rabbit, pig, and macaque (5 eyes per species). (See also paragraphs[00308]-[00310].)

Intraocular Microbiota Differentiates Ocular Diseases

Figure 18:
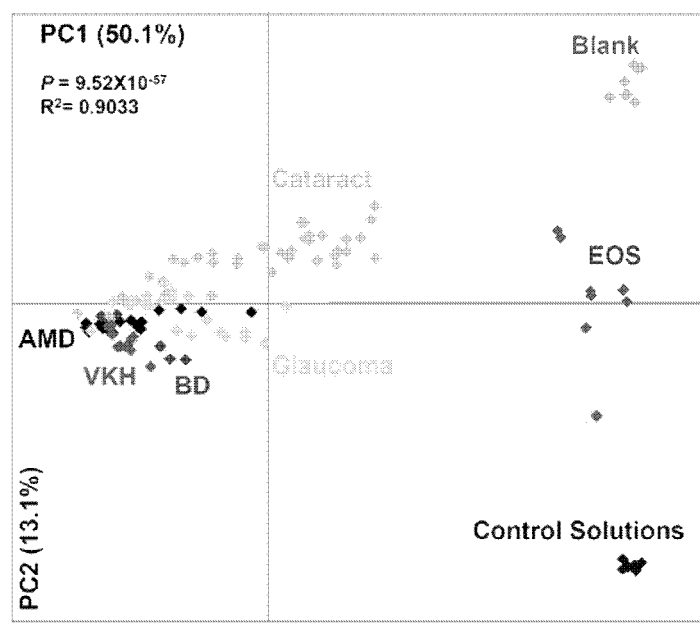
FIG. 18 illustrates similarity of the microbial community between patient specimens and controls was analyzed by principle coordination analysis. P value was calculated using PERMANOVA test.

As all human eyes we tested have intraocular microbiota, we next investigated whether a disease-specific intraocular microbiome could characterize ocular manifestations. We carried out metagenomic sequencing analysis on aqueous humor specimens from 41 cataract, 20 AMD, 18 glaucoma, 9 BD, 9 VKH, and 8 EOS patients (Table 1 lists the summary demographic characteristics of all patients in cohort 4-9). Interestingly, the alpha diversity and evenness of the intraocular microbial communities were significantly different among these 6 types of patients (FIG. 4a), despite all patients having bacteria as the major component of their intraocular microbiome (FIG. 16a-c). The PCoA on the composition of the intraocular microbiota (using all microbial species) showed clear differences among cataract, EOS, and some glaucoma patients. However, AMD, VKH, BD, and some glaucoma patients shared indistinguishable features in their intraocular microbiome when examining the first two principle coordinates (FIGS. 4b and 17a-e). Importantly, the intraocular microbial communities in all patients were significantly different from all sequencing experiments that included specimen-free negative controls (FIG. 18). Similarly, hierarchical clustering analysis of the abundance of functional microbial genes from all metagenomes indicated that each ocular manifestation had a general signature of microbial function, while there were outliers in every disease group that could be classified to other disease clusters (FIG. 19a). In spite of the significant individuality presented by the intraocular microbiome (FIG. 19b), we were able to identify signature bacterial species for each ocular disease group we tested (FIG. 20). Taken together, our results suggest that the composition and function of intraocular microbiota can differentiate ocular diseases such as AMD, cataract, glaucoma, BD, VKH, and EOS.

*Bacillus megaterium* is Enriched in Soft Drusen from AMD Patients

Our metagenomic analysis identified 14 bacterial species that were highly enriched in the AH of AMD patients (FIG. 20 and Table 3). While *P. acnes* was the most abundant microorganism in the AH of AMD patients (FIG. 4c), *Bacillus licheniformis* (*B. licheniformis*) and *Bacillus megaterium* (*B. megaterium*) (FIG. 4c) were the most enriched species, among the 14 AMD-specific ones, in AMD AH specimens (Table 3). We then carried out PCR analysis to investigate whether the 14 AMD-specific bacteria could be detected in the hard or soft drusen tissues, as compared to the non-drusen retinal tissues from 6 archived ocular slides of AMD patients. Our results showed only 8 bacteria could be detected (FIG. 21a-h), among which *P. acnes* was the most abundant species (FIG. 21a) and *B. megaterium* was the only species enriched in soft drusen (FIG. 21b). Intriguingly, the relative abundance of *P. acnes* was comparable in hard drusen, soft drusen, and dry AMD lesion tissues as compared to the non-drusen non-lesion retinal tissues (FIG. 4d). The relative abundance of *B. megaterium* was elevated by ~18 fold in soft drusen when compared to the non-drusen/non-lesion tissues (FIG. 4d). These data suggest a possible role of *B. megaterium* in drusen formation and AMD pathogenesis.

TABLE 3

| | Bacteria Name | Fold change (AMD vs Cat) | PValue (AMD vs Cat) | Q Value (AMD vs Cat) | AMD (Ave) | Cat (Ave) | Gla (Ave) | BD (Ave) | VKH (Ave) | EOS (Ave) |
|---|---|---|---|---|---|---|---|---|---|---|
| High Abandance | *Bacillus licheniformis* | 324.1 | 1.7E−07 | 1.7E−06 | 0.187 | 0.000 | 0.002 | 0.000 | 0.000 | 0.000 |
| | *Bacillus megaterium* | 11.2 | 1.2E−05 | 6.2E−05 | 0.159 | 0.014 | 0.124 | 0.004 | 0.004 | 0.000 |
| | *Pseudomonas putica* | 8.3 | 2.1E−05 | 3.5E−05 | 0.530 | 0.064 | 0.067 | 0.053 | 0.053 | 0.001 |

TABLE 3-continued

|  | Bacteria Name | Fold change (AMD vs Cat) | PValue (AMD vs Cat) | Q Value (AMD vs Cat) | AMD (Ave) | Cat (Ave) | Gla (Ave) | BD (Ave) | VKH (Ave) | EOS (Ave) |
|---|---|---|---|---|---|---|---|---|---|---|
|  | Stenotrophomonas maltophilia | 5.4 | 7.4E−08 | 2.5E−07 | 1.159 | 0.213 | 0.537 | 0.078 | 0.071 | 0.001 |
|  | Bacillus cereus | 4.6 | 4.5E−07 | 8.9E−07 | 0.122 | 0.027 | 0.047 | 0.012 | 0.018 | 0.000 |
|  | Pseudomonas aeruginosa | 1.9 | 1.3E−02 | 1.4E−02 | 0.696 | 0.375 | 0.678 | 0.059 | 0.068 | 0.000 |
|  | Staphylococcus epidermidis | 1.7 | 1.4E−01 | 1.0E+00 | 3.130 | 1.801 | 1.054 | 1.000 | 1.263 | 20.668 |
|  | Staphylococcus aureus | 1.6 | 1.7E−01 | 1.0E+00 | 0.610 | 0.388 | 0.302 | 0.064 | 0.067 | 0.256 |
|  | Staphylococcus haemolyticus | 1.5 | 1.9E−01 | 1.0E+00 | 0.149 | 0.100 | 0.090 | 0.050 | 0.042 | 0.006 |
| Low Abandance | Xanthomonas oryzae | 73.1 | 9.2E−08 | 2.3E−07 | 0.054 | 0.001 | 0.000 | 0.000 | 0.000 | 0.000 |
|  | Cytophagahutchinsonii | 8.5 | 1.4E−04 | 1.9E−04 | 0.032 | 0.002 | 0.001 | 0.000 | 0.000 | 0.000 |
|  | Enterococcus faecium | 11.4 | 1.3E−02 | 1.3E−02 | 0.039 | 0.003 | 0.022 | 0.002 | 0.000 | 0.000 |
|  | Lactobacillus reuteri | 3.5 | 6.6E−02 | 1.0E+00 | 0.051 | 0.014 | 0.011 | 0.001 | 0.003 | 0.044 |
|  | Gardnerella vaginalis | 2.8 | 1.3E−02 | 1.6E−02 | 0.041 | 0.015 | 0.015 | 0.019 | 0.013 | 0.000 |

*Bacillus megaterium* Induces Activation of Complement, Pyroptosis of RPE Cells, and Intraocular Inflammation In Vivo Next, we tested whether *B. licheniformis* and *B. megaterium* were able to induce inflammation in vivo. We chose the non-human primate macaque (*Macaca fascicularis*) as our model system considering the ocular anatomy and intraocular environment shared by human and macaque. As shown in FIG. 5*a*, intravitreal infection of live *P. acnes* or *B. licheniformis* did not induce significant intraocular inflammation. Neither did injection of sonication-inactivated proteins of either *P. acnes* or *B. licheniformis* induce significant inflammation. Conversely, infection of live *B. megaterium* but not its proteins into the eye led to a profound intraocular inflammation (FIG. 5*b*). The intraocular inflammation induced by live *B. megaterium* was characterized by the elevation of TNFA and IL6 but not IFNG or IL17A expression (FIG. 23*a-d*). Importantly, only live *B. megaterium* was able to activate complement system including C5A and CFH (FIGS. 5*c* and 23*e-f*) and induce pyroptotic cytokines IL-1 and IL-18 in vivo (FIG. 5*c*). The bacteria remained alive in the eyes after inflammation was initiated (FIG. 23*g-h*), suggesting the intraocular inflammation may be long lasting in nature. These data demonstrate that intravitreal infection of *B. megaterium* can activate complement system and induce intraocular inflammation in vivo.

*Bacillus megaterium* Induces Drusenoid Lesions in Macaque

Figure 6:
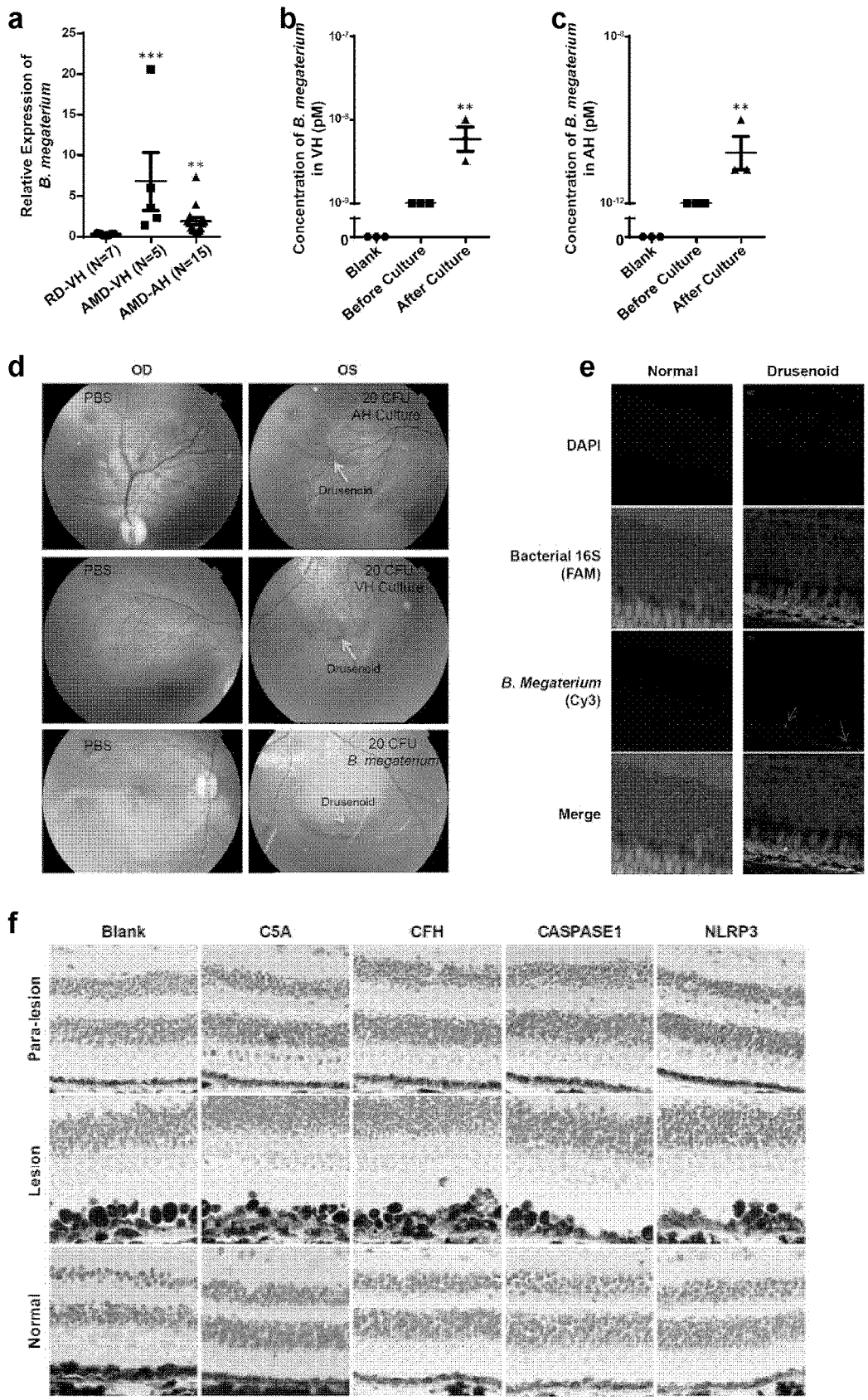
FIG. 6 illustrates intraocular bacteria and *B. megaterium* induce retinal drusenoid lesions in vivo. (a) Relative expression of *B. megaterium* (presented as the percentage of human ACTB expression) in the aqueous humors (AH) and vitreous humors (VH) from patients with retinal detachment (RD), and AMD was quantified using real-time PCR assays. (b) The total amount of *B. megaterium* DNA in 3 VH (b) and 3 AH. (c) before and after bacterial cultures was quantified using real-time PCR assays. (d) Fundus view on post injection Day 47 of the macaque receiving subretinal inoculation of 20 CFU of AH culture, VH culture and *B. megaterium*. (e) FISH staining of bacterial 16S rDNA and *B. megaterium* DNA in the retinal section of monkey eyes on post innoculation Day 47. Arrow, *B. megaterium*. (f) Immunohistochemistry staining of CSA, CFH, CASPASE1, and NLRP3 proteins on the retinal sections of normal, lesion, and para-lesion areas of VH culture infected macaque. The error bar represents the mean of two independent experiments±SEM with Mann-Whitney U test significance values demarked with asterisk (P<0.01, *P<0.001).
Figure 25:
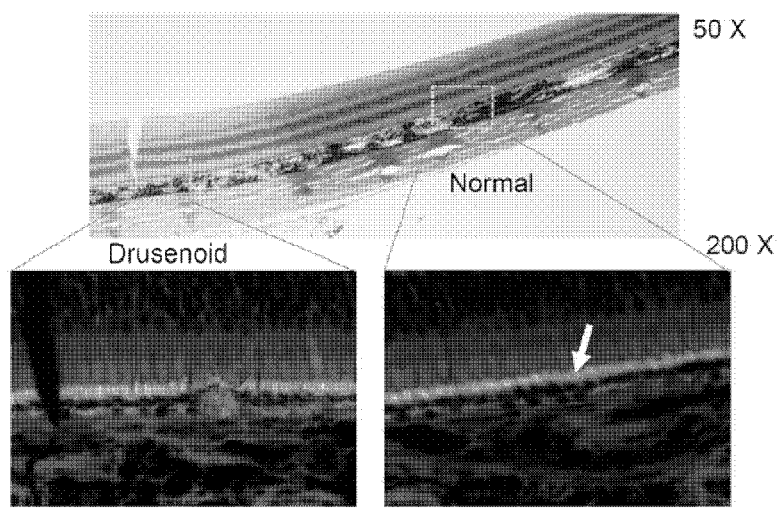
FIG. 25 illustrates HE staining and fluorescence microscope observations of the retinal tissues from the macaque receiving subretinal inoculation of *B. megaterium* on Day 47.

If *B. megaterium* was a cause of AMD, the Kock's postulate has to be satisfied. Our above results demonstrated the existence of *B. megaterium* in both AH and retinal tissues (FIG. 4*c*, 4*d*, 21*b*, and Table 3). We again collected both AH and vitreous humor (VH) specimens from AMD patients and were able to detect *B. megaterium* DNA in both uncultured and cultured samples (FIG. 6*a-c*). We next examined whether subretinal inoculation of AH and VH cultures which had *B. megaterium*, as well as the cultured single species of *B. megaterium* led to AMD like pathology in macaque (FIG. 24*a-b*). About 20 CFU of bacteria (in 20 l PBS) from AH, VH, and *B. megaterium* cultures were injected subretinally and PBS was used as a control (illustrated in FIG. 24*b*). The fundus examination of macaque eye was performed before (Day 0) and after bacterial inoculation on Day 1, Day 3, Day 35 (data not shown), as well as Day 47 (FIG. 6*d*). The PBS injection left only visible scar on the retina, while all bacterial inoculations led to drusenoid lesions on retinal tissues (FIG. 6*d*). Drusen-like nodules were also visible under the RPE layer (FIG. 25). Fluorescence in situ hybridization results also located *B. megaterium* in drusenoid but not in the normal tissues post inoculation (FIG. 6*e*). An elevation in the expression of CSA, CFH, CASPASE1, and NLRP3 proteins was also detected in the *B. megaterium* infected drusenoid lesion and para-lesion tissues as compared to the uninfected normal retina in macaque (FIG. 6*f*). Taken together, our data demonstrate that infection of *B. megaterium* can activate complement system and induce drusenoid pathology in vivo.

Discussion

Existence of Intraocular Microbiota and its Implication for Ocular Disease

In the past 10 years, the diversity and function of microbiota associated with human health and diseases have been extensively studied through high-throughput sequencing technologies and microbiomic/metagenomic analysis[11]. The local microbiota of the eye under physiological and pathological conditions remains largely uncharacterized[12,13]. The theory that the intraocular cavity is absolutely sterile under physiological conditions has led many researchers to reason that any types of foreign organisms are exogenous and pathogenic. However, our data indicate that even normal healthy eyes with no signs of ocular distress or infection have an individualized microbiome with compositional and functional diversity distinct from other body sites and tissues. Interestingly, the fact that *P. acnes* lives in the majority of human eyes and does not significantly induce intraocular inflammation raises a reasonable hypothesis that the normal intraocular microbiota plays a key role in maintaining the homeostasis of the local ocular environment. Similarly, the dysbiosis of the local microbial community can contribute to the etiology of many infectious, inflammatory, neoplastic, and degenerative ocular diseases. In addition, the idea that culture-positive microorganisms such as *P. acnes* were the major causes of intraocular inflammation warrants reexamination since these microorganisms may be part of the intraocular commensal microbiome while the real pathogens were uncultivable and missed. Many ocular procedures such as surgeries and intravitreal injection of anti-VEGF agents may also trigger the exposure of pathogenic intraocular microorganisms to host immune system responses. Therefore, future studies are needed to clearly define the symbiotic interactions between host and intraocular microbiota that support ocular health.

Infectious Etiology of AMD

Genetic studies have successfully identified various factors involved in the pathogenesis of AMD[3]. These factors all suggest that the activation of complement cascade and controlling of immune responses are the keys for AMD onset and progress. However, the initiator of AMD pathology (especially how drusen is formed) and the critical link between complement and AMD pathology have been unclear.

Figure 26:
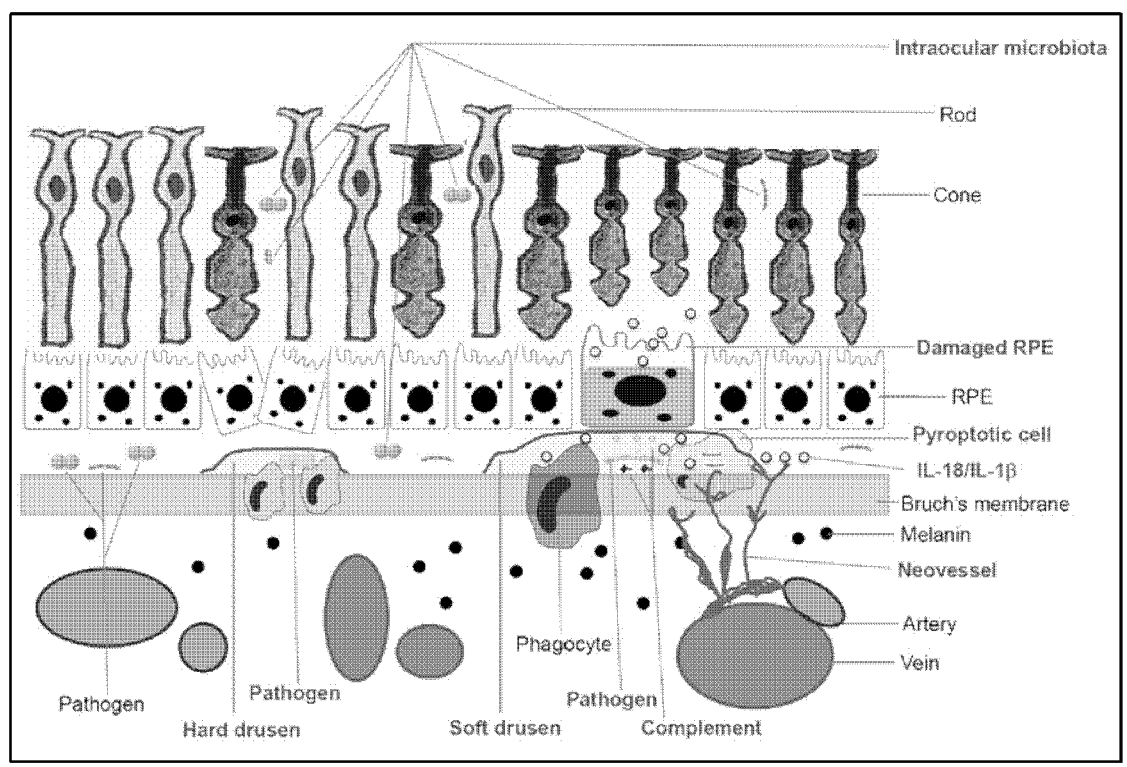
FIG. 26 illustrates proposed models of the drusen formation process.

Our findings that intraocular bacteria such as *B. megaterium* activate local complement-mediated immune responses can explain the formation of diversified drusen between RPE and Bruch's membrane. The major proteins found in drusen including complement components such as C1Q and immunoglobulin are all first-line anti-infectious agents[14]. Other drusen proteins such as amyloid A proteins[15,16], vitronectin[17], and Apolipoprotein E[18] exhibited proven roles as anti-infectious agents in recent reports. Therefore, the formation of drusen could represent the key response of the aging retina in controlling infiltrated bacterial pathogens. Due to the diversity of bacteria, the shape and size of drusen could vary[19]. In the case of hard drusen, where the infection may be cleared, drusen will disappear. However, certain pathogens such as *B. megaterium* will induce long term activation of immune responses in soft drusen and result in the damage of RPE cells and photoreceptors. Activation of inflammasome and pyroptosis of RPE or macrophage are protective responses against local infection, which is consistent with the previous finding that NLRP3 mediated inflammasome activation and IL-18 production protect the retina from neovascularization[20] (FIG. 26).

The infectious etiology of AMD is also consistent with the conclusions reached by all genetic studies. For example, a defective CFH, the negative regulator of complement activation induced by *B. megaterium* infection, will result in uncontrolled complement activation[21]. A defective HTRA1, the protease producing the active form of immunosuppressive cytokine TGF-, will result in decrease of local TGF-family proteins[22]. Both of these genetic variations can lead to dysregulation of local anti-infectious responses that damages RPE cells and photoreceptors. In addition, the potential difference in pathogenic microorganisms found in drusen may explain the association of varied genetic risk factors with different ethnic groups[23] (i.e. Caucasian vs Asian). Additionally, further genetic studies and clinical trials could benefit from metagenomicly informed patient stratification. Therefore, based on our data, the infectious etiology of AMD is a plausible mechanism by which early AMD pathology is initiated in the elderly. In summary, our finding provides a novel target for the diagnosis, treatment, and prevention of AMD.

REFERENCE LIST 1

References are listed below.
1. Jager R D, Mieler W F, Miller J W. Age-related macular degeneration. N Engl J Med 2008; 358:2606-17. doi: 10.1056/NEJMra0801537.
2. Sacconi R, Corbelli E, Querques L, Bandello F, Querques G A review of current and future management of geographic atrophy. Ophthalmol Ther 2017; 6:69-77. doi: 10.1007/s40123-017-0086-6. Epub 2017 Apr. 8.
3. Fritsche L G, Fariss R N, Stambolian D, Abecasis G R, Curcio C A, Swaroop A. Age-related macular degeneration: genetics and biology coming together. Annu Rev Genomics Hum Genet 2014; 15:151-71.:10.1146/annurev-genom-090413-25610. Epub 2014 Apr. 16.
4. Fritsche L G, Igl W, Bailey J N, et al. A large genome-wide association study of age-related macular degeneration highlights contributions of rare and common variants. Nat Genet 2016; 48:134-43. doi: 10.1038/ng.3448. Epub 2015 Dec. 21.
5. Fritsche L G, Chen W, Schu M, et al. Seven new loci associated with age-related macular degeneration. Nat Genet 2013; 2013 April; 45:433-9.
6. Forrester J V, Klaska I P, Yu T, Kuffova L. Uveitis in mouse and man. Int Rev Immunol 2013; 32:76-96. doi: 10.3109/08830185.2012.747524.
7. Wood D E, Salzberg S L. Kraken: ultrafast metagenomic sequence classification using exact alignments. Genome Biol 2014; 15:R46. doi: 10.1186/gb-2014-15-3-r46.
8. Abubucker S, Segata N, Goll J, et al. Metabolic reconstruction for metagenomic data and its application to the human microbiome. PLoS Comput Biol 2012; 8:e1002358. doi: 10.1371/journal.pcbi. Epub 2012 Jun. 13.
9. Deramo V A, Ting T D. Treatment of *Propionibacterium acnes* endophthalmitis. Curr Opin Ophthalmol 2001; 12:225-9.
10. Perry A, Lambert P. *Propionibacterium acnes*: infection beyond the skin. Expert Rev Anti Infect Ther 2011; 9:1149-56. doi: 10.586/eri.11.137.
11. Franzosa E A, Hsu T, Sirota-Madi A, et al. Sequencing and beyond: integrating molecular 'omics' for microbial community profiling. Nat Rev Microbiol 2015; 13:360-72. doi: 10.1038/nrmicro3451. Epub 2015 Apr. 27.
12. Kugadas A, Gadjeva M. Impact of microbiome on ocular health. Ocul Surf 2016; 14:342-9. doi: 10.1016/j.jtos.2016.04.004. Epub May 14.
13. St Leger A J, Desai J V, Drummond R A, et al. An ocular commensal protects against corneal infection by driving an interleukin-17 response from mucosal gammadelta T cells. Immunity 2017; 47:148-58.e5. doi: 10.1016/j.immuni.2017.06.014. Epub July 11.
14. Schumaker V N, Zavodszky P, Poon P H. Activation of the first component of complement. Annu Rev Immunol 1987; 5:21-42.
15. Johnson L V, Leitner W P, Rivest A J, Staples M K, Radeke M J, Anderson D H. The Alzheimer's A beta-peptide is deposited at sites of complement activation in pathologic deposits associated with aging and age-related macular degeneration. Proc Natl Acad Sci USA 2002; 99:11830-5. Epub 2002 Aug. 20.
16. Kumar D K, Choi S H, Washicosky K J, et al. Amyloid-beta peptide protects against microbial infection in mouse and worm models of Alzheimer's disease. Sci Transl Med 2016; 8:340ra72. doi: 10.1126/scitranslmed.aaf059.
17. Singh B, Su Y C, Riesbeck K. Vitronectin in bacterial pathogenesis: a host protein used in complement escape and cellular invasion. Mol Microbiol 2010; 78:545-60. doi: 10.1111/j.365-2958.010.07373.x. Epub 2010 Sep. 27.
18. Kattan O M, Kasravi F B, Elford E L, Schell M T, Harris H W. Apolipoprotein E-mediated immune regulation in sepsis. J Immunol 2008; 181:1399-408.
19. Khan K N, Mahroo O A, Khan R S, et al. Differentiating drusen: Drusen and drusen-like appearances associated with ageing, age-related macular degeneration, inherited eye disease and other pathological processes. Prog Retin Eye Res 2016; 53:70-106.:10.1016/j.preteyeres.2016.04.008. Epub May 10.
20. Doyle S L, Campbell M, Ozaki E, et al. NLRP3 has a protective role in age-related macular degeneration through the induction of IL-18 by drusen components. Nat Med 2012; 18:791-8. doi: 10.1038/nm.2717.
21. Mattapallil M J, Caspi R R. Compliments of factor H: What's in it for AMD? Immunity 2017; 46:167-9. doi: 10.1016/j.immuni.2017.02.008.
22. Friedrich U, Datta S, Schubert T, et al. Synonymous variants in HTRA1 implicated in AMD susceptibility impair its capacity to regulate TGF-beta signaling. Hum Mol Genet 2015; 24:6361-73. doi: 10.1093/hmg/ddv346. Epub 2015 Aug. 26.

23. Morrison M A, Magalhaes T R, Ramke J, et al. Ancestry of the Timorese: age-related macular degeneration associated genotype and allele sharing among human populations from throughout the world. Front Genet 2015; 6:238.:10.3389/fgene.2015.00238. eCollection 2015.

Methods

Sampling of Aqueous Humor from Patients

A topical antimicrobial drug, 0.5% levofloxacin eye drops (Cravit, Santen Pharmaceutical Co., Japan), was administered four times a day in both eyes for at least 3 days before the cataract surgery. On the day of surgery, patients received conjunctival sac irrigation using 0.9% sodium chloride solution at least twice and mydriasis using compound tropicamide eye drops. Following disinfection and draping, 5% povidone iodine (PVI) was applied on the eye for 30 seconds. The conjunctival sac was then irrigated with tobramycin solution for at least three times. After topical anesthesia with 0.5% alcaine (at least three times), auxiliary incision was performed using 1.5 mm stab knife (Alcon, USA) at the 2 o'clock position of the limbus. Aqueous humor was sampled via the auxiliary incision using a 1 ml sterile syringe before any other procedures were initiated. Immediately after collection, aqueous humor samples were transferred into sterile eppendorf tubes and stored at −80° C. prior to DNA extraction. The 0.9% sodium chloride solution (100 l) was also transferred from a fresh 1 ml sterile syringe into a sterile eppendorf tube, which served as the Blank control.

Sampling of Aqueous Humor from Post Mortem Human and Animal Eyes

The eye balls from post mortem donors (human donors from unrelated accidental death or laboratory animals free of diseases and genetic manipulation) were sterilized using 5% PVI and tobramycin solution, followed by washing in sterile 0.9% sodium chloride solution for three times in a cell culture hood. Aqueous humor was sampled using 1 ml sterile syringes.

Sampling of Plasma

Around 5 ml of peripheral venous blood was collected in an EDTA-anticoagulated vacutainer tube and then centrifuged for 10 min at 2,000 rpm. The supernatant was collected and stored at −80° C. prior to analysis.

Sampling of Conjunctiva

The conjunctival impression cytology samples from inferior bulbar conjunctiva were obtained using the following protocol: 1) topically anesthetize the eye with 1-2 drops of Alcaine Eye Drop (Alcon, USA) and keep the eye closed for several minutes; 2) using disposable tweezers, place the MF Membrane filter (Millipore, REF:HAWP01300, 0.45 μm) on the inferior bulbar conjunctiva with the edge of the membrane clear of the lower tear meniscus and gently press for 10-15 seconds; 3) remove the membrane and store it immediately at −80° C. in a sterile Eppendorf tube with 300 μl Tissue and Cell Lysis Solution containing 1 μl of Proteinase K, provided in the MasterPure Complete DNA and RNA Purification Kit (Epicentre, UK); 4) apply 1-2 drops of Neomycin Sulfate eye drops (Alcon, USA) to each examined eye.

Sampling of Eyelid Skin

Facial skin specimens were collected by scraping the skin of lower eyelid with a sterile MF Membrane filter (Millipore, REF:HAWP01300, 0.45 μm). The sample was inserted into a sterile eppendorf tube with 300 μl lysis solution (Epicentre).

Intraocular Bacterial Culture

The cooked meat medium (without antibiotics, 5 g/L Lab-Lemco' powder, 30 g/L peptone, 5 g/L yeast extract, 5 g/L NaH$_2$PO$_4$, 3 g/L glucose, and 2 g/L soluble starch) was purchased from Huankai Microbial Inc. (Guangzhou, China). Each culture was prepared in a 15 ml glass tube (purchased from Drtech Inc., Guangzhou China) with 6 ml cooked meat medium, sterilized dry beef granules, and 1.5 ml liquid paraffin wax (purchased from Huankai Microbial Inc., Guangzhou, China) on top. All tubes were then sterilized at 121° C. for 30 min in the HEV-to Autoclave instrument (HIRAYAMA, Japan). Aqueous humor or vitreous humor sample fluid was injected into above tube in sterilized cell culture hood and sealed, followed by culture with shaking (200 rpm) at 37° C. for 72 hours in the ZQTY-70F incubator (Zhichu Instrument Co., Ltd, Shanghai, China). Wax sealed tubes containing the culture medium underwent the incubation protocol but contained no aqueous humor sample to serve as the negative control. All cultures were then gram stained and subjected to microscopic examination.

In addition, the following agar mediums purchased from Huankai Microbial Inc. (Guangzhou, China) were sterilized at 121° C. for 30 min and used to culture aqueous humor samples at 37° C. for 5 days in a HettCube 200 incubator (Germany):

Brain-Heart Infusion Agar Medium (BHI Agar), pH 7.2: 12.5 g/L Brain infusion solids, 5 g/L Beef heart infusion solids, 10 g/L proteose peptone, 2 g/L Glucose, 5 g/L NaCl, 2.5 g/L Na$_2$HPO$_4$, 15 g/L Agar.

Soybean-Casein Digest Agar Medium (TSA Agar), pH 7.2: 15 g/L Tryptone, 5 g/L Soytone, 5 g/L NaCl, 15 g/L Agar.

Nutrient Agar 1 (N1 Agar), pH 7.2: 1 g/L Lab-Lemco' powder, 2 g/L Yeast extract, 5 g/L Peptone, 5 g/L NaCl, 15 g/L Agar.

Nutrient Agar 2 (N2 Agar), pH 7.2: 10 g/L Beef extract, 10 g/L Tryptone, 5 g/L NaCl, 3 g/L Yeast extract, 3 g/LCH$_3$COONa, 1 g/L Starch soluble, 0.5 g/L L-Cysteine hydrochloride, 15 g/L Agar.

Nutrient Agar 3 (N3 Agar), pH 7.2: 10 g/L Peptone, 3 g/L Beef extract, 5 g/L NaCl, 15 g/L Agar.

DNA Extraction from Aqueous Humor, Plasma, Conjunctiva and Skin Specimens

DNA extraction was carried out using MasterPure Complete DNA and RNA Purification Kit (Epicentre, UK) according to the manufacturer's protocol. Briefly, the lysed specimens were vigorously vortexed for 10 minutes, followed by incubation at 65° C. for 15 minutes. The RNA was removed by 5 μg RNase A and DNA was extracted by MPC Protein Precipitation Reagent and isopropanol-ethanol precipitation procedure.

Gram Staining

The aqueous humor was centrifuged at 14,000 rpm at 4° C. for 30 min to collect the precipitate, followed by cytocentrifugation using Cytospin (Thermo Scientific, US). Gram-stain was performed according to the manufacture's instruction. The gram staining procedures were repeated five times.

Metagenomic Data Analysis

Pre-processing of sequencing reads: All reads were first evaluated by FastQC for quality control. To maintain the consistency of alignment accuracy among all microbial reads, we first trimmed all reads to 75 bp using PrinSeq (v0.20.4)[1], which provided a best Q30 in our sample set. Paired-end reads from each sample were combined into one single file and treated as single-end reads. Low quality reads, replicated reads, and potential adapter sequences were removed using Fastx toolkit (v0.0.12). The reads containing more than 10% of ambiguous bases were depleted using PrinSeq (v0.20.4). Human reads were then removed from the subsequent analysis using HiSAT2 (v2.0.1)[2], BMTagger, and DeconSeq[3] to obtain clean non-human sequences.

Sequence analysis: The non-human sequences were first analyzed using the Kraken program[4], with the pre-built 4 GB database as the reference (including complete bacterial, archaeal, and viral genomes in RefSeq as of Dec. 8, 2014) (https://ccb.jhu.edu/software/kraken/), followed by mapping of non-human sequences against our custom fungal genomes (containing 68 species and 75 strains, downloaded from http://fungidb.org/fungidb/, on Mar. 12th 2015) using Burrows-Wheeler Aligner (BWA0.7.5a) with 3 mismatches. The relative abundance of each species was calculated by the ratio of the total mapped reads of each species, normalized by their genome size and the total mapped microbial reads within each sample. Community diversity (Shannon index and evenness) was calculated according to the method described in Mothur program after using a subsampling cutoff of 500 microbial sequences per sample. The HMP Unified Metabolic Analysis Network (HUMAnN2)[5] was used to analyze the abundance of microbial genes and KEGG pathways. Principal component analysis (PCA) was performed on the relative abundance of bacterial species or microbial genes using Ade4 package in R statistical software (v3.1.1) after using a subsampling cutoff of 500 microbial sequences per sample or 1 read per gene. LDA Effect Size (LefSe)[6] was used to identify species, microbial genes, and functional pathways characterizing the differences among sample groups.

Detection of Bacteria in Drusen and Retinal Tissues

The drusen/non-drusen and lesion/non-lesion tissues on AMD slides were microdissected manually from uncovered, hematoxylin and eosin (HE) stained glass slides. Total DNA was isolated using AllPrep DNA/RNA FFPE Kit (Qiagen, USA) following the manufacture's instruction. Real-time PCR was performed to detect the relative amount of all bacteria in retinal tissues using either RT[2] SYBR Green qPCR Mastermix (SABiosciences, USA) and ABI 7500 Real-time PCR System (Life Technologies, USA) or KAPA SYBR FAST Universal qPCR kit (Kapa, USA) and Roche LightCycler 480 (Roche, USA). Bacterial relative abundance was normalized to the level of human ACTB.

Imaging Flow Cytometry

Multispectral imaging cytometry was used to visualize the size and morphology of microorganisms and human cells. The mixture of 1 µl diamidino-phenyl-indole (DAPI) and 1 µl microbeads (BD, USA) was added into 10 µl aqueous humor and analyzed on the ImageStreamX Mark II Imaging Flow Cytometer (Merck, USA).

Animal Studies

All animal experiments were performed following the guidelines for housing and care of laboratory animals. The protocol was approved by the Sun Yat-sen University Animal Care and Use Committee and was consistent with the Association for Research in Vision and Ophthalmology guidelines for studies in animals (protocol #SYXK2014-0023 and #SYXK2015-0058). Male New Zealand white rabbits (aged 8-12 weeks and weighted 2.2-2.4 kg) and rats (aged 6-8 weeks) were purchased from Huadong Xinhua Laboratory Animal Center (Guangdong, China). Male adult macaques (*Macaca fascicularis*, aged 3-4 years) were obtained from the Blooming-Spring Biotechnology Co. Ltd (Guangdong, China).

Analysis of Intravitreal Bacterial Infection in Macaque

The macaques were sedated by intramuscular injection of a mixture of Tiletamine Hydrochloride (2.5 mg/kg) and Xolazepam Hydrochloride (2.5 mg/kg). After topical anesthesia (0.5% Proparacaine Hydrochloride), the eyes were immediately visualized in vivo using a light microscope. The pupils were then dilated with 0.5% tropicamide and 0.5% phenylephrine to obtain the fundus photographs. Intravitreal injection of bacterial solutions (1000 CFU [colony forming units] in a volume of 50 µl) or sonication-inactivated bacterial proteins (from 1000 CFU bacteria) was performed with a 1 ml syringe and 30-gauge needle after ocular surface disinfection with 5% PVI solution. Slit lamp and fundus examinations were conducted for all macaques within 3 days after the injection. The severity of the endophthalmitis was graded according to a previously described standard. The macaques were euthanized 3 days post inoculation and both eyeballs were enucleated for histopathological, intraocular cytokine, and bacteria analyses. The eyeballs were fixed in 4% paraformaldehyde for 48 h and then embedded in paraffin. Sections were cut on a microtome at 5 µm and stained with hematoxylin and eosin (H&E).

Bacterial Strains

Bacterial strains including *Propionibacterium acnes* BNCC336649, *Bacillus megaterium* BNCC190686, and *Bacillus licheniformis* BNCC186069 were purchased from BeNa Culture Collection (Beijing, China). All strains of bacteria were first cultured overnight at 37° C. on agar plates following the standard protocols provided by the manufacturer. The bacterial cultures were then washed in PBS and resuspended as 1×10⁶ CFU/µl solutions and further diluted in PBS as injection solutions.

RNA Extraction and Real-Time PCR

Total RNA was extracted from 100 µl aqueous humor using MasterPure Complete DNA & RNA Purification Kit (Epicentre, UK). DNA-free RNA was reverse transcribed into DNA using the All-In-One Master Mix Kit (Kapa, USA). Real-time PCR was performed using KAPA SYBR FAST Universal qPCR kit (Kapa, USA) to quantify bacterial relative abundance and was normalized to the expression of human or macaques ACTB. The primers used were listed in Table 4.

TABLE 4

| Target Gene | Forward | Reverse |
| --- | --- | --- |
| Human-ACTB | AGCGGGAAATCGTGCGTGAC (SEQ ID NO: 31) | CAGGCAGCTCGTAGCTCTTCT (SEQ ID NO: 32) |
| P. spp-16S | CCTGCCCTTGACTTTGG (SEQ ID NO: 33) | AAGCCGCGAGTCCATC (SEQ ID NO: 34) |
| P. acnes-PPA_RS04200 | GATTGGTTTACTACCCGTGAGCG (SEQ ID NO: 1) | ATAGCAGGGATTCCAGCGACA (SEQ ID NO: 2) |

TABLE 4-continued

| Target Gene | Forward | Reverse |
| --- | --- | --- |
| B. megaterium | GGTTCAATGAGCCTACT (SEQ ID NO: 3) | GCCAGCGTCTTTCC (SEQ ID NO: 4) |
| B. licheniformis | TCCCGTCTTCATCTACTGC (SEQ ID NO: 5) | GGACGCCTACTGGACAA (SEQ ID NO: 6) |
| Pseudomonasputida | CCGCACAGGTTGTCCCA (SEQ ID NO: 7) | CTGCTGCGTTGTCGTTCC (SEQ ID NO: 8) |
| Xanthomonasoryzae | TGGTGCGATGGCGATGTT (SEQ ID NO: 9) | GGTTGCGGCATGTGCTTT (SEQ ID NO: 10) |
| Stenotrophomo-nasmaltophilia | GCGTTCGTCCGCTGTCA (SEQ ID NO: 11) | GGCAACCCGCTAGAATCCC (SEQ ID NO: 12) |
| Lactobacillusreuteri | TAGTGGATAATGCCGTTGA (SEQ ID NO: 13) | CGGTTTGCCAGAAGC (SEQ ID NO: 14) |
| Staphylococcus-haemolyticus | GTTACACTGCTCCGACAA (SEQ ID NO: 15) | TTCGCATCAGCAATAA (SEQ ID NO: 16) |
| Cytophagahutchinsonii | GCTGGCTCCTTTGG (SEQ ID NO: 17) | GCATTACTGCCTGGTG (SEQ ID NO: 18) |
| Gardnerellavaginalis | GACTCCGACTTGTTT (SEQ ID NO: 19) | CATTATCTGGCGTTTTAGC (SEQ ID NO: 20) |
| Staphylococcusaureus | GAAGCGGAGTTCAAAGG (SEQ ID NO: 21) | ATGGCAAATCACCAATCA (SEQ ID NO: 22) |
| Pseudomonasaeruginosa | GACCAGGTAGCCGTCGTTCTC (SEQ ID NO: 23) | TGCTGACCCTGACCGACATTC (SEQ ID NO: 24) |
| Bacilluscereus | GAAGTGCGTGCGTATAGTGT (SEQ ID NO: 25) | AAAGAACGACCAAGTGCTG (SEQ ID NO: 26) |
| Staphylococcus-epidermidis | TTGAAGTGAAACGTCCTC (SEQ ID NO: 27) | TGTCTCATCTAACCACC (SEQ ID NO: 28) |
| Enterococcusfaecium | TGGAGCGATTATACCG (SEQ ID NO: 29) | GTACCCGCTTGATTGA (SEQ ID NQ: 30) |
| M. fascicularis-ACTB | CGGGAAATCGTGCGTGAC (SEQ ID NO: 35) | ATCGGGCAGCTCGTAGC (SEQ ID NO: 36) |
| M. fascicularis-IL1B | CTTACTACAGCGGCAACG (SEQ ID NO: 37) | CCATCCAGAGGGCAGAG (SEQ ID NO: 38) |
| M. fascicularis-ILI7A | CAAGGCTGATGGGAACG (SEQ ID NO: 39) | CACGGACACCAGTATCTTCTCC (SEQ ID NO: 40) |
| M. fascicularis-IL6 | GCTGCTCCTGGTGTTGC (SEQ ID NO: 41) | TGCCGTCGAGGATGTAC (SEQ ID NQ: 42) |
| M. fascicularis-TNFA | CTCCAGTGGCTGAACCG (SEQ ID NO: 43) | TGAAGAGGACCTGGGAGTAG (SEQ ID NO: 44) |
| M. fascicularis-IFNG | GAATGTCCAACGCAAAG (SEQ ID NO: 45) | CTCGAAACATCTGACTCCT (SEQ ID NO: 46) |
| M. fascicularis-C5 | CGAGATGCGTCAAAG (SEQ ID NO: 47) | CTTACTGGTAACAGGGTC (SEQ ID NO: 48) |
| M. fascicularis-CFH | GCGTAGACCATACTTTCC (SEQ ID NO: 49) | GTGACCACCCATCTTG (SEQ ID NO: 50) |
| Bacterial16S (FAM) g | GCATGATGATTTGACGTCATCCCCACCT TCCTCCGGTTTG (SEQ ID NO: 51) | |
| B. megaterium (Cy3) | TACGTCCTTACGGTTACTCC (SEQ ID NO: 52) | |

ELISA

The active forms of cytokines and complement components in cell culture supernatants or aqueous humor specimens from bacteria inoculated macaque eyes were measured using Human IL-1β ELISA kit (Cat #KT98060), Human IL-18 ELISA kit (Cat #KT98065), Human C5a ELISA kit (Cat #KT40003), Monkey IL-1β ELISA kit (Cat #KT49531), Monkey IL-18 ELISA kit (Cat #KT56387), Monkey C5a ELISA kit (Cat #KT40004), and Monkey CFH ELISA kit (Cat #KT45321; MSKBIO, Wuhan, China) according to the manufacture's instruction.

βCell Culture and Staining

Human ARPE19 cells (ATCC, USA) were cultured in DMEM supplied with 2.5 mM L-glutamine and 10% FBS. After coculture without or with bacteria, ARPE19 cells were incubated with PI and Annexin V-APC (Cat #88-8007-72, eBioscience, USA) for 30 min. The cell death was measured with MACSQuant Analyzer 10 flow cytometer (Miltenyi Biotec, Germany).

Fluorescence In Situ Hybridization

Fluorescence in situ hybridization was performed using the FISH kit (Bis-QD355, BersinBio, China). Formalin-fixed paraffin-embedded sections were baked at 70° C. for 60 min, de-paraffinized in dimethylbenzene (5 min per time, three times), and washed in 100% ethanol (5 min per time, two times). After air dry on super-clean bench, the protease K was used to digest tissues for 15 min at 37° C., followed by washing with sterile PBS solution for 5 min. Then, the sections were sequentially incubated in 78° C. denatured solution, followed by washing in 70%, 85%, 100% ethanol solutions at −20° C. (5 min per solution). Sections were then hybridized to a general bacteria 16S probe labeled by FAM and/or a *B. megaterium* specific probe labeled by Cy3 overnight at 42° C. After hybridization, 50% formamide and SSC solution were used to wash all sections. DAPI was used as the control.

Statistical Analysis

All statistical analysis was performed in the SPSS software (v17.0). Data were represented as mean±standard error unless otherwise indicated. The parametric (student's) t or F tests were used.

Results

Reagent and Environmental Contamination Controls in High-Throughput Sequencing Experiments Potential reagent and environmental contamination in high-throughput sequencing experiments were a concern in our study. We thus paid great attention to myriad negative controls for both environments and reagents throughout these studies, including the Blank, Wash Solution, Anesthesia, Disinfectant, NaCl Solution, and Mydriatic samples. Eight independent samples ("Blank") were collected following the exact procedures for aqueous humor (AH) collection, substituting 100 μl 0.9% sodium chloride solution instead of AH into the sample collection tubes in the operation room. Similarly, two each Wash Solution, Anesthesia, Disinfectant, NaCl Solution, and Mydriatic samples were collected as controls for metagenomic sequencing analysis of AH specimens. The 80 tissue samples as well as environmental and reagent controls were analyzed using metagenomic sequencing approach, among which we failed to detect any sequencing reads in one unreplaceable conjunctival sample. We found no detectable DNA in all control samples, while an average of 0.13 ng/μl DNA could be detected in AH samples using Qubit (Life, USA) (FIG. 14a). As a result, over amplified DNA in control samples resulted in almost all low quality and/or repeat reads (FIG. 14b). These data clearly differentiated the controls from AH samples, and this validation process confirmed that the reads from AH samples were indeed from a true metagenomic community.

Intraocular Microbiota in Animal Eyes

Figure 15:
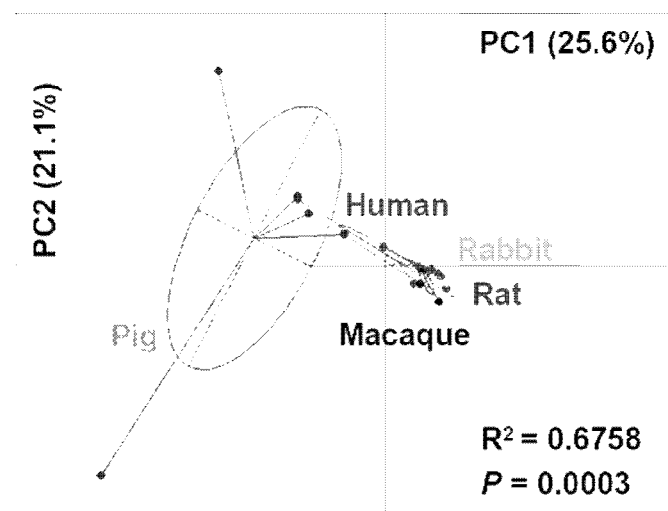
FIG. 15 illustrates similarity of intraocular metagenome in the eyes of human, rabbit, rat, macaque, and pig analyzed using principle coordination analysis. P value was calculated using PERMANOVA test.

To assess whether an intraocular microbiota would be found in both human and animals, we collected postmortem AH specimens from 4 fresh human eyes that were free of ocular diseases (individuals deceased due to unrelated accidents, the demographic characteristics of all subjects were listed in Table 1), 5 macaque eyes (*Macaca fascicularis*), 5 rabbit eyes (*Oryctolagus cuniculus*), 5 rat eyes (*Rattus norvegicus*), and 5 pig eyes (*Sus scrofa*) in the sterile Laminar Flow Hood. Metagenomic analysis was performed on these 24 AH specimens. Our data suggest that unique live microbiota could be found in human eyes free of any ocular diseases. Animals such as macaque, rabbit, and rat had similar intraocular microbiota as human had, which differed substantially from pigs (FIG. 15).

*Bacillus megaterium* Induces Activation of Complement, Pyroptosis of RPE Cells in Vitro Previous studies demonstrate that drusen contains a variety of complement components and polysaccharides in addition to many other proteins[8]. In addition, the drusen components activate inflamasomes and promote expression of IL-1β and IL-18[9,10]. We therefore first examined whether *B. megaterium* was able to induce the activation of complement system and promote the secretion of IL-1β and IL-18, by ARPE19 cells in vitro. As shown in FIG. 22a, we found *B. megaterium* but not *P. acnes* significantly increased the pyroptosis of RPE cells in a time dependent manner. The activation of complement system was confirmed by the production of active form of C5A protein (FIG. 22b). Interestingly, both bacteria induced secretion of CFH proteins, while the induction of CFH was more profound by *B. megaterium* than by *P. acnes* (FIG. 22b). As the result of pyroptosis, in vitro infection of *B. megaterium*, but not *P. acnes*, led to secretion of active IL-1β and IL-18 by RPE cells (FIG. 22b). These results indicate that infection of *B. megaterium* can lead to inflammation mediated by RPE.

REFERENCE LIST 2

References are listed below.

1. Schmieder R, Edwards R. Quality control and preprocessing of metagenomic datasets. Bioinformatics 2011; 27:863-4. doi: 10.1093/bioinformatics/btr026. Epub 2011 Jan. 28.
2. Kim D, Langmead B, Salzberg S L. HISAT: a fast spliced aligner with low memory requirements. Nat Methods 2015; 12:357-60. doi: 10.1038/nmeth.3317. Epub 2015 Mar. 9.
3. Schmieder R, Edwards R. Fast identification and removal of sequence contamination from genomic and metagenomic datasets. PLoS One 2011; 6:e17288. doi: 10.1371/journal.pone.0017288.
4. Wood D E, Salzberg S L. Kraken: ultrafast metagenomic sequence classification using exact alignments. Genome Biol 2014; 15: R46. doi: 10.1186/gb-2014-15-3-r46.
5. Abubucker S, Segata N, Goll J, et al. Metabolic reconstruction for metagenomic data and its application to the human microbiome. PLoS Comput Biol 2012; 8:e1002358. doi: 10.1371/journal.pcbi. Epub 2012 Jun. 13.
6. Segata N, Izard J, Waldron L, et al. Metagenomic biomarker discovery and explanation. Genome Biol 2011; 12:R60. doi: 10.1186/gb-2011-12-6-r60.

7. Peyman G A, Paque J T, Meisels H I, Bennett T O. Postoperative endophthalmitis: a comparison of methods for treatment and prophlaxis with gentamicin. Ophthalmic Surg 1975; 6:45-55.
8. Crabb J W, Miyagi M, Gu X, et al. Drusen proteome analysis: an approach to the etiology of age-related macular degeneration. Proc Natl Acad Sci USA 2002; 99:14682-7. Epub 2002 Oct. 21.
9. Doyle S L, Campbell M, Ozaki E, et al. NLRP3 has a protective role in age-related macular degeneration through the induction of IL-18 by drusen components. Nat Med 2012; 18:791-8. doi: 10.1038/nm.2717.
10. Wang Y, Hanus J W, Abu-Asab M S, et al. NLRP3 upregulation in retinal pigment epithelium in age-related macular degeneration. Int J Mol Sci 2016; 17(1).E73. doi: 10.3390/ijms17010073.

The Test of Antibiotics to Treat AMD Through Inhibiting the Growth of Microbiota
Method
Antibiotic Sensitivity Testing The bacterial culture medium (HuanKai Microbial, Guangzhou, China) containing peptone 5 g, beef extract 3 g, NaCl 5 g, agar 15 g, and $MnSO_4$ 5 mg in 1 L $ddH_2O$ (pH=7.2) was prepared in conical flask (Drtech, Guangzhou, China) and was sterilized in the autoclave (HIRAYAMA, HEV-50, Japan) at 121° C. for 30 min. Antibiotics (ampicillin, vancomycin, neomycin, metronidazole, and tetracycline, purchased from Sigma, USA) at various concentrations were added into cooled medium. Bacillus megaterium (total $1*10^7$ per culture) was cultured in the incubator (HettCube 200, Germany) at 37° C. for 24 h.

Result

Figure 27:
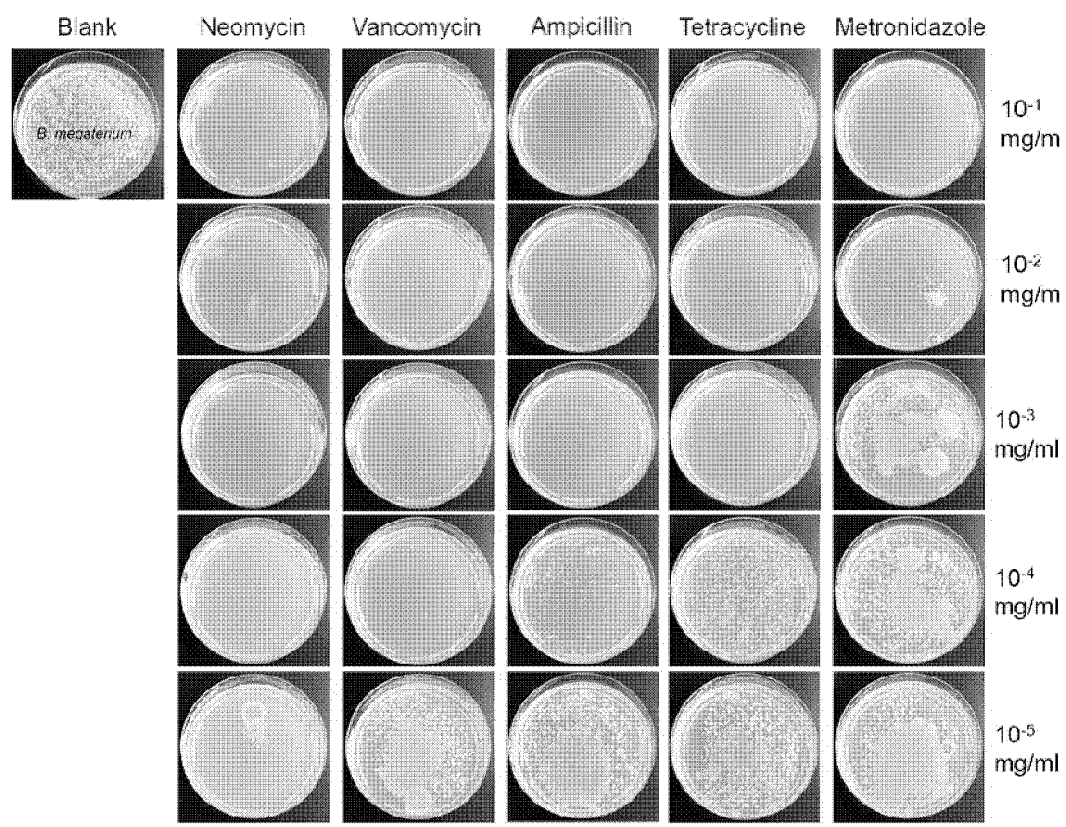
FIG. 27 illustrates the sensitivity of *Bacillus megaterium* to several antimicrobial agents.

To test whether antibiotics can control the growth of Bacillus megaterium in vitro and in vivo, an antibiotic sensitivity screening test in petri dishes was carried out. The sensitivity of Bacillus megaterium to several major antimicrobial agents including Ampicillin, vancomycin, neomycin, metronidazole, and tetracycline were examined using the minimum inhibitory concentration (MIC) method. As shown in FIG. 27, Bacillus megaterium was most sensitive to neomycin, while metronidazole was 10000-fold less effective in controlling the growth of Bacillus megaterium.

Figure 28:
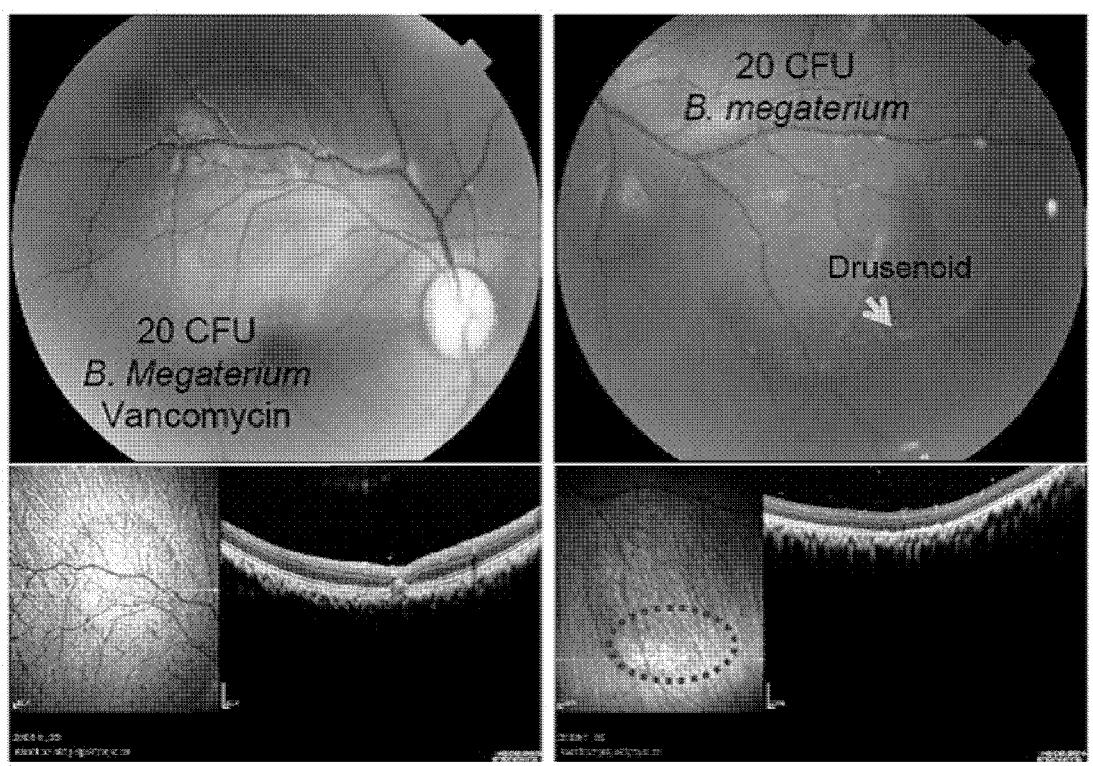
FIG. 28 illustrates that an antibiotic treatment is able to change the bacteria-induced drusenoid pathology in monkey retinal tissues.

Next, Bacillus megaterium subretinal inoculation model was used to test whether antibiotics might be able to change the bacteria-induced drusenoid pathology in monkey retinal tissues. Although neomycin showed the best in vitro activity controlling the expansion of Bacillus megaterium, intraocular administration of neomycin in monkey induced significant ocular complications including ophthalmatrophia (data not shown). On the other hand, intravitreous administration of vancomycin (0.5 mg, one injection on Day 2 post bacterial inoculation) resulted in a reduction in the size of drusenoid lesion in retinal tissue (FIG. 28b, 28d), as compared to the lesion shown in FIG. 28a, 28c. These data suggest that vancomycin is able to inhibit the growth of Bacillus megaterium in vitro and in vivo, therefore may be used to treat age-related macular degeneration.

The invention claimed is:

1. A kit or device for assessing age-related macular degeneration (AMD) in a subject, which kit or device comprises reagents for assessing the presence, absence, quantity, and/or the infectious status of *Bacillus megaterium* in an intraocular space, cavity or sample of a subject, wherein the etiology of said AMD comprises infection of said *Bacillus megaterium* in said intraocular space or cavity of said subject, and which kit or device further comprises a tool for obtaining a sample from said intraocular space or cavity of said subject.

2. The kit or device of claim 1, wherein the reagents comprise reagents to be used in a molecular assay.

3. The kit or device of claim 1, wherein the reagents comprise reagents to be used in a binding assay.

4. The kit or device of claim 3, wherein the reagents comprise reagents to be used in an immunoassay.

5. The kit or device of claim 4, wherein the immunoassay is selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

6. The kit or device of claim 2, wherein the reagents comprise reagents for isolating, amplifying, ligating, hybridizing and/or sequencing a polynucleotide of *Bacillus megaterium*.

7. The kit or device of claim 2, wherein the reagents comprise reagents for amplifying the polynucleotide using a procedure selected from the group consisting of polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self-sustained sequence replication (3 SR), and loop-mediated isothermal amplification (LAMP).

8. The kit or device of claim 2, wherein the reagents comprise reagents for polynucleotide sequencing that is conducted with a format selected from the group consisting of Maxam-Gilbert sequencing, a chain-termination method, shotgun sequencing, bridge PCR, single-molecule real-time sequencing, ion semiconductor, sequencing by synthesis, sequencing by ligation, chain termination, massively parallel signature sequencing, polony sequencing, 454 pyrosequencing, Illumina Solexa sequencing, DNA nanoball sequencing, heliscope single molecule sequencing, single molecule real time sequencing, nanopore DNA sequencing, tunnelling currents DNA sequencing, sequencing by hybridization, sequencing with mass spectrometry, microfluidic Sanger sequencing, RNAP sequencing, and in vitro virus high-throughput sequencing.

9. The kit or device of claim 2, wherein the reagents comprise reagents for sequencing analysis and/or PCR analysis.

10. The kit or device of claim 9, wherein the reagents comprise reagents for metagenomic sequencing analysis of *Bacillus megaterium*.

11. The kit or device of claim 9, wherein the reagents comprise reagents for real-time PCR analysis of *Bacillus megaterium*.

12. The kit or device of claim 1, wherein the tool is configured for obtaining a sample from aqueous humor in anterior chamber, a suspensory ligament, ciliary body, ciliary body and muscle, vitreous humor in posterior chamber, retina, choroid, optic nerve, lens, or iris of a subject.

13. The kit or device of claim 1, which comprises reagents for assessing live *Bacillus megaterium* for assessing AMD in the subject.

14. The kit or device of claim 1, which further comprises a reagent for assessing activation of complement system and/or induction of inflammation in the intraocular space, cavity or sample of a subject for assessing AMD in the subject.

15. The kit or device of claim 1, which further comprises a reagent or structure for assessing clinical symptoms of AMD in a subject.

16. The kit or device of claim 1, which is configured for risk assessment, diagnosis, prognosis, stratification and/or treatment monitoring of AMD in a subject.

17. The kit or device of claim 1, which further comprises a control reagent or a calibrator.

18. The kit or device of claim 1, which further comprises a drug, a surgery tool or an implantable device for treating or preventing AMD in the subject.

19. The kit or device of claim 1, which comprises a kit.

* * * * *

SEQUENCE LISTING

```
<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gattggttta ctacccgtga gcg                                              23

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
atagcaggga ttccagcgac a                                                21

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
ggttcaatga gcctact                                                     17

<210> SEQ ID NO 4
<211> LENGTH: 14
<212> TYPE: DNA
<213> ORGANISM: Artificial Sequence
```

-continued

```
<220> FEATURE:
<223> OTHER INFORMATION: Primer

<400> SEQUENCE: 4
gccagcgtct ttcc                                                      14

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
tcccgtcttc atctactgc                                                 19

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
ggacgcctac tggacaa                                                   17

<210> SEQ ID NO 7
<211> LENGTH: 17
<212> TYPE: DNA
<213> ORGANISM: Artificial Sequence
<220> FEATURE:
<223> OTHER INFORMATION: Primer

<400> SEQUENCE: 7
ccgcacaggt tgtccca                                                   17

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ctgctgcgtt gtcgttcc                                                  18

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
tggtgcgatg gcgatgtt                                                  18

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
ggttgcggca tgtgcttt                                                  18
```

```
<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
gcgttcgtcc gctgtca                                                   17

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ggcaacccgc tagaatccc                                                 19

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tagtggataa tgccgttga                                                 19

<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
cggtttgcca gaagc                                                     15

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
gttacactgc tccgacaa                                                  18

<210> SEQ ID NO 16
<211> LENGTH: 16
<212> TYPE: DNA
<213> ORGANISM: Artificial Sequence
<220> FEATURE:
<223> OTHER INFORMATION: Primer

<400> SEQUENCE: 16
ttcgcatcag caataa                                                    16

<210> SEQ ID NO 17
<211> LENGTH: 14
<212> TYPE: DNA
<213> ORGANISM: Artificial Sequence
<220> FEATURE:
<223> OTHER INFORMATION: Primer
```

```
<400> SEQUENCE: 17
gctggctcct ttgg                                                      14

<210> SEQ ID NO 18
<211> LENGTH: 16
<212> TYPE: DNA
<213> ORGANISM: Artificial Sequence
<220> FEATURE:
<223> OTHER INFORMATION: Primer

<400> SEQUENCE: 18
gcattactgc ctggtg                                                    16

<210> SEQ ID NO 19
<211> LENGTH: 15
<212> TYPE: DNA
<213> ORGANISM: Artificial Sequence
<220> FEATURE:
<223> OTHER INFORMATION: Primer

<400> SEQUENCE: 19
gactccgact tgttt                                                     15

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
cattatctgg cgttttagc                                                 19

<210> SEQ ID NO 21
<211> LENGTH: 17
<212> TYPE: DNA
<213> ORGANISM: Artificial Sequence
<220> FEATURE:
<223> OTHER INFORMATION: Primer

<400> SEQUENCE: 21
gaagcggagt tcaaagg                                                   17

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
atggcaaatc accaatca                                                  18

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
gaccaggtag ccgtcgttct c                                              21

<210> SEQ ID NO 24
```

```
<211> LENGTH: 21
<212> TYPE: DNA
<213> ORGANISM: Artificial Sequence
<220> FEATURE:
<223> OTHER INFORMATION: Primer

<400> SEQUENCE: 24
tgctgaccct gaccgacatt c                                              21

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gaagtgcgtg cgtatagtgt                                                20

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aaagaacgac caagtgctg                                                 19

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ttgaagtgaa acgtcctc                                                  18

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
tgtctcatct aaccacc                                                   17

<210> SEQ ID NO 29
<211> LENGTH: 16
<212> TYPE: DNA
<213> ORGANISM: Artificial Sequence
<220> FEATURE:
<223> OTHER INFORMATION: Primer

<400> SEQUENCE: 29
tggagcgatt ataccg                                                    16

<210> SEQ ID NO 30
<211> LENGTH: 16
<212> TYPE: DNA
<213> ORGANISM: Artificial Sequence
<220> FEATURE:
<223> OTHER INFORMATION: Primer

<400> SEQUENCE: 30
```

```
gtacccgctt gattga                                                  16
```

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31

```
agcgggaaat cgtgcgtgac                                              20
```

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32

```
caggcagctc gtagctcttc t                                            21
```

<210> SEQ ID NO 33
<211> LENGTH: 17
<212> TYPE: DNA
<213> ORGANISM: Artificial Sequence
<220> FEATURE:
<223> OTHER INFORMATION: Primer

<400> SEQUENCE: 33

```
cctgcccttg actttgg                                                 17
```

<210> SEQ ID NO 34
<211> LENGTH: 16
<212> TYPE: DNA
<213> ORGANISM: Artificial Sequence
<220> FEATURE:
<223> OTHER INFORMATION: Primer

<400> SEQUENCE: 34

```
aagccgcgag tccatc                                                  16
```

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35

```
cgggaaatcg tgcgtgac                                                18
```

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36

```
atcgggcagc tcgtagc                                                 17
```

<210> SEQ ID NO 37
<211> LENGTH: 18
<212> TYPE: DNA

```
<213> ORGANISM: Artificial Sequence
<220> FEATURE:
<223> OTHER INFORMATION: Primer

<400> SEQUENCE: 37
cttactacag cggcaacg                                                18

<210> SEQ ID NO 38
<211> LENGTH: 17
<212> TYPE: DNA
<213> ORGANISM: Artificial Sequence
<220> FEATURE:
<223> OTHER INFORMATION: Primer

<400> SEQUENCE: 38
ccatccagag ggcagag                                                 17

<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39
caaggctgat gggaacg                                                 17

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
cacggacacc agtatcttct cc                                           22

<210> SEQ ID NO 41
<211> LENGTH: 17
<212> TYPE: DNA
<213> ORGANISM: Artificial Sequence
<220> FEATURE:
<223> OTHER INFORMATION: Primer

<400> SEQUENCE: 41
gctgctcctg gtgttgc                                                 17

<210> SEQ ID NO 42
<211> LENGTH: 17
<212> TYPE: DNA
<213> ORGANISM: Artificial Sequence
<220> FEATURE:
<223> OTHER INFORMATION: Primer

<400> SEQUENCE: 42
tgccgtcgag gatgtac                                                 17

<210> SEQ ID NO 43
<211> LENGTH: 17
<212> TYPE: DNA
<213> ORGANISM: Artificial Sequence
<220> FEATURE:
<223> OTHER INFORMATION: Primer

<400> SEQUENCE: 43
ctccagtggc tgaaccg                                                 17
```

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tgaagaggac ctgggagtag                                        20

<210> SEQ ID NO 45
<211> LENGTH: 17
<212> TYPE: DNA
<213> ORGANISM: Artificial Sequence
<220> FEATURE:
<223> OTHER INFORMATION: Primer

<400> SEQUENCE: 45
gaatgtccaa cgcaaag                                           17

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
ctcgaaacat ctgactcct                                         19

<210> SEQ ID NO 47
<211> LENGTH: 15
<212> TYPE: DNA
<213> ORGANISM: Artificial Sequence
<220> FEATURE:
<223> OTHER INFORMATION: Primer

<400> SEQUENCE: 47
cgagatgcgt caaag                                             15

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
cttactggta acagggtc                                          18

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
gcgtagacca tactttcc                                          18

<210> SEQ ID NO 50
<211> LENGTH: 16
<212> TYPE: DNA
<213> ORGANISM: Artificial Sequence
<220> FEATURE:

```
<223> OTHER INFORMATION: Primer

<400> SEQUENCE: 50
gtgaccaccc atcttg                                                        16

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
gcatgatgat ttgacgtcat ccccaccttc ctccggtttg                              40

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tacgtcctta cggttactcc                                                    20
```